(12) United States Patent
Hebach et al.

(10) Patent No.: US 9,056,843 B2
(45) Date of Patent: Jun. 16, 2015

(54) TRIFLUOROMETHYL-OXADIAZOLE DERIVATIVES AND THEIR USE IN THE TREATMENT OF DISEASE

(75) Inventors: Christina Hebach, Muenchenstein (CH); Emilie Joly, Colmar (FR); Joerg Kallen, Basel (CH); James Gilbert Ternois, Kembs (FR); Marina Tintelnot-Blomley, Maulburg (DE)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 14/131,558

(22) PCT Filed: Jul. 6, 2012

(86) PCT No.: PCT/IB2012/053470
§ 371 (c)(1),
(2), (4) Date: Jan. 8, 2014

(87) PCT Pub. No.: WO2013/008162
PCT Pub. Date: Jan. 17, 2013

(65) Prior Publication Data
US 2014/0142105 A1 May 22, 2014

Related U.S. Application Data

(60) Provisional application No. 61/505,592, filed on Jul. 8, 2011.

(51) Int. Cl.
| | |
|---|---|
| *C07D 271/06* | (2006.01) |
| *C07D 413/12* | (2006.01) |
| *C07D 413/10* | (2006.01) |
| *A61K 31/5377* | (2006.01) |
| *A61K 31/4439* | (2006.01) |
| *A61K 31/454* | (2006.01) |
| *A61K 31/4245* | (2006.01) |
| *A61K 31/496* | (2006.01) |

(52) U.S. Cl.
CPC ............ *C07D 271/06* (2013.01); *C07D 413/10* (2013.01); *C07D 413/12* (2013.01); *A61K 31/4245* (2013.01); *A61K 31/4439* (2013.01); *A61K 31/454* (2013.01); *A61K 31/496* (2013.01); *A61K 31/5377* (2013.01)

(58) Field of Classification Search
CPC .. C07D 271/06; C07D 413/10; C07D 413/12; A61K 31/4245; A61K 31/4439; A61K 31/454; A61K 31/496; A61K 31/5377
See application file for complete search history.

(56) References Cited

U.S. PATENT DOCUMENTS

| | | |
|---|---|---|
| 4,871,753 A | 10/1989 | Rohr |
| 2005/0288282 A1 | 12/2005 | Delorme et al. |
| 2006/0058298 A1 | 3/2006 | Delorme et al. |
| 2014/0329825 A1 | 11/2014 | Hebach et al. |

FOREIGN PATENT DOCUMENTS

| | | |
|---|---|---|
| JP | 56065881 | 6/1981 |
| WO | 2005040152 A1 | 5/2005 |
| WO | 2005092899 A1 | 10/2005 |
| WO | 2007069773 A1 | 6/2007 |
| WO | 2008011131 A1 | 1/2008 |
| WO | 2009019656 A1 | 2/2009 |
| WO | 2009029632 A1 | 3/2009 |
| WO | 2011005608 A1 | 1/2011 |
| WO | 2011/088187 A1 | 7/2011 |
| WO | 2011/088192 A1 | 7/2011 |
| WO | 2011088181 A1 | 7/2011 |
| WO | WO 2011088181 A1 * | 7/2011 |
| WO | 2012/011592 A1 | 1/2012 |
| WO | 2013/066831 A1 | 5/2013 |
| WO | 2013/066833 A1 | 5/2013 |
| WO | 2013/066834 A1 | 5/2013 |
| WO | 2013/066835 A1 | 5/2013 |
| WO | 2013/066836 A1 | 5/2013 |
| WO | 2013/066839 A1 | 5/2013 |
| WO | WO 2013066835 A2 * | 5/2013 |

OTHER PUBLICATIONS

CAS Registry No. 1333646-57-3, which entered STN on Sep. 29, 2011.*
CAS Registry No. 1333843-22-3, which entered STN on Sep. 29, 2011.*
Mihaylova et al., Cell, 145(4):607-621 (2011).
Moresi et al., Cell, 143(1):35-45 (2010).
Liu Gang et al: "Discovery of Potent, Selective, Orally Bioavailable Stearoyl-CoA Desature 1 Inbibitors", J Med Chem 2007, 50 (13): 3086-3100.

* cited by examiner

*Primary Examiner* — Joseph Kosack
*Assistant Examiner* — Matthew Coughlin
(74) *Attorney, Agent, or Firm* — Laura Madden

(57) ABSTRACT

The invention relates to novel trifluoromethyl-oxadiazole derivatives of formula (I), and pharmaceutically acceptable salts thereof, (I) in which all of the variables are as defined in the specification, pharmaceutical compositions thereof, pharmaceutical combinations thereof, and their use as medicaments, particularly for the treatment of neurodegeneration, muscle atrophy or metabolic syndrome via inhibition of HDAC4.

17 Claims, No Drawings

TRIFLUOROMETHYL-OXADIAZOLE DERIVATIVES AND THEIR USE IN THE TREATMENT OF DISEASE

This application is a U.S. National Phase filing of International Application No. PCT/IB2012/053470 filed 6 Jul. 2012, which claims priority to U.S. application Ser. No. 61/505,592 filed 8 Jul. 2011.

FIELD OF THE INVENTION

The invention relates to novel trifluoromethyl-oxadiazole derivatives and pharmaceutically acceptable salts thereof, pharmaceutical compositions thereof, pharmaceutical combinations thereof, and their use as medicaments, particularly for the treatment of neurodegeneration, muscle atrophy or metabolic syndrome via inhibition of HDAC4.

BACKGROUND OF THE INVENTION

Huntington's disease (HD) is an autosomal dominant neurodegenerative disease with an incidence of 1 in 10'000 (approx. 30'000 patients in USA). HD is not prevalent to any particular population, race or ethnic group, and both genders are affected. HD manifests in middle age (30-50 years) with jerking, uncontrollable movement of the limbs, trunk and face followed by progressive loss of mental abilities and development of psychiatric problems. The disease continues without remission over 10 to 25 years and is ultimately terminal.

The cause of the disease is an expansion of CAG repeats in exon 1 of the gene coding for the protein huntingtin. This expansion produces a mutated protein (mHTT) with a polyglutamine repeat within the amino terminus. mHTT and its proteolytic N-terminal fragments accumulate in intracellular aggregates and have been shown to interfere with the transcriptional machinery of the cell.

Transcriptional dysregulation is the first detectable change in HD and it is observed in both human and animal correlates of disease. Modulation of transcriptional activity can be achieved via the inhibition of histone deacetylase enzymes a family of 11 isotypes further classified into sub-families: HDAC1,2,3,8 (Class I); HDAC4,5,7,9 (Class IIa), HDAC6, 10 (Class IIb) and HDAC11 (Class IV). HDAC inhibition can restore the balance and a pan-HDAC inhibitor (SAHA) has been found efficacious in *Drosophila* and mouse assays for Huntington's pathology (Hockly et al., PNAS (2003) 100: 2041; Kazantsev A G, Thompson L M., Nat Rev Drug Discov. (2008) 7:854-68). As SAHA is a non-selective inhibitor of all HDACs Class I, IIa+IIb and IV sub-families it is not possible to determine through which isotype/sub-family the beneficial effects are mediated.

Recently the individual role of members of the Class IIa sub-family (HDAC4,5,7,9) was investigated by knocking-down the respective isotypes by genetic crossing with the R6/2 mouse, a genetically engineered mouse mimicking the human HD pathology (Mielcarek M. et al., J. Neurology, Neurosurgery and Psychiatry (2009) 79:A8). The resulting double transgenic mice strains for which HDAC 5, HDAC 7 or HDAC 9 were knocked-down did not show any improvement of the R6/2 phenotype whereas the reduction in HDAC4 expression levels improved the motor impairment phenotype of the R6/2 mice.

HDAC4 inhibition therefore provides a potential opportunity for pharmaceutical intervention and treatment of Huntington's disease.

Class IIa HDACs are also expressed in skeletal muscle and are expressed at a lower level in slow-twitching muscle compared to fast-twitching muscle. Deletion of any combination of four alleles of HDAC4, 5 and 9 leads to more slow-fiber gene expression, which in turn leads to enhanced running endurance (Potthoff et al., J. Clin. Invest. (2007) 117, 2459-2467). Furthermore, HDAC4 gene expression is highly upregulated in muscle after denervation/casting/hindlimb suspension (Bodine et al., Science (2001) 294, 1704-1708; Cohen et al. JBC (2007) 282(46):33752-9). HDAC4 inhibits the expression of FGFBP1, which interacts with FGF7/10/22 and promotes reinnervation (Williams et al., Science (2009) 326, 1549-1554). Upon denervation, increased HDAC4 expression also represses the expression of Dach2, which in turn leads to increased expression of myogenin. Myogenin upregulates the expression of the two E3 ubiquitin ligases that are required for muscle atrophy. Denervated mice lacking HDAC4 (muscle specific knockout) or HDAC5 demonstrated a 30% loss in muscle weight compared to the 50% loss of muscle mass in WT mice, while mice lacking both HDAC4 and HDAC5 demonstrated only a 10% decrease in muscle weight (Moresi et al., Cell (2010) 143, 35-45).

Inhibition of HDAC4 thus also provides a potential method for treating muscle atrophy.

In addition, a very recent publication has shown a pivotal role for HDAC Class IIa in the regulation of glucose homeostasis (Mihaylova M M, et al., Cell (2011) 145, 607-21). In a mouse model for hyperglycemia (ob/ob mouse) reduction of Class IIa HDACs using shRNAs against HDAC4, 5 and 7 has been shown to lower blood glucose and increase glycogen storage. Furthermore, reduction of Class IIa HDACs in a mouse model for type 2 diabetes (high fat diet mouse) significantly improves hyperglycemia.

Use of a pharmacological agent to reduce the activity of HDAC4 may therefore also provide a useful therapeutic intervention for the treatment of diabetes/metabolic syndrome.

Class I HDACs can de-acetylate histones and other transcription factors. Inhibition of class I HDACs can lead to inhibition of proliferation, induce terminal cell differentiation and/or apoptosis, and induction or repression of gene expression in cells. Class I HDAC inhibitors would therefore be of most use in cancer therapy (Davie J R, J Nutr (2003 July) 133 (7 Suppl), 2485S-2493S). In contrast, class II HDACs do not target histones. It would therefore be advantageous to provide Class IIa-selective HDAC4 inhibitors for the treatment of Huntington's disease, muscle atrophy or diabetes/metabolic syndrome which have low inhibitory activity against Class I HDACs.

The present invention thus relates to novel trifluoromethyl-oxadiazole derivatives having Class IIa-selective HDAC4 inhibitory activity and their medical use, particularly in the treatment of Huntington's disease, muscle atrophy and diabetes/metabolic syndrome.

SUMMARY OF THE INVENTION

In a first aspect of the invention, there is therefore provided a compound of formula (I), or a pharmaceutically acceptable salt thereof,

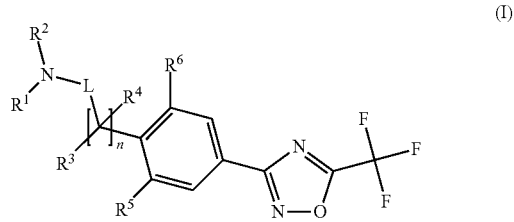

wherein

L represents —C(=O)— or —S(=O)$_m$— and m represents 1 or 2;

either

R$^1$ represents C$_{1-6}$alkyl, C$_{2-6}$alkenyl, C$_{2-6}$alkynyl, halogenC$_{1-6}$alkyl, C$_{1-6}$alkoxy, C$_{1-6}$alkoxyC$_{1-6}$alkyl, C$_{1-6}$alkylcarbonylC$_{1-6}$alkyl, C$_{1-6}$alkoxycarbonylC$_{1-6}$alkyl, hydroxyC$_{1-6}$alkyl, aminoC$_{1-6}$alkyl, C$_{1-4}$alkylaminoC$_{1-6}$alkyl, diC$_{1-4}$alkylaminoC$_{1-6}$alkyl, aminocarbonylC$_{1-6}$alkyl, C$_{1-4}$alkylaminocarbonylC$_{1-6}$alkyl, diC$_{1-4}$alkylaminocarbonylC$_{1-6}$alkyl, C$_{3-8}$cycloalkylC$_{0-6}$alkyl, phenylC$_{0-6}$alkyl, phenylC$_{0-6}$alkylaminoC$_{1-6}$alkyl, phenylC$_{0-6}$alkylamino(C$_{1-4}$alkyl)C$_{1-6}$alkyl, heteroarylC$_{0-6}$alkyl wherein the heteroaryl moiety is a 5- or 6-membered aromatic ring which comprises 1, 2, 3 or 4 heteroatoms individually selected from N, O and S, heterocyclylC$_{0-6}$alkyl wherein the heterocyclyl moiety is a 5- or 6-membered non-aromatic ring which comprises 1, 2 or 3 heteroatoms individually selected from N, O and S, or —CR$^7$R$^8$ wherein R$^7$ represents phenylC$_{0-5}$alkyl and R$^8$ represents diC$_{1-2}$alkylaminoC$_{1-4}$alkyl, and wherein any of said cycloalkyl, phenyl, heteroaryl and heterocyclyl moieties are optionally substituted by 1, 2, 3, 4 or 5 substituents, which may be the same or different, selected from R$^9$, R$^2$ represents hydrogen or C$_{1-4}$alkyl, or R$^1$ and R$^2$, together with the nitrogen atom to which they are attached, form a 5- or 6-membered non-aromatic heterocyclic ring which optionally comprises one additional heteroatom ring member selected from N and O and wherein said heterocyclic ring is optionally substituted by 1, 2, 3, 4 or 5 substituents, which may be the same or different, selected from R$^9$;

R$^3$ and R$^4$ independently represent hydrogen or methyl;

n represents 0 or 1;

R$^5$ and R$^6$ independently represent hydrogen, halogen, methyl or methoxy;

R$^9$ represents cyano, amino, halogen, hydroxy, C$_{1-4}$alkyl, C$_{2-4}$alkenyl, C$_{2-4}$alkynyl, halogenC$_{1-4}$alkyl, C$_{1-4}$alkoxy, C$_{1-4}$alkylamino, diC$_{1-4}$alkylamino, C$_{1-4}$alkylcarbonyl, C$_{1-4}$alkoxycarbonyl, aminocarbonyl, C$_{1-4}$alkylaminocarbonyl, diC$_{1-4}$alkylaminocarbonyl, C$_{1-4}$alkoxycarbonylamino, C$_{3-8}$cycloalkylC$_{0-6}$alkyl, phenylC$_{0-6}$alkyl, heteroarylC$_{0-6}$alkyl wherein the heteroaryl moiety is a 5- or 6-membered aromatic ring which comprises 1, 2, 3 or 4 heteroatoms individually selected from N, O and S, heterocyclylC$_{0-6}$alkyl wherein the heterocyclyl moiety is a 5- or 6-membered non-aromatic ring which comprises 1, 2 or 3 heteroatoms individually selected from N, O and S, and wherein any of said cycloalkyl, phenyl, heteroaryl and heterocyclyl moieties are optionally substituted by 1, 2, 3, 4 or 5 substituents, which may be the same or different, selected from R$^{10}$; and R$^{10}$ represents methyl, methoxy or halogen.

In a second aspect of the invention, there is therefore provided a compound of formula (I), or a pharmaceutically acceptable salt thereof,

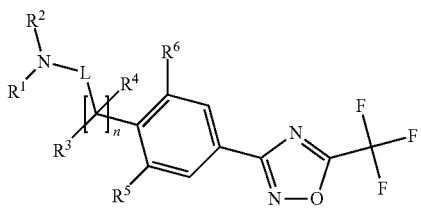

(I)

wherein

L represents —C(=O)— or —S(=O)$_m$— and m represents 1 or 2;

either

R$^1$ represents C$_{1-6}$alkyl, C$_{2-6}$alkenyl, C$_{2-6}$alkynyl, halogenC$_{1-6}$alkyl, C$_{1-6}$alkoxy, C$_{1-6}$alkoxyC$_{1-6}$alkyl, C$_{1-6}$alkylcarbonylC$_{1-6}$alkyl, C$_{1-6}$alkoxycarbonylC$_{1-6}$alkyl, hydroxyC$_{1-6}$alkyl, aminoC$_{1-6}$alkyl, C$_{1-4}$alkylaminoC$_{1-6}$alkyl, diC$_{1-4}$alkylaminoC$_{1-6}$alkyl, aminocarbonylC$_{1-6}$alkyl, C$_{1-4}$alkylaminocarbonylC$_{1-6}$alkyl, diC$_{1-4}$alkylaminocarbonylC$_{1-6}$alkyl, C$_{3-8}$cycloalkylC$_{0-6}$alkyl, phenylC$_{0-6}$alkyl, heteroarylC$_{0-6}$alkyl wherein the heteroaryl moiety is a 5- or 6-membered aromatic ring which comprises 1, 2, 3 or 4 heteroatoms individually selected from N, O and S, heterocyclylC$_{0-6}$alkyl wherein the heterocyclyl moiety is a 5- or 6-membered non-aromatic ring which comprises 1, 2 or 3 heteroatoms individually selected from N, O and S, or —CR$^7$R$^8$ wherein R$^7$ represents phenylC$_{0-5}$alkyl and R$^8$ represents diC$_{1-2}$alkylaminoC$_{1-4}$alkyl, and wherein any of said cycloalkyl, phenyl, heteroaryl and heterocyclyl moieties are optionally substituted by 1, 2, 3, 4 or 5 substituents, which may be the same or different, selected from R$^9$, R$^2$ represents hydrogen or methyl, or R$^1$ and R$^2$, together with the nitrogen atom to which they are attached, form a 5- or 6-membered non-aromatic heterocyclic ring which optionally comprises one additional heteroatom ring member selected from N and O and wherein said heterocyclic ring is optionally substituted by 1, 2, 3, 4 or 5 substituents, which may be the same or different, selected from R$^9$;

R$^3$ and R$^4$ independently represent hydrogen or methyl;

n represents 0 or 1;

R$^5$ and R$^6$ independently represent hydrogen, halogen, methyl or methoxy;

R$^9$ represents cyano, amino, halogen, hydroxy, C$_{1-4}$alkyl, C$_{2-4}$alkenyl, C$_{2-4}$alkynyl, halogenC$_{1-4}$alkyl, C$_{1-4}$alkoxy, C$_{1-4}$alkylamino, diC$_{1-4}$alkylamino, C$_{1-4}$alkylcarbonyl, C$_{1-4}$alkoxycarbonyl, aminocarbonyl, C$_{1-4}$alkylaminocarbonyl, diC$_{1-4}$alkylaminocarbonyl, C$_{1-4}$alkoxycarbonylamino, C$_{3-8}$cycloalkylC$_{0-6}$alkyl, phenylC$_{0-6}$alkyl, heteroarylC$_{0-6}$alkyl wherein the heteroaryl moiety is a 5- or 6-membered aromatic ring which comprises 1, 2, 3 or 4 heteroatoms individually selected from N, O and S, heterocyclylC$_{0-6}$alkyl wherein the heterocyclyl moiety is a 5- or 6-membered non-aromatic ring which comprises 1, 2 or 3 heteroatoms individually selected from N, O and S, and wherein any of said cycloalkyl, phenyl, heteroaryl and heterocyclyl moieties are optionally substituted by 1, 2, 3, 4 or 5 substituents, which may be the same or different, selected from R$^{10}$; and R$^{10}$ represents methyl, methoxy or halogen.

Definitions

As used herein, the term "C$_{1-6}$alkyl" refers to a straight or branched hydrocarbon chain radical consisting solely of carbon and hydrogen atoms, containing no unsaturation, having from one to six carbon atoms, and which is attached to the rest of the molecule by a single bond. The term "C$_{1-4}$alkyl" is to be construed accordingly. Examples of C$_{1-6}$alkyl include, but are not limited to, methyl, (R)-methyl, ethyl, n-propyl, 1-methylethyl (iso-propyl), n-butyl, n-pentyl and 1,1-dimethylethyl (t-butyl).

As used herein, the term "C$_{2-6}$alkenyl" refers to a straight or branched hydrocarbon chain radical group consisting solely of carbon and hydrogen atoms, containing at least one double bond, having from two to six carbon atoms, which is attached to the rest of the molecule by a single bond. The term "C$_{2-4}$alkenyl" is to be construed accordingly. Examples of $C_{2-6}$alkenyl include, but are not limited to, ethenyl, prop-1-enyl, but-1-enyl, pent-1-enyl and penta-1,4-dienyl.

As used herein, the term "$C_{2-6}$alkynyl" refers to a straight or branched hydrocarbon chain radical group consisting solely of carbon and hydrogen atoms, containing at least one triple bond, having from two to six carbon atoms, and which is attached to the rest of the molecule by a single bond. The term "$C_{2-4}$alkynyl" is to be construed accordingly. Examples of $C_{2-6}$alkynyl include, but are not limited to, ethynyl, prop-1-ynyl, but-1-ynyl, pent-1-ynyl and penta-1,4-diynyl.

As used herein, the term "$C_{1-16}$alkoxy" refers to a radical of the formula —$OR_a$ where $R_a$ is a $C_{1-6}$alkyl radical as generally defined above. Examples of $C_{1-6}$alkoxy include, but are not limited to, methoxy, ethoxy, propoxy, isopropoxy, butoxy, isobutoxy, pentoxy, and hexoxy.

As used herein, the term "$C_{1-6}$alkoxy$C_{1-6}$alkyl" refers to a radical of the formula —$R_a$—O—$R_a$ where each $R_a$ is independently a $C_{1-6}$alkyl radical as defined above. The oxygen atom may be bonded to any carbon atom in either alkyl radical. Examples of $C_{1-6}$alkoxy $C_{1-6}$alkyl include, but are not limited to, methoxy-methyl, methoxy-ethyl, ethoxy-ethyl, 1-ethoxy-propyl and 2-methoxy-butyl.

As used herein, the term "$C_{1-4}$alkylcarbonyl" refers to a radical of the formula —C(=O)—$R_a$ where $R_a$ is a $C_{1-4}$alkyl radical as defined above.

As used herein, the term "$C_{1-6}$alkylcarbonyl$C_{1-6}$alkyl" refers to a radical of the formula —$R_a$—C(=O)—$R_a$ where each $R_a$ is independently a $C_{1-6}$alkyl radical as defined above. The carbon atom of the carbonyl group may be bonded to any carbon atom in either alkyl radical.

As used herein, the term "$C_{1-6}$alkoxycarbonyl" refers to a radical of the formula —C(=O)—O—$R_a$ where $R_a$ is a $C_{1-6}$alkyl radical as defined above.

As used herein, the term "$C_{1-6}$alkoxycarbonyl$C_{1-16}$alkyl" refers to a radical of the formula —$R_a$—C(=O)—O—$R_a$ where each $R_a$ is independently a $C_{1-6}$alkyl radical as defined above.

As used herein, the term "$C_{1-4}$alkoxycarbonylamino" refers to a radical of the formula —NH—C(=O)—O—$R_a$ where $R_a$ is a $C_{1-4}$alkyl radical as defined above.

As used herein, the term "hydroxy$C_{1-6}$alkyl" refers to a $C_{1-6}$alkyl radical as defined above, wherein one of the hydrogen atoms of the $C_{1-6}$alkyl radical is replaced by OH. Examples of hydroxy$C_{1-6}$alkyl include, but are not limited to, hydroxy-methyl, 2-hydroxy-ethyl, 2-hydroxy-propyl, 3-hydroxy-propyl and 5-hydroxy-pentyl.

As used herein, the term "amino$C_{1-6}$alkyl" refers to a $C_{1-6}$alkyl radical as defined above, wherein one of the hydrogen atoms of the $C_{1-6}$alkyl group is replaced by a primary amino group. Representative examples of amino$C_{1-6}$alkyl include, but are not limited to, amino-methyl, 2-amino-ethyl, 2-amino-propyl, 3-amino-propyl, 3-amino-pentyl and 5-amino-pentyl.

As used herein, the term "$C_{1-4}$alkylamino" refers to a radical of the formula —NH—$R_a$ where $R_a$ is a $C_{1-4}$alkyl radical as defined above.

As used herein, the term "$C_{1-4}$alkylamino$C_{1-6}$alkyl" refers to a radical of the formula —$R_{a1}$—NH—$R_{a2}$ where $R_{a1}$ is a $C_{1-6}$alkyl radical as defined above and $R_{a2}$ is a $C_{1-4}$alkyl radical as defined above. The nitrogen atom may be bonded to any carbon atom in either alkyl radical.

As used herein, the term "di$C_{1-4}$alkylamino" refers to a radical of the formula —N($R_a$)—$R_a$ where each $R_a$ is a $C_{1-4}$alkyl radical, which may be the same or different, as defined above.

As used herein, the term "di$C_{1-4}$alkylamino$C_{1-6}$alkyl" refers to a radical of the formula —$R_{a1}$—N($R_{a2}$)—$R_{a2}$ where $R_{a1}$ is a $C_{1-6}$alkyl radical as defined above and each $R_{a2}$ is a $C_{1-4}$alkyl radical, which may be the same or different, as defined above. The nitrogen atom may be bonded to any carbon atom in any alkyl radical.

As used herein, the term "aminocarbonyl" refers to a radical of the formula —C(=O)—$NH_2$.

As used herein, the term "aminocarbonyl$C_{1-6}$alkyl" refers to a radical of the formula —$R_a$—C(=O)—$NH_2$ where $R_a$ is a $C_{1-6}$alkyl radical as defined above.

As used herein, the term "$C_{1-4}$alkylaminocarbonyl" refers to a radical of the formula —C(=O)—NH—$R_a$ where $R_a$ is a $C_{1-4}$alkyl radical as defined above.

As used herein, the term "$C_{1-4}$alkylaminocarbonyl$C_{1-6}$alkyl" refers to a radical of the formula —$R_{a1}$—C(=O)—NH—$R_{a2}$ where $R_{a1}$ is a $C_{1-6}$alkyl radical as defined above and $R_{a2}$ is a $C_{1-4}$alkyl radical as defined above.

As used herein, the term "di$C_{1-4}$alkylaminocarbonyl" refers to a radical of the formula —C(=O)—N($R_a$)—$R_a$ where each $R_a$ is a $C_{1-4}$alkyl radical, which may be the same or different, as defined above.

As used herein, the term "di$C_{1-4}$alkylaminocarbonyl$C_{1-6}$alkyl" refers to a radical of the formula —$R_{a1}$—C(=O)—N($R_{a2}$)—$R_{a2}$ where $R_{a1}$ is a $C_{1-6}$alkyl radical as defined above and each $R_{a2}$ is a $C_{1-4}$alkyl radical, which may be the same or different, as defined above.

As used herein, the term "$C_{3-8}$cycloalkyl$C_{0-6}$alkyl" refers to a stable non-aromatic monocyclic hydrocarbon radical consisting solely of carbon and hydrogen atoms, having from three to eight carbon atoms, and which is saturated or unsaturated and attached to the rest of the molecule by a single bond or by a $C_{1-6}$alkyl radical as defined above. Examples of $C_{3-8}$cycloalkyl$C_{0-6}$alkyl include, but are not limited to, cyclopropyl, cyclopropyl-methyl, cyclobutyl, cyclobutyl-ethyl, cyclopentyl, cyclopentyl-propyl, cyclohexyl, cyclohepty and cyclooctyl.

As used herein, the term "phenyl$C_{0-6}$alkyl" refers to a phenyl ring attached to the rest of the molecule by a single bond or by a $C_{1-6}$alkyl radical as defined above. Examples of phenyl$C_{0-6}$alkyl include, but are not limited to, phenyl and benzyl.

As used herein, the term "phenyl$C_{0-6}$alkylamino$C_{1-6}$alkyl" refers to a radical of the formula —$R_a$—NH—$R_b$ where $R_a$ is a $C_{1-6}$alkyl radical as defined above and $R_b$ is a phenyl$C_{0-6}$alkyl radical as defined above.

As used herein, the term "phenyl$C_{0-6}$alkylamino($C_{1-4}$alkyl)$C_{1-6}$alkyl" refers to a radical of the formula —$R_{a1}$—N($R_{a2}$)—$R_b$ where $R_{a1}$ is a $C_{1-6}$alkyl radical as defined above, $R_{a2}$ is a $C_{1-4}$alkyl radical as defined above and $R_b$ is a phenyl$C_{0-6}$alkyl radical as defined above.

"Halogen" refers to bromo, chloro, fluoro or iodo.

As used herein, the term "halogen$C_{1-6}$alkyl" refers to $C_{1-6}$alkyl radical, as defined above, substituted by one or more halo radicals, as defined above. Examples of halogen$C_{1-6}$alkyl include, but are not limited to, trifluoromethyl, difluoromethyl, fluoromethyl, trichloromethyl, 2,2,2-trifluoroethyl, 1-fluoromethyl-2-fluoroethyl, 3-bromo-2-fluoropropyl and 1-bromomethyl-2-bromoethyl.

As used herein, the term "heterocyclyl" or "heterocyclic" refers to a stable 5- or 6-membered non-aromatic monocyclic ring radical which comprises 1, 2, or 3, heteroatoms individually selected from nitrogen, oxygen and sulfur. The heterocyclyl radical may be bonded via a carbon atom or heteroatom. Examples of heterocyclyl include, but are not limited to, azetidinyl, oxetanyl, pyrrolinyl, pyrrolidyl, tetrahydrofuryl, tetrahydrothienyl, piperidyl, piperazinyl, tetrahydropyranyl, morpholinyl or perhydroazepinyl.

As used herein, the term "heterocyclylC$_{0-6}$alkyl" refers to a heterocyclic ring as defined above which is attached to the rest of the molecule by a single bond or by a C$_{1-6}$alkyl radical as defined above.

As used herein, the term "heteroaryl" refers to a 5- or 6-membered aromatic monocyclic ring radical which comprises 1, 2, 3 or 4 heteroatoms individually selected from nitrogen, oxygen and sulfur. The heteroaryl radical may be bonded via a carbon atom or heteroatom. Examples of heteroaryl include, but are not limited to, furyl, pyrrolyl, thienyl, pyrazolyl, imidazolyl, thiazolyl, isothiazolyl, oxazolyl, isoxazolyl, triazolyl, tetrazolyl, pyrazinyl, pyridazinyl, pyrimidyl or pyridyl.

As used herein, the term "heteroarylC$_{0-6}$alkyl" refers to a heteroaryl ring as defined above which is attached to the rest of the molecule by a single bond or by a C$_{1-6}$alkyl radical as defined above.

As used herein, the term "a," "an," "the" and similar terms used in the context of the present invention (especially in the context of the claims) are to be construed to cover both the singular and plural unless otherwise indicated herein or clearly contradicted by the context. The use of any and all examples, or exemplary language (e.g. "such as") provided herein is intended merely to better illuminate the invention and does not pose a limitation on the scope of the invention otherwise claimed.

The term "compounds of the present invention" (unless specifically identified otherwise) refer to compounds of formula (I) or (Ia), compounds of the Examples, pharmaceutically acceptable salts of such compounds, and/or hydrates or solvates of such compounds, as well as, all stereoisomers (including diastereoisomers and enantiomers), tautomers and isotopically labeled compounds (including deuterium). The term "agents of the invention" is intended to have the same meaning as "compounds of the present invention".

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "metabolic syndrome" is a recognized clinical term used to describe a condition comprising combinations of Type II diabetes, impaired glucose tolerance, insulin resistance, hypertension, obesity, increased abdominal girth, hypertriglyceridemia, low HDL, hyperuricaernia, hypercoagulability and/or microalbuminemia. The American Heart Association has published guidelines for the diagnosis of metabolic syndrome, Grundy, S., et. al., (2006) Cardiol. Rev. Vol. 13, No. 6, pp. 322-327.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

As used herein, the term "prevention" of any particular disease or disorder refers to the administration of a compound of the invention to a subject before any symptoms of that disease or disorder are apparent.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, a subject is "in need of" a treatment if such subject would benefit biologically, medically or in quality of life from such treatment.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by HDAC4 or (ii) associated with HDAC4 activity, or (iii) characterized by activity (normal or abnormal) of HDAC4; or (2) reducing or inhibiting the activity of HDAC4. In another non-limiting embodiment, the term "a therapeutically effective amount" refers to the amount of the compound of the present invention that, when administered to a cell, or a tissue, or a non-cellular biological material, or a medium, is effective to at least partially reduce or inhibit the activity of HDAC4. The meaning of the term "a therapeutically effective amount" as illustrated in the above embodiments for HDAC4 also applies by the same means to any other relevant proteins/peptides/enzymes, such as one of the other members of the histone deacetylase enzyme family.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both.

DETAILED DESCRIPTION OF THE INVENTION

The present invention provides compounds and pharmaceutical compositions thereof that may be useful in the treatment or prevention of diseases, conditions and/or disorders modulated by the inhibition of HDAC4.

Embodiment 1: a compound of formula (I), or a pharmaceutically acceptable salt thereof, as defined above in the first aspect of the invention.

Embodiment 2: a compound of formula (I), or a pharmaceutically acceptable salt thereof, as defined above in the second aspect of the invention.

Embodiment 3: a compound according to Embodiment 1 or Embodiment 2, or a pharmaceutically acceptable salt thereof, wherein L represents —C(=O)—.

Embodiment 4: a compound according to Embodiment 1 or Embodiment 2, or a pharmaceutically acceptable salt thereof, wherein L represents —S(=O)$_2$—.

Embodiment 5: a compound according to any one of Embodiments 1, 3 or 4, or a pharmaceutically acceptable salt thereof, wherein $R^1$ represents $C_{1-6}$alkyl, $C_{2-6}$alkenyl, $C_{2-6}$alkynyl, halogen$C_{1-6}$alkyl, $C_{1-6}$alkoxy, $C_{1-6}$alkoxy$C_{1-6}$alkyl, $C_{1-6}$alkylcarbonyl$C_{1-6}$alkyl, $C_{1-6}$alkoxycarbonyl$C_{1-6}$alkyl, hydroxy$C_{1-6}$alkyl, amino$C_{1-6}$alkyl, $C_{1-4}$alkylamino$C_{1-6}$alkyl, di$C_{1-4}$alkylamino$C_{1-6}$alkyl, aminocarbonyl$C_{1-6}$alkyl, $C_{1-4}$alkylaminocarbonyl$C_{1-6}$alkyl, di$C_{1-4}$alkylaminocarbonyl$C_{1-6}$alkyl, $C_{3-8}$cycloalkyl$C_{0-6}$alkyl, phenyl$C_{0-6}$alkyl, heteroaryl$C_{0-6}$alkyl wherein the heteroaryl moiety is a 5- or 6-membered aromatic ring which comprises 1, 2, 3 or 4 heteroatoms individually selected from N, O and S, heterocyclyl$C_{0-6}$alkyl wherein the heterocyclyl moiety is a 5- or 6-membered non-aromatic ring which comprises 1, 2 or 3 heteroatoms individually selected from N, O and S, or —$CR^7R^8$ wherein $R^7$ represents phenyl$C_{0-5}$alkyl and $R^8$ represents di$C_{1-2}$alkylamino$C_{1-4}$alkyl, and wherein any of said cycloalkyl, phenyl, heteroaryl and heterocyclyl moieties are optionally substituted by 1, 2, 3, 4 or 5 substituents, which may be the same or different, selected from $R^9$.

Embodiment 6: a compound according to any one of Embodiments 1 to 4, or a pharmaceutically acceptable salt thereof, wherein $R^1$ represents $C_{1-6}$alkyl, $C_{2-6}$alkenyl, $C_{2-6}$alkynyl, halogen$C_{1-6}$alkyl, $C_{1-6}$alkoxy, $C_{1-6}$alkoxy$C_{1-6}$alkyl, $C_{1-6}$alkylcarbonyl$C_{1-6}$alkyl, $C_{1-6}$alkoxycarbonyl$C_{1-6}$alkyl, hydroxy$C_{1-6}$alkyl, amino$C_{1-6}$alkyl, $C_{1-4}$alkylamino$C_{1-6}$alkyl, di$C_{1-4}$alkylamino$C_{1-6}$alkyl, aminocarbonyl$C_{1-6}$alkyl, $C_{1-4}$alkylaminocarbonyl$C_{1-6}$alkyl or di$C_{1-4}$alkylaminocarbonyl$C_{1-6}$alkyl.

Embodiment 7: a compound according to any one of Embodiments 1 to 4, or a pharmaceutically acceptable salt thereof, wherein $R^1$ represents $C_{1-4}$alkylamino$C_{1-6}$alkyl or di$C_{1-4}$alkylamino$C_{1-6}$alkyl.

Embodiment 8: a compound according to any one of Embodiments 1 to 4, or a pharmaceutically acceptable salt thereof, wherein $R^1$ represents —$CR^7R^8$ wherein $R^7$ represents phenyl$C_{0-5}$alkyl and $R^8$ represents di$C_{1-2}$alkylamino$C_{1-4}$alkyl, and wherein said phenyl is optionally substituted by 1, 2 or 3 substituents, which may be the same or different, selected from $R^9$.

Embodiment 9: a compound according to any one of Embodiments 1 to 4, or a pharmaceutically acceptable salt thereof, wherein $R^1$ represents $C_{3-8}$cycloalkyl$C_{0-6}$alkyl, phenyl$C_{0-6}$alkyl, heteroaryl$C_{0-6}$alkyl wherein the heteroaryl moiety is a 5- or 6-membered aromatic ring which comprises 1, 2, 3 or 4 heteroatoms individually selected from N, O and S, heterocyclyl$C_{0-6}$alkyl wherein the heterocyclyl moiety is a 5- or 6-membered non-aromatic ring which comprises 1, 2 or 3 heteroatoms individually selected from N, O and S, or —$CR^7R^8$ wherein $R^7$ represents phenyl$C_{0-5}$alkyl and $R^8$ represents di$C_{1-2}$alkylamino$C_{1-4}$alkyl, and wherein any of said cycloalkyl, phenyl, heteroaryl and heterocyclyl moieties are optionally substituted by 1, 2, 3, 4 or 5 substituents, which may be the same or different, selected from $R^9$.

Embodiment 10: a compound according to any one of Embodiments 1 to 4, or a pharmaceutically acceptable salt thereof, wherein $R^1$ and $R^2$, together with the nitrogen atom to which they are attached, form a 5- or 6-membered non-aromatic heterocyclic ring which optionally comprises one additional heteroatom ring member selected from N and O and wherein said heterocyclic ring is optionally substituted by 1, 2, 3, 4 or 5 substituents, which may be the same or different, selected from $R^9$.

Embodiment 11: a compound according to any one of Embodiments 1 to 9, or a pharmaceutically acceptable salt thereof, wherein $R^2$ represents hydrogen.

Embodiment 12: a compound according to any one of Embodiments 1 to 9, or a pharmaceutically acceptable salt thereof, wherein $R^2$ represents methyl.

Embodiment 13: a compound according to any one of Embodiments 5 or 8 to 10, or a pharmaceutically acceptable salt thereof, wherein $R^9$ represents cyano, amino, halogen, hydroxy, $C_{1-4}$alkyl, $C_{2-4}$alkenyl, $C_{2-4}$alkynyl, halogen$C_{1-4}$alkyl, $C_{1-4}$alkoxy, $C_{1-4}$alkylamino, di$C_{1-4}$alkylamino, $C_{1-4}$alkylcarbonyl, $C_{1-4}$alkoxycarbonyl, aminocarbonyl, $C_{1-4}$alkylaminocarbonyl, di$C_{1-4}$alkylaminocarbonyl or $C_{1-4}$alkoxycarbonylamino.

Embodiment 14: a compound according to any one of Embodiments 5 or 8 to 10, or a pharmaceutically acceptable salt thereof, wherein $R^9$ represents cyano, amino, fluoro, chloro, hydroxy, methyl or methoxy.

Embodiment 15: a compound according to any one of Embodiments 5 or 8 to 10, or a pharmaceutically acceptable salt thereof, wherein $R^9$ represents $C_{3-8}$cycloalkyl$C_{0-6}$alkyl, phenyl$C_{0-6}$alkyl, heteroaryl$C_{0-6}$alkyl wherein the heteroaryl moiety is a 5- or 6-membered aromatic ring which comprises 1, 2, 3 or 4 heteroatoms individually selected from N, O and S, heterocyclyl$C_{0-6}$alkyl wherein the heterocyclyl moiety is a 5- or 6-membered non-aromatic ring which comprises 1, 2 or 3 heteroatoms individually selected from N, O and S, and wherein any of said cycloalkyl, phenyl, heteroaryl and heterocyclyl moieties are optionally substituted by 1, 2, 3, 4 or 5 substituents, which may be the same or different, selected from $R^{10}$.

Embodiment 16: a compound according to any one of Embodiments 1 to 15, or a pharmaceutically acceptable salt thereof, wherein n represents 1 and $R^3$ and $R^4$ both represent hydrogen.

Embodiment 17: a compound according to any one of Embodiments 1 to 15, or a pharmaceutically acceptable salt thereof, wherein n represents 0.

Embodiment 18: a compound according to any one of Embodiments 1 to 17, or a pharmaceutically acceptable salt thereof, wherein $R^5$ and $R^6$ individually represent hydrogen, fluoro or chloro.

Embodiment 19: a compound according to any one of Embodiments 1 to 17, or a pharmaceutically acceptable salt thereof, wherein $R^5$ and $R^6$ individually represent hydrogen or fluoro.

Embodiment 20: a compound according to any one of Embodiments 1 to 17, or a pharmaceutically acceptable salt thereof, wherein one of $R^5$ and $R^6$ represents fluoro and the other represents hydrogen.

Embodiment 21: a compound according to any one of Embodiments 1 to 17, or a pharmaceutically acceptable salt thereof, wherein $R^5$ and $R^6$ both represent fluoro.

Embodiment 22: a compound according to any one of Embodiments 1 to 17, or a pharmaceutically acceptable salt thereof, wherein one of $R^5$ and $R^6$ represents chloro and the other represents hydrogen.

Embodiment 23: a compound according to any one of Embodiments 1 to 17, or a pharmaceutically acceptable salt thereof, wherein $R^5$ and $R^6$ both represent hydrogen.

Embodiment 24: a compound according to Embodiment 1 or Embodiment 2 of formula (Ia), or a pharmaceutically acceptable salt thereof,

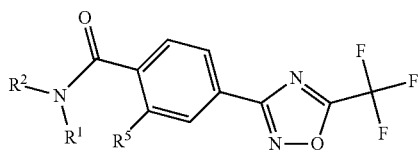

(Ia)

wherein
R¹ represents $C_{1-6}$alkyl, $C_{2-6}$alkenyl, $C_{2-6}$alkynyl, halogen$C_{1-6}$alkyl, $C_{1-6}$alkoxy, $C_{1-6}$alkoxy$C_{1-6}$alkyl, $C_{1-6}$alkylcarbonyl$C_{1-6}$alkyl, $C_{1-6}$alkoxycarbonyl$C_{1-6}$alkyl, hydroxy$C_{1-6}$alkyl, amino$C_{1-6}$alkyl, $C_{1-4}$alkylamino-$C_{1-6}$alkyl, di$C_{1-4}$alkylamino$C_{1-6}$alkyl, aminocarbonyl$C_{1-6}$alkyl, $C_{1-4}$alkylaminocarbonyl$C_{1-6}$alkyl, di$C_{1-4}$alkylaminocarbonyl$C_{1-6}$alkyl, or —CR⁷R⁸ wherein R⁷ represents phenyl$C_{0-5}$alkyl and R⁸ represents di$C_{1-2}$alkylamino$C_{1-4}$alkyl, and wherein said phenyl is optionally substituted by 1, 2 or 3 substituents, which may be the same or different, selected from R⁹;
R² represents hydrogen or methyl;
R⁵ represents hydrogen or fluoro; and
R⁹ represents cyano, amino, halogen, hydroxy, $C_{1-4}$alkyl, $C_{2-4}$alkenyl, $C_{2-4}$alkynyl, halogen$C_{1-4}$alkyl, $C_{1-4}$alkoxy, $C_{1-4}$alkylamino, di$C_{1-4}$alkylamino, $C_{1-4}$alkylcarbonyl, $C_{1-4}$alkoxycarbonyl, aminocarbonyl, $C_{1-4}$alkylaminocarbonyl, di$C_{1-4}$alkylaminocarbonyl or $C_{1-4}$alkoxycarbonylamino.

Embodiment 25: a compound according to Embodiment 1 or Embodiment 2 of formula (Ia), or a pharmaceutically acceptable salt thereof,
wherein
R¹ represents $C_{1-4}$alkylamino$C_{1-6}$alkyl, di$C_{1-4}$alkylamino$C_{1-6}$alkyl, or —CR⁷R⁸ wherein R⁷ represents phenyl$C_{0-5}$alkyl and R⁸ represents di$C_{1-2}$alkylamino$C_{1-4}$alkyl, and wherein said phenyl is optionally substituted by 1, 2 or 3 substituents, which may be the same or different, selected from R⁹;
R² represents hydrogen or methyl;
R⁵ represents hydrogen or fluoro; and
R⁹ represents cyano, amino, fluoro, chloro, hydroxy, methyl or methoxy.

Embodiment 26: a compound according to Embodiment 1, which is selected from:
N,N-dimethyl-4-(5-(trifluoromethyl)-1,2,4-oxadiazol-3-yl)benzamide;
N-methyl-4-(5-(trifluoromethyl)-1,2,4-oxadiazol-3-yl)benzamide;
N-methyl-2-[4-(5-trifluoromethyl-[1,2,4]oxadiazol-3-yl)-phenyl]-acetamide;
N,N-dimethyl-2-[4-(5-trifluoromethyl-[1,2,4]oxadiazol-3-yl)-phenyl]-acetamide;
N-Isopropyl-2-[4-(5-trifluoromethyl-[1,2,4]oxadiazol-3-yl)-phenyl]-acetamide;
N-butyl-2-(4-(5-(trifluoromethyl)-1,2,4-oxadiazol-3-yl)phenyl)acetamide;
N-(2-methoxyethyl)-2-(4-(5-(trifluoromethyl)-1,2,4-oxadiazol-3-yl)phenyl)acetamide;
ethyl 2-(2-(4-(5-(trifluoromethyl)-1,2,4-oxadiazol-3-yl)phenyl)acetamido)acetate;
1-morpholino-2-(4-(5-(trifluoromethyl)-1,2,4-oxadiazol-3-yl)phenyl)ethanone;
1-(4-methylpiperazin-1-yl)-2-(4-(5-(trifluoromethyl)-1,2,4-oxadiazol-3-yl)phenyl)ethanone;
N-methoxy-N-methyl-2-(4-(5-(trifluoromethyl)-1,2,4-oxadiazol-3-yl)phenyl)acetamide;
N-ethyl-4-(5-(trifluoromethyl)-1,2,4-oxadiazol-3-yl)benzamide;
N-(2-hydroxyethyl)-4-(5-(trifluoromethyl)-1,2,4-oxadiazol-3-yl)benzamide;
N-ethyl-N-methyl-4-(5-(trifluoromethyl)-1,2,4-oxadiazol-3-yl)benzamide;
N-(2-hydroxyethyl)-N-methyl-4-(5-(trifluoromethyl)-1,2,4-oxadiazol-3-yl)benzamide;
N-(2-methoxyethyl)-4-(5-(trifluoromethyl)-1,2,4-oxadiazol-3-yl)benzamide;
N-(3-hydroxypropyl)-4-(5-(trifluoromethyl)-1,2,4-oxadiazol-3-yl)benzamide;
N-(2-methoxyethyl)-N-methyl-4-(5-(trifluoromethyl)-1,2,4-oxadiazol-3-yl)benzamide;
N-cyclopropyl-4-(5-(trifluoromethyl)-1,2,4-oxadiazol-3-yl)benzamide;
N-isopropyl-4-(5-(trifluoromethyl)-1,2,4-oxadiazol-3-yl)benzamide;
N-(3-methoxypropyl)-4-(5-(trifluoromethyl)-1,2,4-oxadiazol-3-yl)benzamide;
N-(2-fluoroethyl)-4-(5-(trifluoromethyl)-1,2,4-oxadiazol-3-yl)benzamide;
pyrrolidin-1-yl(4-(5-(trifluoromethyl)-1,2,4-oxadiazol-3-yl)phenyl)methanone;
N-isopropyl-N-methyl-4-(5-(trifluoromethyl)-1,2,4-oxadiazol-3-yl)benzamide;
N-cyclobutyl-4-(5-(trifluoromethyl)-1,2,4-oxadiazol-3-yl)benzamide;
N-(cyclopropylmethyl)-4-(5-(trifluoromethyl)-1,2,4-oxadiazol-3-yl)benzamide;
N-isobutyl-4-(5-(trifluoromethyl)-1,2,4-oxadiazol-3-yl)benzamide;
N-(1-hydroxypropan-2-yl)-4-(5-(trifluoromethyl)-1,2,4-oxadiazol-3-yl)benzamide;
N-cyclopentyl-4-(5-(trifluoromethyl)-1,2,4-oxadiazol-3-yl)benzamide;
N-(pentan-3-yl)-4-(5-(trifluoromethyl)-1,2,4-oxadiazol-3-yl)benzamide;
N-(2-(dimethylamino)ethyl)-4-(5-(trifluoromethyl)-1,2,4-oxadiazol-3-yl)benzamide;
morpholino(4-(5-(trifluoromethyl)-1,2,4-oxadiazol-3-yl)phenyl)methanone;
piperidin-1-yl(4-(5-(trifluoromethyl)-1,2,4-oxadiazol-3-yl)phenyl)methanone;
N-cyclohexyl-4-(5-(trifluoromethyl)-1,2,4-oxadiazol-3-yl)benzamide;
N-phenyl-4-(5-(trifluoromethyl)-1,2,4-oxadiazol-3-yl)benzamide;
(4-methylpiperazin-1-yl)(4-(5-(trifluoromethyl)-1,2,4-oxadiazol-3-yl)phenyl)methanone;
N-(2-(dimethylamino)ethyl)-N-methyl-4-(5-(trifluoromethyl)-1,2,4-oxadiazol-3-yl)benzamide;
N-(1-methylpiperidin-4-yl)-4-(5-(trifluoromethyl)-1,2,4-oxadiazol-3-yl)benzamide;
(4-(dimethylamino)piperidin-1-yl)(4-(5-(trifluoromethyl)-1,2,4-oxadiazol-3-yl)phenyl)methanone;
N-(3-(1H-imidazol-1-yl)propyl)-4-(5-(trifluoromethyl)-1,2,4-oxadiazol-3-yl)benzamide;
N-(4-(dimethylamino)phenyl)-4-(5-(trifluoromethyl)-1,2,4-oxadiazol-3-yl)benzamide;
(4-phenylpiperazin-1-yl)(4-(5-(trifluoromethyl)-1,2,4-oxadiazol-3-yl)phenyl)methanone;
(4-benzylpiperidin-1-yl)(4-(5-(trifluoromethyl)-1,2,4-oxadiazol-3-yl)phenyl)methanone;
N-(4-(morpholinomethyl)benzyl)-4-(5-(trifluoromethyl)-1,2,4-oxadiazol-3-yl)benzamide;

N-phenethyl-4-(5-(trifluoromethyl)-1,2,4-oxadiazol-3-yl)benzamide;
N-benzyl-4-(5-(trifluoromethyl)-1,2,4-oxadiazol-3-yl)benzamide;
N-(pyridin-4-yl)-4-(5-(trifluoromethyl)-1,2,4-oxadiazol-3-yl)benzamide;
N-(pyridin-3-yl)-4-(5-(trifluoromethyl)-1,2,4-oxadiazol-3-yl)benzamide;
N-((1-methylpiperidin-4-yl)methyl)-4-(5-(trifluoromethyl)-1,2,4-oxadiazol-3-yl)benzamide;
N-(1-hydroxypropan-2-yl)-4-(5-(trifluoromethyl)-1,2,4-oxadiazol-3-yl)benzamide;
N-(2-(dimethylamino)propyl)-4-(5-(trifluoromethyl)-1,2,4-oxadiazol-3-yl)benzamide;
N-(2-(dimethylamino)-2-oxoethyl)-4-(5-(trifluoromethyl)-1,2,4-oxadiazol-3-yl)benzamide;
N-(1-(dimethylamino)propan-2-yl)-4-(5-(trifluoromethyl)-1,2,4-oxadiazol-3-yl)benzamide;
(3-hydroxypyrrolidin-1-yl)(4-(5-(trifluoromethyl)-1,2,4-oxadiazol-3-yl)phenyl)methanone;
tert-butyl 4-(4-(5-(trifluoromethyl)-1,2,4-oxadiazol-3-yl)benzoyl)piperazine-1-carboxylate;
N-(1-hydroxybutan-2-yl)-4-(5-(trifluoromethyl)-1,2,4-oxadiazol-3-yl)benzamide;
N-(tetrahydro-2H-pyran-4-yl)-4-(5-(trifluoromethyl)-1,2,4-oxadiazol-3-yl)benzamide;
N-(1-hydroxy-4-methylpentan-2-yl)-4-(5-(trifluoromethyl)-1,2,4-oxadiazol-3-yl)benzamide;
4-[4-(5-trifluoromethyl-[1,2,4]oxadiazol-3-yl)-benzoylamino]-piperidine-1-carboxylic acid tert-butyl ester;
tert-butyl (2-(4-(5-(trifluoromethyl)-1,2,4-oxadiazol-3-yl)benzamido)cyclohexyl)carbamate;
N-(2-hydroxycyclohexyl)-4-(5-(trifluoromethyl)-1,2,4-oxadiazol-3-yl)benzamide;
tert-butyl 3-(4-(5-(trifluoromethyl)-1,2,4-oxadiazol-3-yl)benzamido)piperidine-1-carboxylate;
N-(2-(methylamino)-2-oxoethyl)-4-(5-(trifluoromethyl)-1,2,4-oxadiazol-3-yl)benzamide;
N-(1-acetylpiperidin-4-yl)-4-(5-(trifluoromethyl)-1,2,4-oxadiazol-3-yl)benzamide;
N-(1,2,2,6,6-pentamethylpiperidin-4-yl)-4-(5-(trifluoromethyl)-1,2,4-oxadiazol-3-yl)benzamide;
tert-butyl 3-(4-(5-(trifluoromethyl)-1,2,4-oxadiazol-3-yl)benzamido)pyrrolidine-1-carboxylate;
N-(2-methoxypyridin-4-yl)-4-(5-(trifluoromethyl)-1,2,4-oxadiazol-3-yl)benzamide;
N-(2,6-dimethylpyridin-4-yl)-4-(5-(trifluoromethyl)-1,2,4-oxadiazol-3-yl)benzamide;
N-(2-(tert-butyl)pyridin-4-yl)-4-(5-(trifluoromethyl)-1,2,4-oxadiazol-3-yl)benzamide;
N-(2-methylpyridin-4-yl)-4-(5-(trifluoromethyl)-1,2,4-oxadiazol-3-yl)benzamide;
N-(2-fluoropyridin-4-yl)-4-(5-(trifluoromethyl)-1,2,4-oxadiazol-3-yl)benzamide;
N-(2-hydroxypyridin-4-yl)-4-(5-(trifluoromethyl)-1,2,4-oxadiazol-3-yl)benzamide;
N-(2-cyanopyridin-4-yl)-4-(5-(trifluoromethyl)-1,2,4-oxadiazol-3-yl)benzamide;
4-(5-(trifluoromethyl)-1,2,4-oxadiazol-3-yl)-N-(2-(trifluoromethyl)pyridin-4-yl)benzamide;
N-(2-chloropyridin-4-yl)-4-(5-(trifluoromethyl)-1,2,4-oxadiazol-3-yl)benzamide;
N-(piperidin-4-yl)-4-(5-(trifluoromethyl)-1,2,4-oxadiazol-3-yl)benzamide;
N-(2-aminocyclohexyl)-4-(5-(trifluoromethyl)-1,2,4-oxadiazol-3-yl)benzamide;
N-(piperidin-2-ylmethyl)-4-(5-(trifluoromethyl)-1,2,4-oxadiazol-3-yl)benzamide;
N-(piperidin-3-yl)-4-(5-(trifluoromethyl)-1,2,4-oxadiazol-3-yl)benzamide;
N-(pyrrolidin-3-yl)-4-(5-(trifluoromethyl)-1,2,4-oxadiazol-3-yl)benzamide;
N-(1-(dimethylamino)-3-methylbutan-2-yl)-4-(5-(trifluoromethyl)-1,2,4-oxadiazol-3-yl)benzamide;
N-(1-(dimethylamino)-4-methylpentan-2-yl)-4-(5-(trifluoromethyl)-1,2,4-oxadiazol-3-yl)benzamide;
N-(pyrrolidin-3-yl)-4-(5-(trifluoromethyl)-1,2,4-oxadiazol-3-yl)benzamide;
N-(1-(dimethylamino)propan-2-yl)-2-fluoro-4-(5-(trifluoromethyl)-1,2,4-oxadiazol-3-yl)benzamide;
N-(1-(dimethylamino)-3-methylbutan-2-yl)-2-fluoro-4-(5-(trifluoromethyl)-1,2,4-oxadiazol-3-yl)benzamide;
N-(2,6-dimethylpyridin-4-yl)-2-fluoro-4-(5-(trifluoromethyl)-1,2,4-oxadiazol-3-yl)benzamide;
2-fluoro-N-(1-hydroxypropan-2-yl)-4-(5-(trifluoromethyl)-1,2,4-oxadiazol-3-yl)benzamide;
N-(1-(dimethylamino)-3-phenylpropan-2-yl)-4-(5-(trifluoromethyl)-1,2,4-oxadiazol-3-yl)benzamide;
N-(1-(dimethylamino)propan-2-yl)-N-methyl-4-(5-(trifluoromethyl)-1,2,4-oxadiazol-3-yl)benzamide;
2-fluoro-N-(pyrrolidin-3-yl)-4-(5-(trifluoromethyl)-1,2,4-oxadiazol-3-yl)benzamide;
N-benzyl-4-(5-(trifluoromethyl)-1,2,4-oxadiazol-3-yl)benzenesulfonamide;
N-(2-(dimethylamino)ethyl)-4-(5-(trifluoromethyl)-1,2,4-oxadiazol-3-yl)benzenesulfonamide;
N-(2-(dimethylamino)ethyl)-N-methyl-4-(5-(trifluoromethyl)-1,2,4-oxadiazol-3-yl)benzenesulfonamide;
N-(pyridin-3-yl)-4-(5-(trifluoromethyl)-1,2,4-oxadiazol-3-yl)benzenesulfonamide;
N-(cyclohexyl methyl)-4-(5-(trifluoromethyl)-1,2,4-oxadiazol-3-yl)benzenesulfonamide;
N-(pyrrolidin-3-yl)-4-(5-(trifluoromethyl)-1,2,4-oxadiazol-3-yl)benzenesulfonamide;
N-o-tolyl-4-(5-trifluoromethyl-[1,2,4]oxadiazol-3-yl)-benzenesulfonamide;
N-(2-chlorophenyl)-4-(5-(trifluoromethyl)-1,2,4-oxadiazol-3-yl)benzenesulfonamide;
N-m-tolyl-4-(5-(trifluoromethyl)-1,2,4-oxadiazol-3-yl)benzenesulfonamide;
N-(3-fluorophenyl)-4-(5-(trifluoromethyl)-1,2,4-oxadiazol-3-yl)benzenesulfonamide;
N-(3-chlorophenyl)-4-(5-(trifluoromethyl)-1,2,4-oxadiazol-3-yl)benzenesulfonamide;
N-p-tolyl-4-(5-(trifluoromethyl)-1,2,4-oxadiazol-3-yl)benzenesulfonamide;
N-(4-fluorophenyl)-4-(5-(trifluoromethyl)-1,2,4-oxadiazol-3-yl)benzenesulfonamide;
N-(4-chlorophenyl)-4-(5-(trifluoromethyl)-1,2,4-oxadiazol-3-yl)benzenesulfonamide;
N-(2-fluorophenyl)-4-(5-(trifluoromethyl)-1,2,4-oxadiazol-3-yl)benzenesulfonamide;
N-(3-(dimethylamino)propyl)-N-methyl-4-(5-(trifluoromethyl)-1,2,4-oxadiazol-3-yl)benzenesulfonamide;
N-(3-(dimethylamino)propyl)-4-(5-(trifluoromethyl)-1,2,4-oxadiazol-3-yl)benzenesulfonamide;
N,N-dimethyl-4-(5-(trifluoromethyl)-1,2,4-oxadiazol-3-yl)benzenesulfonamide;
N-((1-methylpyrrolidin-3-yl)methyl)-4-(5-(trifluoromethyl)-1,2,4-oxadiazol-3-yl)benzenesulfonamide;
N-(3-hydroxypropyl)-4-(5-(trifluoromethyl)-1,2,4-oxadiazol-3-yl)benzenesulfonamide;

N-(1-(dimethylamino)-3-phenylpropan-2-yl)-2-fluoro-4-(5-(trifluoromethyl)-1,2,4-oxadiazol-3-yl)benzamide;
N-(1-(dimethylamino)-2-methylpropan-2-yl)-4-(5-(trifluoromethyl)-1,2,4-oxadiazol-3-yl)benzamide;
N-(1-(dimethylamino)-2-methylpropan-2-yl)-2-fluoro-4-(5-(trifluoromethyl)-1,2,4-oxadiazol-3-yl)benzamide;
N-(1-(diethylamino)propan-2-yl)-2-fluoro-4-(5-(trifluoromethyl)-1,2,4-oxadiazol-3-yl)benzamide;
N-(2-(dimethylamino)propyl)-2-fluoro-4-(5-(trifluoromethyl)-1,2,4-oxadiazol-3-yl)benzamide;
N-(1-(diethylamino)propan-2-yl)-4-(5-(trifluoromethyl)-1,2,4-oxadiazol-3-yl)benzamide;
N-(1-(dimethylamino)propan-2-yl)-2,6-difluoro-4-(5-(trifluoromethyl)-1,2,4-oxadiazol-3-yl)benzamide;
2-chloro-N-(1-(dimethylamino)propan-2-yl)-4-(5-(trifluoromethyl)-1,2,4-oxadiazol-3-yl)benzamide;
2-fluoro-N-(1-(pyrrolidin-1-yl)propan-2-yl)-4-(5-(trifluoromethyl)-1,2,4-oxadiazol-3-yl)benzamide;
2-fluoro-N-(1-(piperidin-1-yl)propan-2-yl)-4-(5-(trifluoromethyl)-1,2,4-oxadiazol-3-yl)benzamide;
N-(1-(pyrrolidin-1-yl)propan-2-yl)-4-(5-(trifluoromethyl)-1,2,4-oxadiazol-3-yl)benzamide;
N-(1-(piperidin-1-yl)propan-2-yl)-4-(5-(trifluoromethyl)-1,2,4-oxadiazol-3-yl)benzamide;
N-(1-(diethylamino)-3-methylbutan-2-yl)-4-(5-(trifluoromethyl)-1,2,4-oxadiazol-3-yl)benzamide;
N-(1-(diethylamino)-3-methylbutan-2-yl)-2-fluoro-4-(5-(trifluoromethyl)-1,2,4-oxadiazol-3-yl)benzamide;
N-(1-(ethyl(methyl)amino)propan-2-yl)-4-(5-(trifluoromethyl)-1,2,4-oxadiazol-3-yl)benzamide;
N-(1-(dipropylamino)propan-2-yl)-4-(5-(trifluoromethyl)-1,2,4-oxadiazol-3-yl)benzamide;
N-(1-(isopropyl(methyl)amino)propan-2-yl)-4-(5-(trifluoromethyl)-1,2,4-oxadiazol-3-yl)benzamide;
N-(1-(methyl(propyl)amino)propan-2-yl)-4-(5-(trifluoromethyl)-1,2,4-oxadiazol-3-yl)benzamide;
N-(1-(ethyl(methyl)amino)propan-2-yl)-2-fluoro-4-(5-(trifluoromethyl)-1,2,4-oxadiazol-3-yl)benzamide;
N-(1-(dipropylamino)propan-2-yl)-2-fluoro-4-(5-(trifluoromethyl)-1,2,4-oxadiazol-3-yl)benzamide;
2-fluoro-N-(1-(isopropyl(methyl)amino)propan-2-yl)-4-(5-(trifluoromethyl)-1,2,4-oxadiazol-3-yl)benzamide;
2-fluoro-N-(1-(methyl(propyl)amino)propan-2-yl)-4-(5-(trifluoromethyl)-1,2,4-oxadiazol-3-yl)benzamide;
N-(1-(dimethylamino)propan-2-yl)-2-fluoro-N-methyl-4-(5-(trifluoromethyl)-1,2,4-oxadiazol-3-yl)benzamide;
N-(1-(ethyl(propyl)amino)propan-2-yl)-4-(5-(trifluoromethyl)-1,2,4-oxadiazol-3-yl)benzamide;
N-(1-(ethyl(propyl)amino)propan-2-yl)-2-fluoro-4-(5-(trifluoromethyl)-1,2,4-oxadiazol-3-yl)benzamide;
N-(1-morpholinopropan-2-yl)-4-(5-(trifluoromethyl)-1,2,4-oxadiazol-3-yl)benzamide;
2-fluoro-N-(1-morpholinopropan-2-yl)-4-(5-(trifluoromethyl)-1,2,4-oxadiazol-3-yl)benzamide;
N-(1-methylpiperidin-3-yl)-4-(5-(trifluoromethyl)-1,2,4-oxadiazol-3-yl)benzamide;
N-(1-(butyl(methyl)amino)propan-2-yl)-4-(5-(trifluoromethyl)-1,2,4-oxadiazol-3-yl)benzamide;
N-(1-(butyl(methyl)amino)propan-2-yl)-2-fluoro-4-(5-(trifluoromethyl)-1,2,4-oxadiazol-3-yl)benzamide;
N-(1-(ethyl(isopropyl)amino)propan-2-yl)-2-fluoro-4-(5-(trifluoromethyl)-1,2,4-oxadiazol-3-yl)benzamide;
N-(1-methylpyrrolidin-3-yl)-4-(5-(trifluoromethyl)-1,2,4-oxadiazol-3-yl)benzamide;
N-(2-(diethylamino)ethyl)-4-(5-(trifluoromethyl)-1,2,4-oxadiazol-3-yl)benzamide;
N-(1-(benzyl(methyl)amino)propan-2-yl)-4-(5-(trifluoromethyl)-1,2,4-oxadiazol-3-yl)benzamide;
N-(2-(methylamino)ethyl)-4-(5-(trifluoromethyl)-1,2,4-oxadiazol-3-yl)benzamide;
N-(2-(phenylamino)ethyl)-4-(5-(trifluoromethyl)-1,2,4-oxadiazol-3-yl)benzamide;
and pharmaceutically acceptable salts thereof.

Embodiment 27: a compound according to Embodiment 1, which is selected from:
N,N-dimethyl-4-(5-(trifluoromethyl)-1,2,4-oxadiazol-3-yl)benzamide;
N-methyl-4-(5-(trifluoromethyl)-1,2,4-oxadiazol-3-yl)benzamide;
N-methyl-2-[4-(5-trifluoromethyl-[1,2,4]oxadiazol-3-yl)-phenyl]-acetamide;
N,N-dimethyl-2-[4-(5-trifluoromethyl-[1,2,4]oxadiazol-3-yl)-phenyl]-acetamide;
N-Isopropyl-2-[4-(5-trifluoromethyl-[1,2,4]oxadiazol-3-yl)-phenyl]-acetamide;
N-butyl-2-(4-(5-(trifluoromethyl)-1,2,4-oxadiazol-3-yl)phenyl)acetamide;
N-(2-methoxyethyl)-2-(4-(5-(trifluoromethyl)-1,2,4-oxadiazol-3-yl)phenyl)acetamide;
ethyl 2-(2-(4-(5-(trifluoromethyl)-1,2,4-oxadiazol-3-yl)phenyl)acetamido)acetate;
1-morpholino-2-(4-(5-(trifluoromethyl)-1,2,4-oxadiazol-3-yl)phenyl)ethanone;
1-(4-methylpiperazin-1-yl)-2-(4-(5-(trifluoromethyl)-1,2,4-oxadiazol-3-yl)phenyl)ethanone;
N-methoxy-N-methyl-2-(4-(5-(trifluoromethyl)-1,2,4-oxadiazol-3-yl)phenyl)acetamide;
N-ethyl-4-(5-(trifluoromethyl)-1,2,4-oxadiazol-3-yl)benzamide;
N-(2-hydroxyethyl)-4-(5-(trifluoromethyl)-1,2,4-oxadiazol-3-yl)benzamide;
N-ethyl-N-methyl-4-(5-(trifluoromethyl)-1,2,4-oxadiazol-3-yl)benzamide;
N-(2-hydroxyethyl)-N-methyl-4-(5-(trifluoromethyl)-1,2,4-oxadiazol-3-yl)benzamide;
N-(2-methoxyethyl)-4-(5-(trifluoromethyl)-1,2,4-oxadiazol-3-yl)benzamide;
N-(3-hydroxypropyl)-4-(5-(trifluoromethyl)-1,2,4-oxadiazol-3-yl)benzamide;
N-(2-methoxyethyl)-N-methyl-4-(5-(trifluoromethyl)-1,2,4-oxadiazol-3-yl)benzamide;
N-cyclopropyl-4-(5-(trifluoromethyl)-1,2,4-oxadiazol-3-yl)benzamide;
N-isopropyl-4-(5-(trifluoromethyl)-1,2,4-oxadiazol-3-yl)benzamide;
N-(3-methoxypropyl)-4-(5-(trifluoromethyl)-1,2,4-oxadiazol-3-yl)benzamide;
N-(2-fluoroethyl)-4-(5-(trifluoromethyl)-1,2,4-oxadiazol-3-yl)benzamide;
pyrrolidin-1-yl(4-(5-(trifluoromethyl)-1,2,4-oxadiazol-3-yl)phenyl)methanone;
N-isopropyl-N-methyl-4-(5-(trifluoromethyl)-1,2,4-oxadiazol-3-yl)benzamide;
N-cyclobutyl-4-(5-(trifluoromethyl)-1,2,4-oxadiazol-3-yl)benzamide;
N-(cyclopropylmethyl)-4-(5-(trifluoromethyl)-1,2,4-oxadiazol-3-yl)benzamide;
N-isobutyl-4-(5-(trifluoromethyl)-1,2,4-oxadiazol-3-yl)benzamide;
(R)—N-(1-hydroxypropan-2-yl)-4-(5-(trifluoromethyl)-1,2,4-oxadiazol-3-yl)benzamide;
N-cyclopentyl-4-(5-(trifluoromethyl)-1,2,4-oxadiazol-3-yl)benzamide;

N-(pentan-3-yl)-4-(5-(trifluoromethyl)-1,2,4-oxadiazol-3-yl)benzamide;
N-(2-(dimethylamino)ethyl)-4-(5-(trifluoromethyl)-1,2,4-oxadiazol-3-yl)benzamide;
morpholino(4-(5-(trifluoromethyl)-1,2,4-oxadiazol-3-yl)phenyl)methanone;
piperidin-1-yl(4-(5-(trifluoromethyl)-1,2,4-oxadiazol-3-yl)phenyl)methanone;
N-cyclohexyl-4-(5-(trifluoromethyl)-1,2,4-oxadiazol-3-yl)benzamide;
N-phenyl-4-(5-(trifluoromethyl)-1,2,4-oxadiazol-3-yl)benzamide;
(4-methylpiperazin-1-yl)(4-(5-(trifluoromethyl)-1,2,4-oxadiazol-3-yl)phenyl)methanone;
N-(2-(dimethylamino)ethyl)-N-methyl-4-(5-(trifluoromethyl)-1,2,4-oxadiazol-3-yl)benzamide;
N-(1-methylpiperidin-4-yl)-4-(5-(trifluoromethyl)-1,2,4-oxadiazol-3-yl)benzamide;
(4-(dimethylamino)piperidin-1-yl)(4-(5-(trifluoromethyl)-1,2,4-oxadiazol-3-yl)phenyl)methanone;
N-(3-(1 H-imidazol-1-yl)propyl)-4-(5-(trifluoromethyl)-1,2,4-oxadiazol-3-yl)benzamide;
N-(4-(dimethylamino)phenyl)-4-(5-(trifluoromethyl)-1,2,4-oxadiazol-3-yl)benzamide;
(4-phenylpiperazin-1-yl)(4-(5-(trifluoromethyl)-1,2,4-oxadiazol-3-yl)phenyl)methanone;
(4-benzylpiperidin-1-yl)(4-(5-(trifluoromethyl)-1,2,4-oxadiazol-3-yl)phenyl)methanone;
N-(4-(morpholinomethyl)benzyl)-4-(5-(trifluoromethyl)-1,2,4-oxadiazol-3-yl)benzamide;
N-phenethyl-4-(5-(trifluoromethyl)-1,2,4-oxadiazol-3-yl)benzamide;
N-benzyl-4-(5-(trifluoromethyl)-1,2,4-oxadiazol-3-yl)benzamide;
N-(pyridin-4-yl)-4-(5-(trifluoromethyl)-1,2,4-oxadiazol-3-yl)benzamide;
N-(pyridin-3-yl)-4-(5-(trifluoromethyl)-1,2,4-oxadiazol-3-yl)benzamide;
N-((1-methylpiperidin-4-yl)methyl)-4-(5-(trifluoromethyl)-1,2,4-oxadiazol-3-yl)benzamide;
(S)—N-(1-hydroxypropan-2-yl)-4-(5-(trifluoromethyl)-1,2,4-oxadiazol-3-yl)benzamide;
N-(2-(dimethylamino)propyl)-4-(5-(trifluoromethyl)-1,2,4-oxadiazol-3-yl)benzamide;
N-(2-(dimethylamino)-2-oxoethyl)-4-(5-(trifluoromethyl)-1,2,4-oxadiazol-3-yl)benzamide;
N-(1-(dimethylamino)propan-2-yl)-4-(5-(trifluoromethyl)-1,2,4-oxadiazol-3-yl)benzamide;
(3-hydroxypyrrolidin-1-yl)(4-(5-(trifluoromethyl)-1,2,4-oxadiazol-3-yl)phenyl)methanone;
tert-butyl 4-(4-(5-(trifluoromethyl)-1,2,4-oxadiazol-3-yl)benzoyl)piperazine-1-carboxylate;
N-(1-hydroxybutan-2-yl)-4-(5-(trifluoromethyl)-1,2,4-oxadiazol-3-yl)benzamide;
N-(tetrahydro-2 H-pyran-4-yl)-4-(5-(trifluoromethyl)-1,2,4-oxadiazol-3-yl)benzamide;
N-(1-hydroxy-4-methylpentan-2-yl)-4-(5-(trifluoromethyl)-1,2,4-oxadiazol-3-yl)benzamide;
4-[4-(5-trifluoromethyl-[1,2,4]oxadiazol-3-yl)-benzoylamino]-piperidine-1-carboxylic acid tert-butyl ester;
tert-butyl (2-(4-(5-(trifluoromethyl)-1,2,4-oxadiazol-3-yl)benzamido)cyclohexyl)carbamate;
N-(2-hydroxycyclohexyl)-4-(5-(trifluoromethyl)-1,2,4-oxadiazol-3-yl)benzamide;
tert-butyl 3-(4-(5-(trifluoromethyl)-1,2,4-oxadiazol-3-yl)benzamido)piperidine-1-carboxylate;
N-(2-(methylamino)-2-oxoethyl)-4-(5-(trifluoromethyl)-1,2,4-oxadiazol-3-yl)benzamide;
N-(1-acetylpiperidin-4-yl)-4-(5-(trifluoromethyl)-1,2,4-oxadiazol-3-yl)benzamide;
N-(1,2,2,6,6-pentamethylpiperidin-4-yl)-4-(5-(trifluoromethyl)-1,2,4-oxadiazol-3-yl)benzamide;
tert-butyl 3-(4-(5-(trifluoromethyl)-1,2,4-oxadiazol-3-yl)benzamido)pyrrolidine-1-carboxylate;
N-(2-methoxypyridin-4-yl)-4-(5-(trifluoromethyl)-1,2,4-oxadiazol-3-yl)benzamide;
N-(2,6-dimethylpyridin-4-yl)-4-(5-(trifluoromethyl)-1,2,4-oxadiazol-3-yl)benzamide;
N-(2-(tert-butyl)pyridin-4-yl)-4-(5-(trifluoromethyl)-1,2,4-oxadiazol-3-yl)benzamide;
N-(2-methylpyridin-4-yl)-4-(5-(trifluoromethyl)-1,2,4-oxadiazol-3-yl)benzamide;
N-(2-fluoropyridin-4-yl)-4-(5-(trifluoromethyl)-1,2,4-oxadiazol-3-yl)benzamide;
N-(2-hydroxypyridin-4-yl)-4-(5-(trifluoromethyl)-1,2,4-oxadiazol-3-yl)benzamide;
N-(2-cyanopyridin-4-yl)-4-(5-(trifluoromethyl)-1,2,4-oxadiazol-3-yl)benzamide;
4-(5-(trifluoromethyl)-1,2,4-oxadiazol-3-yl)-N-(2-(trifluoromethyl)pyridin-4-yl)benzamide;
N-(2-chloropyridin-4-yl)-4-(5-(trifluoromethyl)-1,2,4-oxadiazol-3-yl)benzamide;
N-(piperidin-4-yl)-4-(5-(trifluoromethyl)-1,2,4-oxadiazol-3-yl)benzamide;
N-(2-aminocyclohexyl)-4-(5-(trifluoromethyl)-1,2,4-oxadiazol-3-yl)benzamide;
N-(piperidin-2-ylmethyl)-4-(5-(trifluoromethyl)-1,2,4-oxadiazol-3-yl)benzamide;
N-(piperidin-3-yl)-4-(5-(trifluoromethyl)-1,2,4-oxadiazol-3-yl)benzamide;
N-(pyrrolidin-3-yl)-4-(5-(trifluoromethyl)-1,2,4-oxadiazol-3-yl)benzamide;
(R)—N-(1-(dimethylamino)propan-2-yl)-4-(5-(trifluoromethyl)-1,2,4-oxadiazol-3-yl)benzamide;
(S)—N-(1-(dimethylamino)propan-2-yl)-4-(5-(trifluoromethyl)-1,2,4-oxadiazol-3-yl)benzamide;
(S)—N-(1-(dimethylamino)-3-methylbutan-2-yl)-4-(5-(trifluoromethyl)-1,2,4-oxadiazol-3-yl)benzamide;
(R)—N-(1-(dimethylamino)-3-methylbutan-2-yl)-4-(5-(trifluoromethyl)-1,2,4-oxadiazol-3-yl)benzamide;
(R)—N-(1-(dimethylamino)-4-methylpentan-2-yl)-4-(5-(trifluoromethyl)-1,2,4-oxadiazol-3-yl)benzamide;
(R)—N-(pyrrolidin-3-yl)-4-(5-(trifluoromethyl)-1,2,4-oxadiazol-3-yl)benzamide;
(S)—N-(pyrrolidin-3-yl)-4-(5-(trifluoromethyl)-1,2,4-oxadiazol-3-yl)benzamide;
(R)—N-(1-(dimethylamino)propan-2-yl)-2-fluoro-4-(5-(trifluoromethyl)-1,2,4-oxadiazol-3-yl)benzamide;
(R)—N-(1-(dimethylamino)-3-methylbutan-2-yl)-2-fluoro-4-(5-(trifluoromethyl)-1,2,4-oxadiazol-3-yl)benzamide;
N-(2,6-dimethylpyridin-4-yl)-2-fluoro-4-(5-(trifluoromethyl)-1,2,4-oxadiazol-3-yl)benzamide;
2-fluoro-N-(1-hydroxypropan-2-yl)-4-(5-(trifluoromethyl)-1,2,4-oxadiazol-3-yl)benzamide;
(R)—N-(1-(dimethylamino)-3-phenylpropan-2-yl)-4-(5-(trifluoromethyl)-1,2,4-oxadiazol-3-yl)benzamide;
(S)—N-(1-(dimethylamino)-3-phenylpropan-2-yl)-4-(5-(trifluoromethyl)-1,2,4-oxadiazol-3-yl)benzamide;
N-(1-(dimethylamino)propan-2-yl)-N-methyl-4-(5-(trifluoromethyl)-1,2,4-oxadiazol-3-yl)benzamide;
(R)-2-fluoro-N-(pyrrolidin-3-yl)-4-(5-(trifluoromethyl)-1,2,4-oxadiazol-3-yl)benzamide;

N-phenyl-4-(5-(trifluoromethyl)-1,2,4-oxadiazol-3-yl)benzenesulfonamide;
N-benzyl-4-(5-(trifluoromethyl)-1,2,4-oxadiazol-3-yl)benzenesulfonamide;
N-(2-(dimethylamino)ethyl)-4-(5-(trifluoromethyl)-1,2,4-oxadiazol-3-yl)benzenesulfonamide;
N-(2-(dimethylamino)ethyl)-N-methyl-4-(5-(trifluoromethyl)-1,2,4-oxadiazol-3-yl)benzenesulfonamide;
N-(pyridin-3-yl)-4-(5-(trifluoromethyl)-1,2,4-oxadiazol-3-yl)benzenesulfonamide;
N-(cyclohexyl methyl)-4-(5-(trifluoromethyl)-1,2,4-oxadiazol-3-yl)benzenesulfonamide;
(R)—N-(pyrrolidin-3-yl)-4-(5-(trifluoromethyl)-1,2,4-oxadiazol-3-yl)benzenesulfonamide;
N-o-tolyl-4-(5-trifluoromethyl-[1,2,4]oxadiazol-3-yl)-benzenesulfonamide;
N-(2-chlorophenyl)-4-(5-(trifluoromethyl)-1,2,4-oxadiazol-3-yl)benzenesulfonamide;
N-m-tolyl-4-(5-(trifluoromethyl)-1,2,4-oxadiazol-3-yl)benzenesulfonamide;
N-(3-fluorophenyl)-4-(5-(trifluoromethyl)-1,2,4-oxadiazol-3-yl)benzenesulfonamide;
N-(3-chlorophenyl)-4-(5-(trifluoromethyl)-1,2,4-oxadiazol-3-yl)benzenesulfonamide;
N-p-tolyl-4-(5-(trifluoromethyl)-1,2,4-oxadiazol-3-yl)benzenesulfonamide;
N-(4-fluorophenyl)-4-(5-(trifluoromethyl)-1,2,4-oxadiazol-3-yl)benzenesulfonamide;
N-(4-chlorophenyl)-4-(5-(trifluoromethyl)-1,2,4-oxadiazol-3-yl)benzenesulfonamide;
N-(2-fluorophenyl)-4-(5-(trifluoromethyl)-1,2,4-oxadiazol-3-yl)benzenesulfonamide;
N-(3-(dimethylamino)propyl)-N-methyl-4-(5-(trifluoromethyl)-1,2,4-oxadiazol-3-yl)benzenesulfonamide;
N-(3-(dimethylamino)propyl)-4-(5-(trifluoromethyl)-1,2,4-oxadiazol-3-yl)benzenesulfonamide;
N,N-dimethyl-4-(5-(trifluoromethyl)-1,2,4-oxadiazol-3-yl)benzenesulfonamide;
N-((1-methylpyrrolidin-3-yl)methyl)-4-(5-(trifluoromethyl)-1,2,4-oxadiazol-3-yl)benzenesulfonamide;
N-(3-hydroxypropyl)-4-(5-(trifluoromethyl)-1,2,4-oxadiazol-3-yl)benzenesulfonamide;
(S)—N-(1-(dimethylamino)-3-phenylpropan-2-yl)-2-fluoro-4-(5-(trifluoromethyl)-1,2,4-oxadiazol-3-yl)benzamide;
(R)—N-(1-(dimethylamino)-3-phenylpropan-2-yl)-2-fluoro-4-(5-(trifluoromethyl)-1,2,4-oxadiazol-3-yl)benzamide;
N-(1-(dimethylamino)-2-methylpropan-2-yl)-4-(5-(trifluoromethyl)-1,2,4-oxadiazol-3-yl)benzamide;
N-(1-(dimethylamino)-2-methylpropan-2-yl)-2-fluoro-4-(5-(trifluoromethyl)-1,2,4-oxadiazol-3-yl)benzamide;
N-(1-(diethylamino)propan-2-yl)-2-fluoro-4-(5-(trifluoromethyl)-1,2,4-oxadiazol-3-yl)benzamide;
N-(2-(dimethylamino)propyl)-2-fluoro-4-(5-(trifluoromethyl)-1,2,4-oxadiazol-3-yl)benzamide;
N-(1-(diethylamino)propan-2-yl)-4-(5-(trifluoromethyl)-1,2,4-oxadiazol-3-yl)benzamide;
(R)—N-(1-(dimethylamino)propan-2-yl)-2,6-difluoro-4-(5-(trifluoromethyl)-1,2,4-oxadiazol-3-yl)benzamide;
(R)-2-chloro-N-(1-(dimethylamino)propan-2-yl)-4-(5-(trifluoromethyl)-1,2,4-oxadiazol-3-yl)benzamide;
(R)—N-(1-(diethylamino)propan-2-yl)-2-fluoro-4-(5-(trifluoromethyl)-1,2,4-oxadiazol-3-yl)benzamide;
(S)—N-(1-(diethylamino)propan-2-yl)-2-fluoro-4-(5-(trifluoromethyl)-1,2,4-oxadiazol-3-yl)benzamide;
(R)-2-fluoro-N-(1-(pyrrolidin-1-yl)propan-2-yl)-4-(5-(trifluoromethyl)-1,2,4-oxadiazol-3-yl)benzamide;
(R)-2-fluoro-N-(1-(piperidin-1-yl)propan-2-yl)-4-(5-(trifluoromethyl)-1,2,4-oxadiazol-3-yl)benzamide;
(R)—N-(1-(pyrrolidin-1-yl)propan-2-yl)-4-(5-(trifluoromethyl)-1,2,4-oxadiazol-3-yl)benzamide;
(R)—N-(1-(piperidin-1-yl)propan-2-yl)-4-(5-(trifluoromethyl)-1,2,4-oxadiazol-3-yl)benzamide;
(R)—N-(1-(diethylamino)propan-2-yl)-4-(5-(trifluoromethyl)-1,2,4-oxadiazol-3-yl)benzamide;
(S)—N-(1-(diethylamino)propan-2-yl)-4-(5-(trifluoromethyl)-1,2,4-oxadiazol-3-yl)benzamide;
(R)—N-(1-(diethylamino)-3-methylbutan-2-yl)-4-(5-(trifluoromethyl)-1,2,4-oxadiazol-3-yl)benzamide;
(R)—N-(1-(diethylamino)-3-methylbutan-2-yl)-2-fluoro-4-(5-(trifluoromethyl)-1,2,4-oxadiazol-3-yl)benzamide;
(R)—N-(1-(ethyl(methyl)amino)propan-2-yl)-4-(5-(trifluoromethyl)-1,2,4-oxadiazol-3-yl)benzamide;
(R)—N-(1-(dipropylamino)propan-2-yl)-4-(5-(trifluoromethyl)-1,2,4-oxadiazol-3-yl)benzamide;
(R)—N-(1-(isopropyl(methyl)amino)propan-2-yl)-4-(5-(trifluoromethyl)-1,2,4-oxadiazol-3-yl)benzamide;
(R)—N-(1-(methyl(propyl)amino)propan-2-yl)-4-(5-(trifluoromethyl)-1,2,4-oxadiazol-3-yl)benzamide;
(R)—N-(1-(ethyl(methyl)amino)propan-2-yl)-2-fluoro-4-(5-(trifluoromethyl)-1,2,4-oxadiazol-3-yl)benzamide;
(R)—N-(1-(dipropylamino)propan-2-yl)-2-fluoro-4-(5-(trifluoromethyl)-1,2,4-oxadiazol-3-yl)benzamide;
(R)-2-fluoro-N-(1-(isopropyl(methyl)amino)propan-2-yl)-4-(5-(trifluoromethyl)-1,2,4-oxadiazol-3-yl)benzamide;
(R)-2-fluoro-N-(1-(methyl(propyl)amino)propan-2-yl)-4-(5-(trifluoromethyl)-1,2,4-oxadiazol-3-yl)benzamide;
N-(1-(dimethylamino)propan-2-yl)-2-fluoro-N-methyl-4-(5-(trifluoromethyl)-1,2,4-oxadiazol-3-yl)benzamide;
(R)—N-(1-(ethyl(propyl)amino)propan-2-yl)-4-(5-(trifluoromethyl)-1,2,4-oxadiazol-3-yl)benzamide;
(R)—N-(1-(ethyl(propyl)amino)propan-2-yl)-2-fluoro-4-(5-(trifluoromethyl)-1,2,4-oxadiazol-3-yl)benzamide;
(R)—N-(1-morpholinopropan-2-yl)-4-(5-(trifluoromethyl)-1,2,4-oxadiazol-3-yl)benzamide;
(R)-2-fluoro-N-(1-morpholinopropan-2-yl)-4-(5-(trifluoromethyl)-1,2,4-oxadiazol-3-yl)benzamide;
N-(1-methylpiperidin-3-yl)-4-(5-(trifluoromethyl)-1,2,4-oxadiazol-3-yl)benzamide;
(R)—N-(1-(butyl(methyl)amino)propan-2-yl)-4-(5-(trifluoromethyl)-1,2,4-oxadiazol-3-yl)benzamide;
(R)—N-(1-(butyl(methyl)amino)propan-2-yl)-2-fluoro-4-(5-(trifluoromethyl)-1,2,4-oxadiazol-3-yl)benzamide;
(R)—N-(1-(ethyl(isopropyl)amino)propan-2-yl)-2-fluoro-4-(5-(trifluoromethyl)-1,2,4-oxadiazol-3-yl)benzamide;
(R)—N-(1-methylpyrrolidin-3-yl)-4-(5-(trifluoromethyl)-1,2,4-oxadiazol-3-yl)benzamide;
(R)—N-(1-methylpiperidin-3-yl)-4-(5-(trifluoromethyl)-1,2,4-oxadiazol-3-yl)benzamide;
N-(2-(diethylamino)ethyl)-4-(5-(trifluoromethyl)-1,2,4-oxadiazol-3-yl)benzamide;
(R)—N-(1-(benzyl(methyl)amino)propan-2-yl)-4-(5-(trifluoromethyl)-1,2,4-oxadiazol-3-yl)benzamide;
N-(2-(methylamino)ethyl)-4-(5-(trifluoromethyl)-1,2,4-oxadiazol-3-yl)benzamide;
N-(2-(phenylamino)ethyl)-4-(5-(trifluoromethyl)-1,2,4-oxadiazol-3-yl)benzamide;
and pharmaceutically acceptable salts thereof.

On account of one or more than one asymmetrical carbon atom, which may be present in a compound of the formula (I), a corresponding compound of the formula (I) may exist in pure optically active form or in the form of a mixture of optical isomers, e.g. in the form of a racemic mixture. All of such pure optical isomers and all of their mixtures, including the racemic mixtures, are part of the present invention.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration.

Where a compound of the Examples comprising one or more chiral centers is drawn herein with the stereochemistry indicated in the drawn structure, then the individual optical isomer is intended. Where a compound of the Examples comprising one or more chiral centers is drawn herein without the stereochemistry indicated in the drawn structure, then a mixture of optical isomers is intended.

In one embodiment of the invention, there is provided a compound of the Examples having one chiral center as an isolated stereoisomer in the R configuration.

In one embodiment of the invention, there is provided a compound of the Examples having one chiral center as an isolated stereoisomer in the S configuration.

In one embodiment of the invention, there is provided a compound of the Examples having one chiral center as a racemic mixture.

It is also possible that the intermediates and compounds of the present invention may exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. A specific example of a proton tautomer is the imidazole moiety where the proton may migrate between the two ring nitrogens. Valence tautomers include interconversions by reorganization of some of the bonding electrons.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

As used herein, the terms "salt" or "salts" refers to an acid addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. The compounds of the present invention may be capable of forming acid salts by virtue of the presence of amino groups or groups similar thereto.

In one embodiment, the invention relates to a compound of the formula (I) or (Ia) as defined herein, in free form. In another embodiment, the invention relates to a compound of the formula (I) or (Ia) as defined herein, in salt form. In another embodiment, the invention relates to a compound of the formula (I) or (Ia) as defined herein, in acid addition salt form. In a further embodiment, the invention relates to a compound of the formula (I) or (Ia) as defined herein, in pharmaceutically acceptable salt form. In yet a further embodiment, the invention relates to a compound of the formula (I) or (Ia) as defined herein, in pharmaceutically acceptable acid addition salt form. In yet a further embodiment, the invention relates to any one of the compounds of the Examples in free form. In yet a further embodiment, the invention relates to any one of the compounds of the Examples in salt form. In yet a further embodiment, the invention relates to any one of the compounds of the Examples in acid addition salt form. In yet a further embodiment, the invention relates to any one of the compounds of the Examples in pharmaceutically acceptable salt form. In still another embodiment, the invention relates to any one of the compounds of the Examples in pharmaceutically acceptable acid addition salt form.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

The pharmaceutically acceptable salts of the present invention can be synthesized from an acidic moiety, by conventional chemical methods. Generally, such salts can be prepared by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Furthermore, the compounds of the present invention, including their salts, may also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

The compounds of the present invention, including salts, hydrates and solvates thereof, may inherently or by design form polymorphs.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$ $^{31}P$, $^{32}P$, $^{35}S$, $^{36}Cl$, $^{125}I$ respectively. The invention includes various isotopically labeled compounds as defined herein, for example those into which radioactive isotopes, such as $^{3}H$ and $^{14}C$, or those into which non-radioactive isotopes, such as $^{2}H$ and $^{13}C$ are present. Such isotopically labelled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the present invention may be synthesized by synthetic routes that include processes analogous to those well-known in the chemical arts, particularly in light of the description contained herein. The starting materials are generally available from commercial sources such as Sigma-Aldrich or are readily prepared using methods well known to those skilled in the art (e.g., prepared by methods generally described in Louis F. Fieser and Mary Fieser, Reagents for Organic Synthesis, v. 1-19, Wiley, N.Y.(1967-1999 ed.), or Beilsteins Handbuch der organischen Chemie, 4, Aufl. ed. Springer-Verlag, Berlin, including supplements (also available via the Beilstein online database)).

For illustrative purposes, the reaction schemes depicted below provide potential routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In a further aspect, the invention relates to a process for the preparation of a compound of the formula (I), in free form or in pharmaceutically acceptable salt form, comprising
(a) the reaction of a compound of the formula (II)

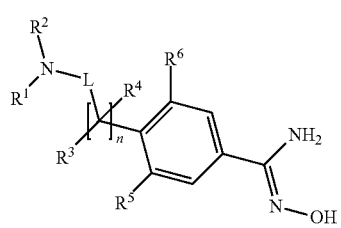

(II)

in which L, $R^1$, $R^2$, $R^3$, $R^4$, $R^5$, $R^6$ and n are as defined for formula (I), with trifluoroacetic acid anhydride, or
(b) the reaction of a compound of the formula (III)

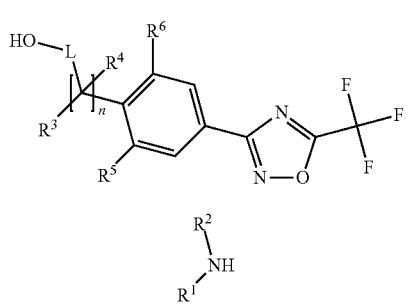

(III)

(IV)

in which L, $R^3$, $R^4$, $R^5$, $R^6$ and n are as defined for formula (I), with a compound of formula (IV), in which $R^1$ and $R^2$ are as defined for formula (I), and thereafter
i) the optional reduction, oxidation or other functionalisation of the resulting compound,
ii) the cleavage of any protecting group(s) present,
iii) the recovery of the so obtainable compound of the formula (I) in free form or in pharmaceutically acceptable salt form, and/or
iv) the optional separation of mixtures of optically active isomers into their individual optically active isomeric forms.

The above reactions can be effected according to conventional methods. For example, the reaction described in step (a) may be carried out in the presence of a suitable organic solvent, for example pyridine or tetrahydrofuran, and at a suitable temperature, for example 10 to 100° C., more suitably 50 to 100° C.

The reaction described in step (b) may be carried out using a suitable coupling agent, for example TFFH (Tetramethylfluoroformamidinium hexafluorophosphate), HATU O-(7-Azabenzotriazol-1-yl)-N,N,N',N'-tetramethyluronium hexafluorophosphate, COMU (1-Cyano-2-ethoxy-2-oxoethylidenaminooxy)dimethylamino-morpholino-carbenium hexafluorophosphate) or DCC (dicyclohexylcarbodiimide), HOBt (1-Hydroxybenzotriazol), or by in situ activation with oxalyl chloride. The reaction is further carried out in the presence of a suitable solvent, for example DCM, DMF or NMP, a suitable base, for example DIPEA or NMM, and at a suitable temperature. When using TFFH, HATU, COMU, DCC or HOBt, a suitable temperature would be, for example 10 to 90° C. When using oxalyl chloride, a suitable temperature would be 0° C. to room temperature.

Compounds of formula (II) may be prepared according to Scheme 1 below from compounds of formula (V) which are described in the literature, are commercially available or can be made using methods known to those skilled in the art.

Scheme 1: general procedure for the synthesis of compounds of formula (II):

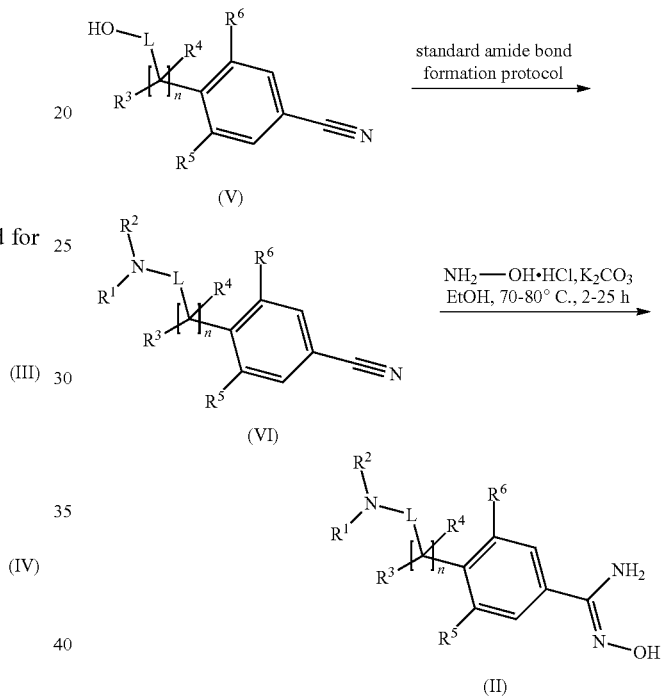

Compounds of formula (III) may be prepared according to Scheme 2 below from compounds of formula (V).

Scheme 2: general procedure for the synthesis of compounds of formula (III):

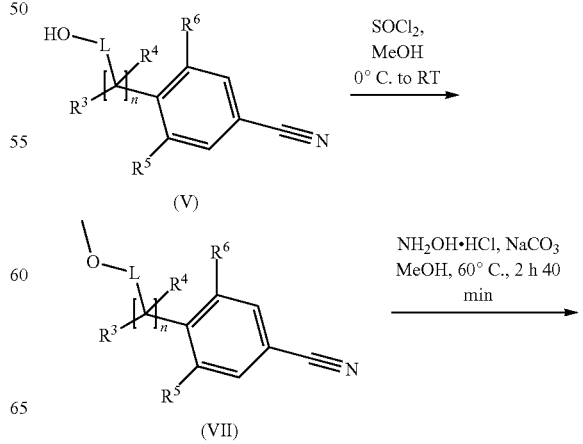

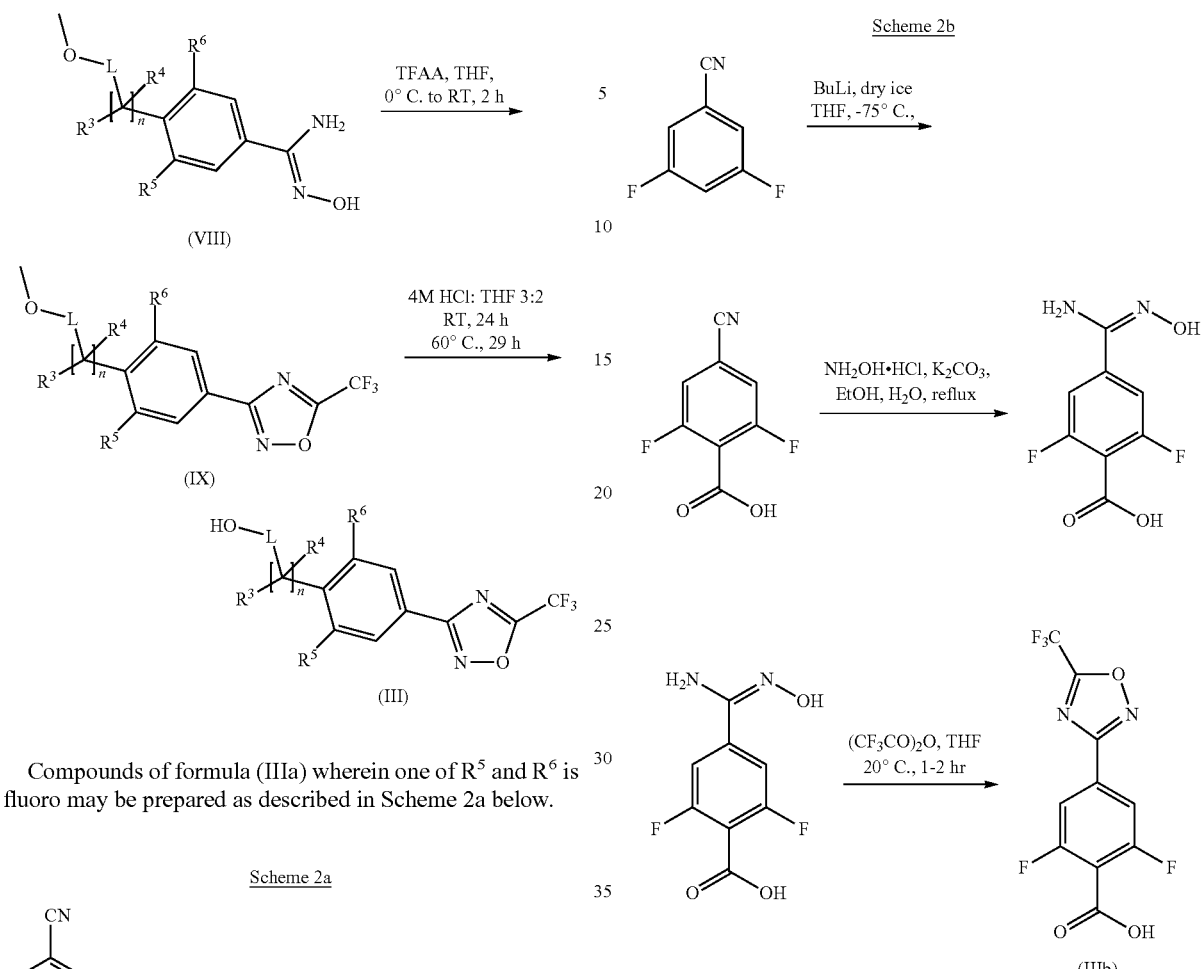

Compounds of formula (IIIa) wherein one of $R^5$ and $R^6$ is fluoro may be prepared as described in Scheme 2a below.

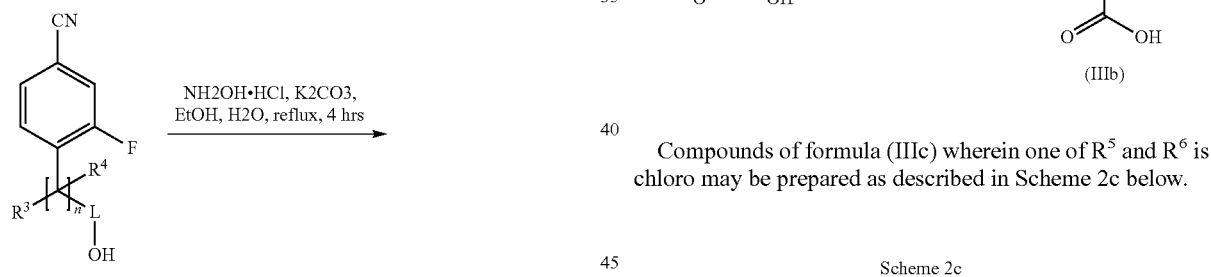

Compounds of formula (IIIb) wherein L represents —C(=O)—, n represents 0 and both of $R^5$ and $R^6$ are fluoro may be prepared as described in Scheme 2b below.

Compounds of formula (IIIc) wherein one of $R^5$ and $R^6$ is chloro may be prepared as described in Scheme 2c below.

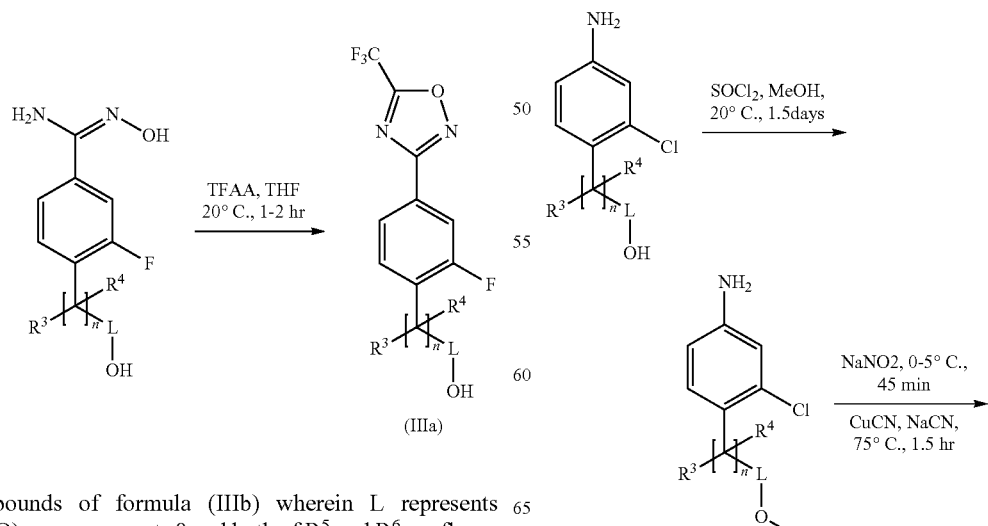

29
-continued

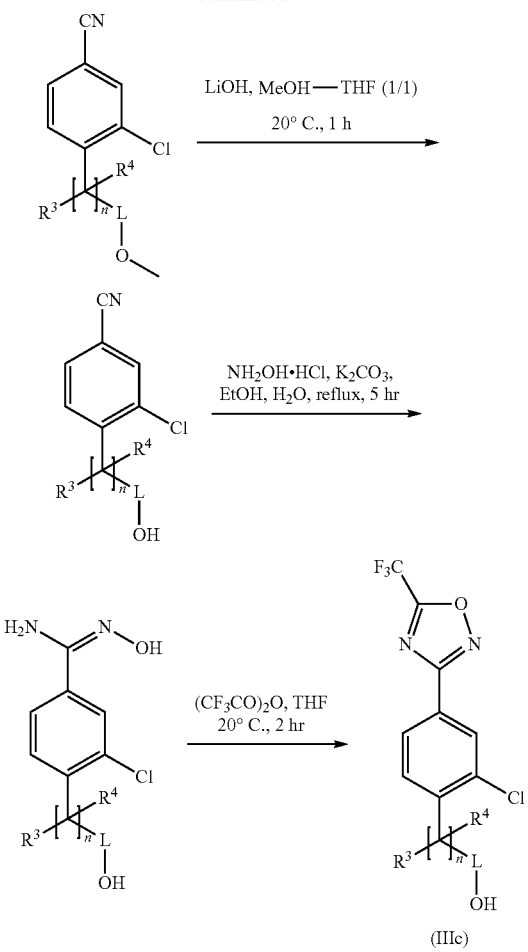

Compounds of formula (IV) are described in the literature, are commercially available, for example from Fluka or Bachem (in Boc-protected form), can be made using methods known to those skilled in the art, or can be made in accordance with the procedures described in the Examples or by procedures analogous thereto. For example, chiral compounds of formula (IVa) where $R^{1a}$ represents $C_{1-4}$alkyl or benzyl can be made according to Scheme 3.

Scheme 3: general procedure for the synthesis of chiral compounds of formula (IVa):

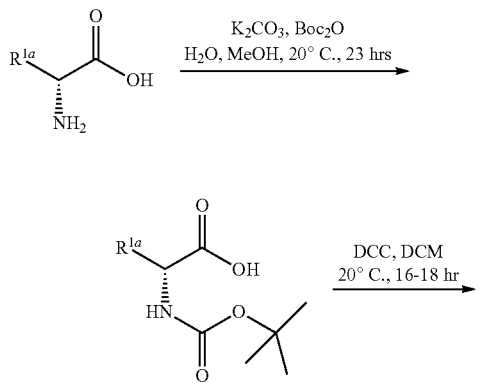

30
-continued

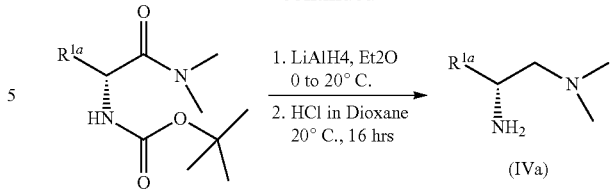

The further optional reduction, oxidation or other functionalisation of compounds of formula (I) may be carried out according to methods well know to those skilled in the art.

Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (Methods of Organic Chemistry), Houben Weyl, 4th edition, Volume 15/I, Georg Thieme Verlag, Stuttgart 1974, and in H.-D. Jakubke and H. Jeschkeit, "Aminosäuren, Peptide, Proteine" (Amino acids, Peptides, Proteins), Verlag Chemie, Weinheim, Deerfield Beach, and Basel 1982. A characteristic of protecting groups is that they can be removed readily (i.e. without the occurrence of undesired secondary reactions) for example by solvolysis, reduction, photolysis or alternatively under physiological conditions (e.g. by enzymatic cleavage).

Salts of compounds of the present invention having at least one salt-forming group may be prepared in a manner known to those skilled in the art. For example, acid addition salts of compounds of the present invention are obtained in customary manner, e.g. by treating the compounds with an acid or a suitable anion exchange reagent.

Salts can be converted into the free compounds in accordance with methods known to those skilled in the art and as described in the Examples. Acid addition salts can be converted, for example, by treatment with a suitable basic agent.

For those compounds containing an asymmetric carbon atom, the compounds exist in individual optically active isomeric forms or as mixtures thereof, e.g. as racemic or diastereomeric mixtures. Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Enantiomers can also be separated by use of a commercially available chiral HPLC column.

The invention further includes any variant of the present processes, in which the reaction components are used in the form of their salts or optically pure material. Compounds of the invention and intermediates can also be converted into each other according to methods generally known to those skilled in the art.

Compounds of the formula (I), in free form or in pharmaceutically acceptable salt form, herein-after often referred to as "agents of the invention", exhibit valuable pharmacological properties, when tested in vitro, and may, therefore, be useful in medicaments, in therapy or for use as research chemicals, for example as tool compounds.

Biological Assays

The agents of the invention are inhibitors of HDAC4. The inhibiting properties of a compound of the invention towards HDAC4 versus HDAC1 and HDAC6 can be evaluated in the assays described below.

Test 1: HDAC4 Assay Description

Human recombinant HDAC4 was expressed in full length form (aa 2-1084) in Sf9 insect cells (obtained from ATCC) using baculovirus generated with Bac-to-Bac system (Invitrogen). Test compounds were serially diluted to reach final test concentrations from 0.003 µM to 100 µM. HDAC4 and test compounds were incubated in 25 mM Tris buffer pH 8.0 containing 137 mM NaCl, 2.7 mM KCl, 1 mM $MgCl_2$ and 0.05% (w/v) bovine serum albumine for 2 hours at room temperature in presence of 10 µM of acetyl-Gly-Ala-Lys(E-trifluoroacetyl)-AMC (AMC=7-amino-4-methyl coumarin) in a final volume of 200 µl. Control wells with HDAC4 only (positive control) and without HDAC4 (negative control) were included on the microplate. Bovine trypsin (10 µl of a 0.4 mg/ml solution) was added and the plate incubated for additional 15 minutes at room temperature. The plate was placed in a fluorescence microplate reader, and read at an excitation wavelength of 360 nm and an emission wavelength of 450 nm with a cut-off filter of 435 nm. Fluorescence values for all wells containing HDAC4 (positive control and wells with test compound) were corrected by subtracting negative control fluorescence values, and $IC_{50}$ values were calculated by fitting the dose-response curves to a 4-parameter logistic function.

Test 2: HDAC4 Assay Description

Human recombinant HDAC4 was expressed in full length form (aa 2-1084) in Sf9 insect cells (obtained from ATCC) using baculovirus generated with Bac-to-Bac system (Invitrogen). Test compounds were serially diluted to reach final test concentrations from 0.000128 µM to 10 µM. HDAC4 and test compounds were incubated in 25 mM Tris buffer pH 8.0 containing 137 mM NaCl, 2.7 mM KCl, 1 mM $MgCl_2$, 0.05% (w/v) bovine serum albumine and 0.005% (v/v) Triton-X-100 for 2 hours at room temperature in presence of 5 µM of acetyl-Gly-Ala-Lys(ε-trifluoroacetyl)-AMC (AMC=7-amino-4-methyl coumarin) in a final volume of 9 µl. Control wells with HDAC4 only (positive control) and without HDAC4 (negative control) were included on the microplate. Bovine trypsin (4.5 µl of a 300 nM solution) was added and the plate incubated for additional 15 minutes at room temperature. The plate was placed in a fluorescence microplate reader, and read at an excitation wavelength of 360 nm and an emission wavelength of 450 nm with a 10 nm bandpath. Fluorescence values for all wells containing HDAC4 (positive control and wells with test compound) were corrected by subtracting negative control fluorescence values, and $IC_{50}$ values were calculated by fitting the dose-response curves to a 4-parameter logistic function.

Test 3: HDAC1 Assay Description

A similar assay procedure as described in Test 2 was used for HDAC1. Human recombinant full length HDAC1 expressed in a baculovirus expression system was purchased from BPS BioSciences (San Diego, Calif., U.S.A.). The substrate used in the HDAC1 assay was 5 µM of acetyl-Gly-Ala-Lys(acetyl)-AMC.

Test 4: HDAC6 Assay Description

A similar assay procedure as described in Test 2 was used for HDAC6. Human recombinant full length HDAC6 expressed in a baculovirus expression system was purchased from BPS BioSciences (San Diego, Calif., U.S.A.). The substrate used in the HDAC1 assay was 5 µM of acetyl-Gly-Ala-Lys(acetyl)-AMC.

The compounds of the Examples showed the $IC_{50}$ values presented in Table 1 below when tested in the HDAC assays. HDAC4 $IC_{50}$ values were obtained using Test 2, except those values indicated by an asterisk which were obtained using Test 1. NT=Not Tested

TABLE 1

| Example Number | HDAC1 $IC_{50}$ (µM) | HDAC4 $IC_{50}$ (µM) | HDAC6 $IC_{50}$ (µM) |
|---|---|---|---|
| 1 | >10 | 0.36 | >10 |
| 2 | >10 | 0.53 | 3.2 |
| 3 | >10 | 1.9 | >10 |
| 4 | >10 | 0.62 | 7.9 |
| 5 | >10 | 0.97 | 3.1 |
| 6 | >10 | 0.63 | 3.2 |
| 7 | >10 | 0.96 | 6.9 |
| 8 | >10 | 0.58 | 7.6 |
| 9 | >10 | 0.85 | 5.5 |
| 10 | >10 | 1.3 | 5.6 |
| 11 | >10 | 1.1 | 8.9 |
| 12 | >10 | 0.43 | 4.1 |
| 13 | >10 | 0.66 | 8.9 |
| 14 | >10 | 0.9 | >10 |
| 15 | >10 | 0.99 | >10 |
| 16 | >10 | 1.4 | 6.8 |
| 17 | >10 | 1.4 | 8.6 |
| 18 | >10 | 0.39 | >10 |
| 19 | NT | 0.12* | NT |
| 20 | >10 | 1 | >10 |
| 21 | >10 | 0.73 | 5.7 |
| 22 | >10 | 0.87 | 4.8 |
| 23 | >10 | 1.5 | 6 |
| 24 | >10 | 0.77 | >10 |
| 25 | >10 | 0.47 | 6.5 |
| 26 | >10 | 0.61 | 3.2 |
| 27 | >10 | 1.2 | >10 |
| 28 | >10 | 0.35 | 7.7 |
| 29 | >10 | 1.2 | >10 |
| 30 | >10 | 6.4 | >10 |
| 31 | 7.6 | 0.08 | 7.05 |
| 32 | >10 | 4.4 | >10 |
| 33 | >10 | 0.4 | >10 |
| 34 | >10 | 0.75 | >10 |
| 35 | >10 | 6.7 | >10 |
| 36 | >10 | 2.7 | >10 |
| 37 | >10 | 0.34 | >10 |
| 38 | >10 | 0.3 | 3.9 |
| 39 | >10 | 1.2 | >10 |
| 40 | >10 | 0.46 | 4.6 |
| 41 | NT | 1.50* | NT |
| 42 | >10 | 4.2 | >10 |
| 43 | >10 | 0.29 | >10 |
| 44 | >10 | 0.38 | 5.7 |
| 45 | >10 | 4.2 | >10 |
| 46 | >10 | 0.78 | 3.3 |
| 47 | >10 | 0.054 | 2.1 |
| 48 | >10 | 0.14 | 4.8 |
| 49 | >10 | 0.99 | >10 |
| 50 | >10 | 0.62 | 7.2 |
| 51 | >10 | 0.09 | 10 |
| 52 | >10 | 3.2 | >10 |
| 53 | >10 | 0.026 | >10 |
| 54 | >10 | 2 | >10 |
| 55 | >10 | 2.8 | >10 |
| 56 | >10 | 0.55 | 6.8 |
| 57 | >10 | 0.52 | 6.5 |

TABLE 1-continued

| Example Number | HDAC1 IC$_{50}$ (μM) | HDAC4 IC$_{50}$ (μM) | HDAC6 IC$_{50}$ (μM) |
|---|---|---|---|
| 58 | >10 | 0.65 | 5.5 |
| 59 | >10 | 1.4 | >10 |
| 60 | >10 | 2.5 | 2.2 |
| 61 | >10 | 0.79 | 7.1 |
| 62 | >10 | 0.6 | 2.3 |
| 63 | >10 | 0.78 | >10 |
| 64 | >10 | 0.51 | >10 |
| 65 | >10 | 0.24 | 4.6 |
| 66 | >10 | 0.33 | 5.8 |
| 67 | >10 | 0.16 | 8.3 |
| 68 | >10 | 0.17 | 5.3 |
| 69 | >10 | 0.29 | 6.8 |
| 70 | NT | 0.09* | NT |
| 71 | >10 | 0.92 | >10 |
| 72 | >10 | 0.14 | >10 |
| 73 | >10 | 0.053 | 6.1 |
| 74 | >10 | 0.19 | 8.6 |
| 75 | >10 | 0.16 | >10 |
| 76 | >10 | 0.15 | 3.9 |
| 77 | >10 | 0.35 | >10 |
| 78 | >10 | 0.03 | 7 |
| 79 | >10 | 0.8 | >10 |
| 80 | >10 | 0.47 | >10 |
| 81 | >10 | 0.034 | >10 |
| 82 | >10 | 0.12 | >10 |
| 83 | >10 | 0.015 | >10 |
| 84 | >10 | 0.49 | >10 |
| 85 | >10 | 0.048 | >10 |
| 86 | >10 | 0.026 | >10 |
| 87 | >10 | 0.3 | >10 |
| 88 | >10 | 0.012 | 4.7 |
| 89 | >10 | 0.045 | >10 |
| 90 | >10 | 0.44 | 2.5 |
| 91 | >10 | 0.5 | 5.1 |
| 92 | >6.8 | 0.085 | 4 |
| 93 | >10 | 0.19 | 4.9 |
| 94 | >10 | 0.52 | >10 |
| 95 | >10 | 0.16 | 6.9 |
| 96 | 7.0 | 0.096 | 0.4 |
| 97 | >10 | 0.43 | 4.4 |
| 98 | >10 | 0.36 | 6.4 |
| 99 | >10 | 1.35 | 9.9 |
| 100 | NT | 0.07* | NT |
| 101 | >10 | 2.95 | >10 |
| 102 | >10 | 3.2 | >10 |
| 103 | >10 | 0.08 | 0.7 |
| 104 | >10 | 0.84 | 0.77 |
| 105 | 3.6 | 0.27 | 0.47 |
| 106 | NT | 0.2* | NT |
| 107 | 6.2 | 0.79 | 0.46 |
| 108 | 5 | 0.093 | 0.74 |
| 109 | >10 | 0.097 | 0.44 |
| 110 | >10 | 0.2 | 2 |
| 111 | >10 | 0.29 | 0.58 |
| 112 | >10 | 0.82 | 9.1 |
| 113 | >10 | 0.3 | 6.2 |
| 114 | >10 | 0.63 | 9.1 |
| 115 | >10 | 2.7 | >10 |
| 116 | >10 | 0.16 | 3.1 |
| 117 | 6.7 | 0.11 | 1.5 |
| 118 | >10 | 0.22 | 4.7 |
| 119 | >10 | 0.036 | >10 |
| 120 | >10 | 0.21 | >10 |
| 121 | >10 | 0.015 | 4.4 |
| 122 | 9 | 0.085 | 2.4 |
| 123 | >10 | 0.0076 | >10 |
| 124 | >10 | 0.31 | >10 |
| 125 | >10 | 0.053 | >10 |
| 126 | >10 | 0.0089 | 3.9 |
| 127 | >10 | 0.044 | >10 |
| 128 | >10 | 0.026 | 4.5 |
| 129 | 9.05 | 0.013 | 3 |
| 130 | >10 | 0.011 | 9.1 |
| 131 | 6.55 | 0.01 | 7.5 |
| 132 | 9.2 | 0.005 | 8.3 |
| 133 | NT | 0.048* | NT |
| 134 | >10 | 0.0098 | >10 |
| 135 | >10 | 0.01 | >10 |
| 136 | >10 | 0.0089 | >10 |
| 137 | 2.2 | 0.00097 | 3 |
| 138 | >10 | 0.0045 | >10 |
| 139 | 4 | 0.001 | 9.6 |
| 140 | NT | 0.072* | NT |
| 141 | 4.2 | 0.0014 | 1.4 |
| 142 | >10 | 0.0072 | 5.4 |
| 143 | 5.8 | 0.0012 | 3.3 |
| 144 | >10 | 0.18 | >10 |
| 145 | 2.4 | 0.00075 | 3.7 |
| 146 | 5.1 | 0.0016 | 2.4 |
| 147 | >10 | 0.3 | 6.7 |
| 148 | >10 | 0.38 | 3.2 |
| 149 | >10 | 0.14 | 6.4 |
| 150 | 1.2 | 0.0011 | 3.1 |
| 151 | 2.7 | 0.0018 | 2.6 |
| 152 | >10 | 0.0084 | 2.4 |
| 153 | 1.8 | 0.0036 | 3 |
| 154 | >10 | 0.11 | 7.2 |
| 155 | 2.9 | 0.012 | 2.6 |
| 156 | 2.9 | 0.00085 | 2.3 |
| 157 | 6.1 | 0.04 | 3.4 |
| 158 | 8.8 | 0.36 | 1.8 |

Due to their ability to inhibit HDAC4 activity, agents of the invention may be useful in the treatment or prevention neurodegeneration arising from cerebral ischemia; an acute, traumatic or chronic degenerative process of the nervous system, such as Parkinson's disease, Down's syndrome, dementia, e.g. senile dementia, dementia with Lewy bodies or a frontotemporal dementia, a cognitive disorder, cognitive impairment, e.g. mild cognitive impairment, memory impairment, an amyloid neuropathy, a peripheral neuropathy, Alzheimer's disease, Gerstmann-Straeussler-Scheinker syndrome, Niemann-Pick disease, e.g. Niemann-Pick type C disease, brain inflammation, a brain, spinal cord or nerve injury, e.g. traumatic brain injury (TBI), a nerve trauma or a brain trauma, vascular amyloidosis, cerebral haemorrhage with amyloidosis, Huntington's chorea, amyotrophic lateral sclerosis, multiple sclerosis or fragile X syndrome; scrapie; cerebral amyloid angiopathy; an encephalopathy, e.g. transmissible spongiform encephalopathy; or stroke. Agents of the invention may also be useful in enhancing cognition, e.g. in a subject suffering from a dementing condition, such as Alzheimer's disease; or as ligands, e.g. radioligands or positron emission tomography (PET) ligands.

Due to their ability to inhibit HDAC4 activity, agents of the invention may also be useful in the treatment or prevention metabolic syndrome (including but not limited to dyslipidemia, obesity and insulin resistance, hypertension, microalbuminemia, hyperuricaemia, and hypercoaguability), Syndrome X, diabetes, insulin resistance, decreased glucose tolerance, non-insulin-dependent diabetes mellitus, Type II diabetes, Type I diabetes, diabetic complications, body weight disorders (including but not limited to obesity, overweight, cachexia, bulimia and anorexia), weight loss, wasting disorders, body mass index and leptin-related diseases.

Due to their ability to inhibit HDAC4 activity, agents of the invention may also be useful in the treatment or prevention of muscular atrophy, such as that found as a result of: the catabolic side effects of glucocorticoids; chronic fatigue syndrome; chronic myalgia; bone fracture; acute fatigue syndrome; immobilization due to bed rest, as when a patient undergoes elective surgery or an extended hospital stay due to disease; cachexia; chronic catabolic state; eating disorders; side effects of chemotherapy; wasting secondary to fractures;

wasting in connection with chronic obstructive pulmonary disease (COPD), chronic liver disease, AIDS, weightlessness, cancer cachexia, burn and trauma recovery, chronic catabolic state such as coma, eating disorders such as anorexia and chemotherapy; wasting in connection with renal failure; wasting as a result of liver failure; low testosterone or low IGF1 or low growth hormone levels. The therapy may also be useful in settings of lipodistrophy; obesity; sarcopenia—which is defined as age-related frailty or age-related loss of muscle; reduced muscle strength and function. The therapy may also be helpful in settings of myositis leading to muscle loss, such as Inclusion Body Myositis, or any of the inflammatory myosites.

For the above-mentioned indications, the appropriate dosage will vary depending on, e.g., the compound employed as active pharmaceutical ingredient, the host, the mode of administration, the nature and severity of the condition, disease or disorder or the effect desired. However, in general, satisfactory results in animals are indicated to be obtained at a daily dosage of from about 0.1 to about 100, preferably from about 1 to about 50, mg/kg of animal body weight. In larger mammals, for example humans, an indicated daily dosage is in the range of from about 0.5 to about 2000, preferably from about 2 to about 200, mg of an agent of the invention conveniently administered, for example, in divided doses up to four times a day or in sustained release form.

An agent of the invention may be administered by any conventional route, in particular enterally, preferably orally, e.g. in the form of a tablet or capsule, or parenterally, e.g. in the form of an injectable solution or suspension.

In a further aspect, the invention relates to a pharmaceutical composition comprising an agent of the invention as active pharmaceutical ingredient in association with at least one pharmaceutically acceptable carrier or diluent and optionally in association with other auxiliary substances, such as inhibitors of cytochrome P450 enzymes, agents preventing the degradation of active pharmaceutical ingredients by cytochrome P450, agents improving or enhancing the pharmacokinetics of active pharmaceutical ingredients, agents improving or enhancing the bioavailability of active pharmaceutical ingredients, and so on, e.g. grapefruit juice, ketoconazole or, preferably, ritonavir. Such a composition may be manufactured in conventional manner, e.g. by mixing its components. Unit dosage forms contain, e.g., from about 0.1 to about 1000, preferably from about 1 to about 500, mg of an agent of the invention.

In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc.

Typically, the pharmaceutical compositions are tablets or gelatin capsules comprising the active ingredient together with
  a) diluents, e.g., lactose, dextrose, sucrose, mannitol, sorbitol, cellulose and/or glycine;
  b) lubricants, e.g., silica, talcum, stearic acid, its magnesium or calcium salt and/or polyethyleneglycol; for tablets also
  c) binders, e.g., magnesium aluminum silicate, starch paste, gelatin, tragacanth, methylcellulose, sodium carboxymethylcellulose and/or polyvinylpyrrolidone; if desired
  d) disintegrants, e.g., starches, agar, alginic acid or its sodium salt, or effervescent mixtures; and/or
  e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurized container, pump, spray, atomizer or nebuliser, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

In accordance with the foregoing, in a further aspect, the invention relates to an agent of the invention for use as a medicament, for example for the treatment or prevention of neurodegeneration, muscle atrophy or metabolic syndrome. In a further embodiment, the invention relates to an agent of the invention for use in the treatment of a disease or disorder mediated by HDAC4 activity. In one embodiment, the invention relates to an agent of the invention for use in the treatment of Huntington's disease, muscle atrophy or diabetes.

In a further aspect, the invention relates to the use of an agent of the invention as an active pharmaceutical ingredient in a medicament, for example for the treatment or prevention of neurodegeneration, muscle atrophy or metabolic syndrome. In a further embodiment, the invention relates to the use of an agent of the invention as an active pharmaceutical ingredient in a medicament for the treatment or prevention of a disease or disorder mediated by HDAC4 activity. In one embodiment, the invention relates to the use of an agent of the invention as an active pharmaceutical ingredient in a medicament for the treatment or prevention of Huntington's disease, muscle atrophy or diabetes.

In a further aspect, the invention relates to the use of an agent of the invention for the manufacture of a medicament for the treatment or prevention of neurodegeneration, muscle atrophy or metabolic syndrome. In a further embodiment, the invention relates to the use of an agent of the invention for the manufacture of a medicament for the treatment or prevention of a disease or disorder mediated by HDAC4 activity. In one embodiment, the invention relates to the use of an agent of the invention for the manufacture of a medicament for the treatment or prevention of Huntington's disease, muscle atrophy or diabetes.

In a further aspect, the invention relates to a method for the treatment or prevention of neurodegeneration, muscle atrophy or metabolic syndrome, in a subject in need of such treatment or prevention, which method comprises administering to such subject an effective amount of an agent of the invention. In one embodiment, the invention relates to a method of modulating HDAC4 activity in a subject, wherein the method comprises administering to the subject a therapeutically effective amount of an agent of the invention. In another embodiment, the invention relates to a method for the treatment or prevention of a disease mediated by HDAC4 activity, in a subject in need of such treatment or prevention, which method comprises administering to such subject an effective amount of an agent of the invention. In yet another embodiment, the invention relates to a method for the treatment or prevention of Huntington's disease, muscle atrophy or diabetes, in a subject in need of such treatment or prevention, which method comprises administering to such subject an effective amount of an agent of the invention.

An agent of the invention can be administered as sole active pharmaceutical ingredient or as a combination with at least one other active pharmaceutical ingredient effective, e.g., in the treatment or prevention of neurodegeneration, muscle atrophy or metabolic syndrome. Such a pharmaceutical combination may be in the form of a unit dosage form, which unit dosage form comprises a predetermined quantity of each of the at least two active components in association with at least one pharmaceutically acceptable carrier or diluent. Alternatively, the pharmaceutical combination may be in the form of a package comprising the at least two active components separately, e.g. a pack or dispenser-device adapted for the concomitant or separate administration of the at least two active components, in which these active components are separately arranged. In a further aspect, the invention relates to such pharmaceutical combinations.

In a further aspect, the invention therefore relates to a pharmaceutical combination comprising a therapeutically effective amount of an agent of the invention and a second drug substance, for simultaneous or sequential administration.

In one embodiment, the invention provides a product comprising an agent of the invention and at least one other therapeutic agent as a combined preparation for simultaneous, separate or sequential use in therapy. In one embodiment, the therapy is the treatment of a disease or condition mediated by HDAC4 activity.

In one embodiment, the invention provides a pharmaceutical composition comprising an agent of the invention and another therapeutic agent(s). Optionally, the pharmaceutical composition may comprise a pharmaceutically acceptable carrier or diluent, as described above.

In one embodiment, the invention provides a kit comprising two or more separate pharmaceutical compositions, at least one of which contains an agent of the invention. In one embodiment, the kit comprises means for separately retaining said compositions, such as a container, divided bottle, or divided foil packet. An example of such a kit is a blister pack, as typically used for the packaging of tablets, capsules and the like. The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the agent of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent. Accordingly, the invention provides an agent of the invention for use in the treatment of a disease or condition mediated by HDAC4 activity, wherein the medicament is prepared for administration with another therapeutic agent. The invention also provides the use of another therapeutic agent for treating a disease or condition mediated by HDAC4 activity, wherein the medicament is administered with an agent of the invention.

The invention also provides an agent of the invention for use in a method of treating a disease or condition mediated HDAC4 activity, wherein the agent of the invention is prepared for administration with another therapeutic agent. The invention also provides another therapeutic agent for use in a method of treating a disease or condition mediated by HDAC4 activity, wherein the other therapeutic agent is prepared for administration with an agent of the invention. The invention also provides an agent of the invention for use in a method of treating a disease or condition mediated by HDAC4 activity, wherein the agent of the invention is administered with another therapeutic agent. The invention also provides another therapeutic agent for use in a method of treating a disease or condition mediated by HDAC4 activity, wherein the other therapeutic agent is administered with an agent of the invention.

The invention also provides the use of an agent of the invention for treating a disease or condition mediated by HDAC4 activity, wherein the patient has previously (e.g. within 24 hours) been treated with another therapeutic agent. The invention also provides the use of another therapeutic agent for treating a disease or condition mediated by HDAC4 activity, wherein the patient has previously (e.g. within 24 hours) been treated with an agent of the invention.

In one embodiment, the invention relates to a compound of the invention in combination with another therapeutic agent wherein the other therapeutic agent is selected from:
(a) acetylcholinesterase inhibitors, such as donepezil (Aricept™), rivastigmine (Exelon™) and galantamine (Razadyne™);
(b) glutamate antagonists, such as memantine (Namenda™);
(c) antidepressant medications for low mood and irritability, such as citalopram (Celexa™), fluoxetine (Prozac™), paroxeine (Paxil™), sertraline (Zoloft™) and trazodone (Desyrel™);
(d) anxiolytics for anxiety, restlessness, verbally disruptive behavior and resistance, such as lorazepam (Ativan™) and oxazepam (Serax™);
(e) antipsychotic medications for hallucinations, delusions, aggression, agitation, hostility and uncooperativeness, such as aripiprazole (Abilify™), clozapine (Clozaril™), haloperidol (Haldol™), olanzapine (Zyprexa™), quetiapine (Seroquel™), risperidone (Risperdal™) and ziprasidone (Geodon™);
(f) mood stabilizers, such as carbamazepine (Tegretol™) and divalproex (Depakote™);
(g) nicotinic apha-7 agonists;
(h) mGluR5 antagonists;
(i) H3 agonists; and
(j) amyloid therapy vaccines.

Thus, in another embodiment, the invention provides a pharmaceutical composition comprising:
i) a compound of the invention, or a pharmaceutically acceptable salt thereof; and
ii) at least one compound selected from:
(a) acetylcholinesterase inhibitors,
(b) glutamate antagonists,
(c) antidepressant medications,
(d) anxiolytics,
(e) antipsychotic medications,
(f) mood stabilizers,
(g) nicotinic apha-7 agonists,
(h) mGluR5 antagonists,
(i) H3 agonists; and
ii) one or more pharmaceutically acceptable carrier or diluent.

In another embodiment, the invention relates to a compound of the invention, or a pharmaceutically acceptable salt thereof, in combination with another therapeutic agent wherein the other therapeutic agent is selected from:
a) antidiabetic agents, such as insulin, insulin derivatives and mimetics; insulin secretagogues such as the sulfonylureas, e.g., Glipizide, glyburide and Amaryl; insulinotropic sulfonylurea receptor ligands such as meglitinides, e.g., nateglinide and repaglinide; protein tyrosine phosphatase-1B (PTP-1B) inhibitors such as PTP-112; GSK3 (glycogen synthase kinase-3) inhibitors such as SB-517955, SB-4195052, SB-216763, N,N-57-05441 and N,N-57-05445; RXR ligands such as GW-0791 and AGN-194204; sodium-dependent glucose cotransporter inhibitors such as T-1095; glycogen phosphorylase A inhibitors such as BAY R3401; biguanides such as metformin; alpha-glucosidase inhibitors such as acarbose; GLP-1 (glucagon like peptide-1), GLP-1 analogs such as Exendin-4 and GLP-1 mimetics; and DPPIV (dipeptidyl peptidase IV) inhibitors such as vildagliptin;

b) hypolipidemic agents such as 3-hydroxy-3-methyl-glutaryl coenzyme A (HMG-CoA) reductase inhibitors, e.g., lovastatin, pitavastatin, simvastatin, pravastatin, cerivastatin, mevastatin, velostatin, fluvastatin, dalvastatin, atorvastatin, rosuvastatin and rivastatin; squalene synthase inhibitors; FXR (farnesoid X receptor) and LXR (liver X receptor) ligands; cholestyramine; fibrates; nicotinic acid bile acid binding resins such as cholestyramine; fibrates; nicotinic acid and other GPR109 agonists; cholesterol absorption inhibitors such as ezetimibe; CETP inhibitors (cholesterol-ester-transfer-protein inhibitors), and aspirin;

c) anti-obesity agents such as orlistat, sibutramine and Cannabinoid Receptor 1 (CB1) antagonists e.g. rimonabant; and d) anti-hypertensive agents, e.g., loop diuretics such as ethacrynic acid, furosemide and torsemide; angiotensin converting enzyme (ACE) inhibitors such as benazepril, captopril, enalapril, fosinopril, lisinopril, moexipril, perinodopril, quinapril, ramipril and trandolapril; inhibitors of the Na—K-ATPase membrane pump such as digoxin; neutralendopeptidase (NEP) inhibitors; ACE/NEP inhibitors such as omapatrilat, sampatrilat and fasidotril; angiotensin II antagonists such as candesartan, eprosartan, irbesartan, losartan, telmisartan and valsartan, in particular valsartan; renin inhibitors such as ditekiren, zankiren, terlakiren, aliskiren, RO 66-1132 and RO-66-1168; β-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists; and aldosterone synthase inhibitors.

e) agonists of peroxisome proliferator-activator receptors, such as fenofibrate, pioglitazone, rosiglitazone, tesaglitazar, BMS-298585, L-796449, the compounds specifically described in the patent application WO 2004/103995 i.e. compounds of examples 1 to 35 or compounds specifically listed in claim 21, or the compounds specifically described in the patent application WO 03/043985 i.e. compounds of examples 1 to 7 or compounds specifically listed in claim 19 and especially (R)-1-{4-[5-methyl-2-(4-trifluoromethyl-phenyl)-oxazol-4-ylmethoxy]-benzenesulfonyl}-2,3-dihydro-1H-indole-2-carboxylic or a salt thereof.

Thus, in one embodiment, the invention provides a pharmaceutical composition comprising:
i) a compound of the invention, or a pharmaceutically acceptable salt thereof; and
ii) at least one compound selected from:
a) antidiabetic agents,
b) hypolipidemic agents,
c) anti-obesity agents,
d) anti-hypertensive agents,
e) agonists of peroxisome proliferator-activator receptors; and
ii) one or more pharmaceutically acceptable carrier or diluent.

Other specific anti-diabetic compounds are described by Patel Mona in *Expert Opin Investig Drugs*, 2003, 12(4), 623-633, in the FIGS. 1 to 7.

In another embodiment, the invention relates to a compound of the invention, or a pharmaceutically acceptable salt thereof, in combination with another therapeutic agent wherein the other therapeutic agent is selected from:
a) inhibitors of the myostatin receptor(s),
b) activators of the IGF1 receptor,
c) activators of the beta2 adrenergic receptor,
d) inhibitors of TNF, and
e) activators of the androgen receptor.

Thus, in one embodiment, the invention provides a pharmaceutical composition comprising:
i) a compound of the invention, or a pharmaceutically acceptable salt thereof; and
ii) at least one compound selected from:
a) inhibitors of the myostatin receptor(s);
b) activators of the IGF1 receptor;
c) activators of the beta2 adrenergic receptor;
d) inhibitors of TNF; and
e) activators of the androgen receptor; and
ii) one or more pharmaceutically acceptable carrier or diluent.

The structure of the therapeutic agents identified by code numbers, generic or trade names may be taken from the actual edition of the standard compendium "The Merck Index" or from databases, e.g., Patents International (e.g. IMS World Publications).

EXAMPLES

NMR Methods

Proton spectra are recorded on a Bruker 400 MHz ultrashield spectrometer unless otherwise noted. Chemical shifts are reported in ppm relative to methanol ($\delta$ 3.31), dimethyl sulfoxide ($\delta$ 2.50), or chloroform ($\delta$ 7.26). A small amount of the dry sample (2-5 mg) is dissolved in an appropriate deuterated solvent (0.7 mL). The shimming is automated and the spectra is obtained with 32 or more scans.

Chromatography and LC/MS Methods:
Flash Chromatography System: ISCO System, Combi-Flash Companion; IG Instrumenten-Gesellschaft AG. Cartusch System.
HPLC preparative Chromatography System: Waters Prep instrument
LC-MS System (analytical): Waters Alliance HT ($Rt_{MS1-4}$)/Agilent LC 1100 Series ($Rt_{MS5}$)
UPLC-MS System (analytical): Waters Acquity UPLC
LC/MS-Method I: $Rt_{MS1}$
Column: SunFire C18; 20×4.6 mm, 3.5 µm, reverse phase;
Eluent: Water (+0.1% TFA):acetonitrile (+0.1% TFA) from 95:5 to 5:95 in 4 min;
Flow rate: 3 ml/min; temperature 45° C.
LC/MS-Method 2: $Rt_{MS2}$
Column: Ascentis Express C18, 2.4 um, 2.1×30 mm;
Eluent: Water (+0.05% formic acid+3.75 mM ammonium acetate): acetonitrile (+0.04% formic acid) from 98:2 to 2:98 in 1.4 min;
Flow rate: 1.2 ml/min; temperature 50° C.
LC/MS-Method I: $Rt_{MS3}$
Column: SunFire C18; 20×4.6 mm, 3.5 µm, reverse phase;
Eluent: Water (+0.1% TFA): acetonitrile (+0.1% TFA) from 1.5 to 35% in 3.1 min, from 35% to 100% in 0.1 min;
Flow rate: 3 ml/min; temperature 45° C.
LC/MS-Method I: $Rt_{MS4}$
Column: SunFire C18; 20×4.6 mm, 3.5 µm, reverse phase;
Eluent: Water (+0.1% TFA): acetonitrile (+0.1% TFA) from 5:95 to 100:0 in 8 min;
Flow rate: 2 ml/min; temperature 45° C.
LC/MS-Method: $Rt_{MS5}$
Column: Waters Xselect CSH C18, 3.5 um, 4.6×50 mm
Eluent Water (+0.1% TFA); acetonitrile (+0.08% TFA) from 95:5 to 5:95 in 8.5 min, hold for 1 min
Flow rate: 1.0 mL/min at 37° C.
UPLC/MS-Method I: $Rt_{UPLC}$
Column: Water Acquity HSS T3 1.8 um, 2.1×50 mm;
Eluent: Water (+0.05% formic acid+3.75 mM ammonium acetate): acetonitrile (+0.04% formic acid) from 98:2 to 2:98 in 1.4 min;
Flow rate: 1.2 ml/min; temperature 50° C.

Abbreviations:
AcOH acetic acid
ACN acetonitrile
Boc tert-butoxycarbonyl
COMU 1-cyano-2-ethoxy-2-oxoethylidenaminooxy)dimethylamino-morpholino-carbenium hexafluorophosphate
d day(s)
DCM dichloromethane
DCC dicyclohexylcarbodiimide
DMF dimethylformamide
DMSO dimethylsulfoxide
EDC 1-(3-dimethylaminopropyl)-3-ethylcarbodiimide
ESI/MS electrospray ionization/mass spectrometry
EtOAc ethyl acetate
EtOH ethanol
Et$_2$O diethyl ether
eq equivalent
h hour(s)
HATU O-(7-Azabenzotriazol-1-yl)-N,N,N',N'-tetramethyluronium hexafluorophosphate Hept heptanes
Hex hexane
HOBt 1-Hydroxybenzotriazole trihydrate
HPLC high pressure liquid chromatography
HV high vacuum
IC50 concentration of 50% inhibition
i.p. intra-peritoneal (administration)

K Kelvin
LAH lithium aluminium hydride
LCMS liquid chromatography mass spectroscopy
MeOH Methanol
min minute(s)
mL milliliter
MS mass spectroscopy
NBoc nitrogen-bound tert-butyloxycarbonyl group
NMM N-Methylmorpholine
NMP N-Methylpyrrolidone
NMR nuclear magnetic resonance spectrometry
p.o. (oral administration)
quant. quantitative
Rt retention time
rt room temperature
s.c. sub-cutaneous (administration)
THF tetrahydrofuran
TFA trifluoroacetic acid
TFAA trifluoroacetic acid anhydride
TFFH tetramethylfluoroformamidinium hexafluorophosphate
Ts tosyl
UPLC ultra performance liquid chromatography Example 1

N,N-dimethyl-4-(5-(trifluoromethyl)-1,2,4-oxadiazol-3-yl)benzamide

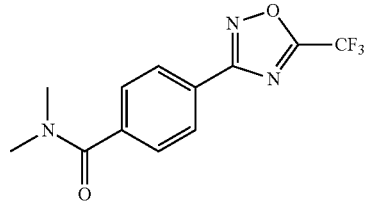 [SMILES: CN(C)C(=O)c1ccc(-c2noc(C(F)(F)F)n2)cc1]

4-(N-hydroxycarbamimidoyl)-N,N-dimethyl-benzamide (100 mg, 0.483 mmol) was dissolved in pyridine (1 mL). TFAA (0.081 mL, 0.579 mmol) was added and the reaction mixture was stirred at 75° C. for 3 h. The reaction mixture was diluted with 25 mL EtOAc and 5 mL water; no phase separation. 10 pipette drops of 0.1 M HCl were added. The phases were separated and the organic phase was washed with 5 mL of water, then 5 mL of brine. Drying over $Na_2SO_4$ gave the crude product. The crude product was subjected to purification by reverse phase prep-HPLC (gradient elution, water/ACN both containing 0.1% TFA). Fractions containing the desired compound were combined and freeze-dried to yield 30 mg as white powder.

$Rt_{MS4}$=3.85 min, ESIMS $[M+H]^+$=286.1
1H NMR (400 MHz, DMSO-$d_6$) δ ppm: 8.13 (d, J=6.85 Hz, 2H), 7.65 (d, J=6.85 Hz, 2 H), 2.97-3.13 (m, 3 H), 2.69-2.97 (m, 3 H).

Intermediate 1a:
4-(N-Hydroxycarbamimidoyl)-N,N-dimethyl-benzamide 4-cyano-N,N-dimethylbenzamide (200 mg, 1.148 mmol), potassium carbonate (952 mg, 6.89 mmol) and hydroxylamine hydrochloride (479 mg, 6.89 mmol) were dissolved in EtOH (11.4 mL). The reaction mixture was stirred at 80° C. for 25 h. The mixture was diluted with EtOAc (50 mL), washed with water (10 mL), water phase extracted with EtOAc (20 mL). Combined organic phases were washed with brine (10 mL) and dried over sodium sulfate. The solvent was removed to give 188 mg of white crystalline needles. The crude material was used without further purification.

Example 2

N-Methyl-4-(5-(trifluoromethyl)-1,2,4-oxadiazol-3-yl)benzamide

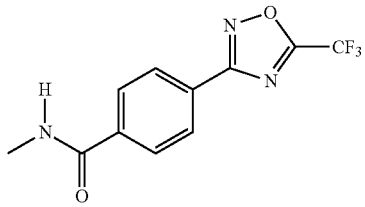 [SMILES: CNC(=O)c1ccc(-c2noc(C(F)(F)F)n2)cc1]

4-(N-hydroxycarbamimidoyl)-N-methyl-benzamide (100 mg, 0.518 mmol) was dissolved in pyridine (1 ml). TFAA (0.086 ml, 0.621 mmol) was added and the reaction mixture was stirred at 75° C. for 3 h. After 3 h, another 0.040 mL TFAA was added and heating was continued for 2 h. The reaction mixture was diluted with 25 mL EtOAc and 5 mL water; no phase separation. 20 pipette drops of 0.1 M HCl were added. The phases were separated and the organic phase was washed with 5 mL of water, then 5 mL of brine. Drying over $Na_2SO_4$ gave the crude product. The crude product was subjected to purification by reverse phase prep-HPLC (gradient elution, water/ACN both containing 0.1% TFA). Fractions containing the desired compound were combined and freeze-dried to yield 49 mg as white powder.

$Rt_{MS4}$=3.63 min, ESIMS $[M+H]^+$=272.1
1H NMR (400 MHz, DMSO-$d_6$) δ ppm: 8.67 (br. s., 1 H), 8.16 (d, J=8.07 Hz, 2 H), 8.05 (d, J=8.07 Hz, 2 H), 2.81 (d, J=4.16 Hz, 3 H).

Intermediate 2a:
4-(N-hydroxycarbamimidoyl)-N-methyl-benzamide

4-Cyano-N-methylbenzamide (200 mg, 1.249 mmol), potassium carbonate (1035 mg, 7.49 mmol) and hydroxylamine hydrochloride (521 mg, 7.49 mmol) were dissolved in EtOH (12.6 mL). The reaction mixture was stirred at 80° C. for 25 h. The reaction mixture was diluted with EtOAc (50 mL), washed with water (10 mL), water phase extracted with EtOAc (20 mL). Combined organic phases were washed with brine (10 mL) and dried over sodium sulfate. The solvent was removed to yield 227 mg of a white powdery solid. The crude material was used without further purification.

Examples 3-11

HATU Coupling General Method

[4-(5-Trifluoromethyl-[1,2,4]oxadiazol-3-yl)-phenyl]-acetic acid (70 mg, 0.257 mmol), DMAP (3.14 mg, 0.026 mmol) and the appropriate amine (–, 0.386 mmol) were dissolve in NMP (0.3 mL), Huenig's Base (135 μL, 0.772 mmol) added and the solution stirred. HATU (147 mg, 0.386 mmol) dissolved in NMP (0.55 mL) was added after 30 minutes and the mixture was stirred overnight. The reaction mixture was subjected to purification by reverse phase prep-HPLC (gradient elution, water/ACN both containing 0.1% TFA). Fractions containing the desired compound were combined and freeze-dried. The resulting material was dissolved in a mix of ACN/MeOH, loaded on a PL-HCO3 MP cartridge (from StratoSpheres™ SPE) and eluted with ACN (3 ml). The eluate was diluted with water (10 ml) and freeze-dried to yield the final compound.

Preparation of [4-(5-trifluoromethyl-[1,2,4]oxadiazol-3-yl)-phenyl]-acetic acid

Intermediate 3a: (4-cyano-phenyl)-acetic acid methylester

Thionyl chloride (1.1 mL, 15.07 mmol) was added to cool MeOH (70 mL) at 0° C. After 5 min 2-(4-cyanophenyl)acetic acid (1 g, 6.21 mmol) was added. After 30 min, cooling was removed and the mixture stirred for 21 h at RT. The solvent was removed and toluene was added and evaporated 3 times to give a sticky yellow solid. The product was used crude for the next step.

$Rt_{MS1}$=1.48 min, ESIMS [M+H]$^+$=176.1, sticky yellow solid

1H NMR (400 MHz, chloroform-d) δ ppm: 7.65 (m, J=8.31 Hz, 2 H), 7.42 (m, J=8.56 Hz, 2 H), 3.69-3.76 (m, 5 H).

Intermediate 3b: [4-(N-hydroxycarbamimidoyl)-phenyl]-acetic acid methyl ester (4-Cyano-phenyl)-acetic acid methylester (1.054 g, 6.02 mmol), hydroxylamine hydrochloride (0.690 g, 9.93 mmol) and sodium bicarbonate (0.834 g, 9.93 mmol) were dissolved in MeOH (12.03 mL) at RT. The mixture was stirred at 60° C. for 5 h, diluted with EtOAc (200 mL) and 40 ml water added. The aqueous layer was extracted with EtOAc (100 mL). The combined organic phases were washed with brine (40 mL) and dried over sodium sulfate. Solvent was removed to yield 1.2 g (5.76 mmol) of yellow oil, which was dried on high vacuum over night. The crude mixture was used without further purification.

Intermediate 3c: [4-(5-trifluoromethyl-[1,2,4]oxadiazol-3-yl)-phenyl]-acetic acid methyl ester

[4-(N-hydroxycarbamimidoyl)-phenyl]-acetic acid methyl ester (1.2 g, 5.76 mmol) was dissolved in THF (24.01 mL) and cooled to 0° C. Trifluoroacetic anhydride (0.977 mL, 6.92 mmol) was added in one go and the mixture was stirred at 0° C. for 30 min, then cooling was removed and stirring continued for 21.5 h.

Solvent was removed by rotary evaporation. 1H NMR was in agreement with the proposed structure and 19F NMR showed approximately 15% of residual TFA. The crude mixture was used without further purification.

Intermediate 3d: [4-(5-trifluoromethyl-[1,2,4]oxadiazol-3-yl)-phenyl]-acetic acid

[4-(5-Trifluoromethyl-[1,2,4]oxadiazol-3-yl)-phenyl]-acetic acid methyl ester (1.333 g, 4.66 mmol) was dissolved in THF (8.28 mL) and 4 M HCl (12.42 mL) added. The mixture was stirred at RT for 24 h. The reaction mixture was then stirred for 29 h at 60° C. The solvent was removed by rotary evaporation. To ensure complete removal of the HCl, the product was dissolved in Toluene and evaporated again 3 times. The substance was then dissolved in water:acetonitrile 1:1 and lyophilised over the weekend. For analytical purposes, a small sample was subjected to purification by reverse phase prep-HPLC (gradient elution, water/ACN both containing 0.1% TFA). Fractions containing the desired compound were combined and freeze-dried to yield the product as white salt.

$Rt_{MS1}$=2.07 min, ESIMS [M+H]$^+$=273.

1H NMR (400 MHz, DMSO-d$_6$) δ ppm: 12.48 (br. s., 1 H), 8.02 (d, J=8.07 Hz, 2 H), 7.52 (d, J=8.07 Hz, 2 H), 3.72 (s, 2 H).

Example 3

N-methyl-2-[4-(5-trifluoromethyl-[1,2,4]oxadiazol-3-yl)-phenyl]-acetamide

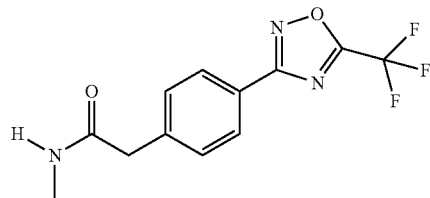 [SMILES: CNC(=O)Cc1ccc(-c2noc(C(F)(F)F)n2)cc1]

$Rt_{MS1}$=3.63 min, ESIMS [M+H]$^+$=286, white powder.

1H NMR (400 MHz, DMSO-d$_6$) δ ppm: 7.92-8.15 (m, 3 H), 7.50 (d, J=8.31 Hz, 2 H), 3.52 (s, 2H), 2.60 (d, J=4.65 Hz, 3 H).

Example 4

N,N-Dimethyl-2-[4-(5-trifluoromethyl-[1,2,4]oxadiazol-3-yl)-phenyl]-acetamide

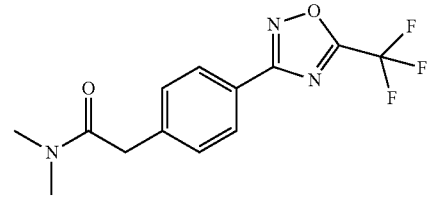 [SMILES: CN(C)C(=O)Cc1ccc(-c2noc(C(F)(F)F)n2)cc1]

$Rt_{MS1}$=3.99 min, ESIMS [M+H]$^+$=300, white powder.

1H NMR (400 MHz, DMSO-d$_6$) δ ppm: 8.00-8.02 (m, J=8.07 Hz, 2 H), 7.46 (d, J=8.07 Hz, 2 H), 3.82 (s, 2 H), 3.04 (s, 3 H), 2.85 (s, 3 H).

Example 5

N-Isopropyl-2-[4-(5-trifluoromethyl-[1,2,4]oxadiazol-3-yl)-phenyl]-acetamide

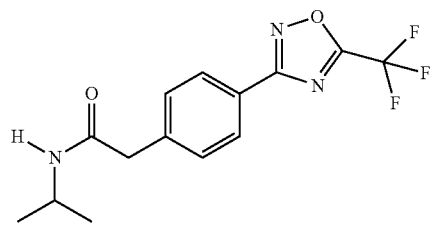 [SMILES: CC(C)NC(=O)Cc1ccc(-c2noc(C(F)(F)F)n2)cc1]

$Rt_{MS1}$=4.24 min, ESIMS [M+H]$^+$=314, white powder.

1H NMR (400 MHz, DMSO-d$_6$) δ ppm: 7.94-8.09 (m, 3 H), 7.49 (d, J=8.07 Hz, 2 H), 3.81 (m, 1H), 3.49 (s, 2 H) 1.06 (d, J=6.60 Hz, 6 H).

Example 6

N-butyl-2-(4-(5-(trifluoromethyl)-1,2,4-oxadiazol-3-yl)phenyl)acetamide

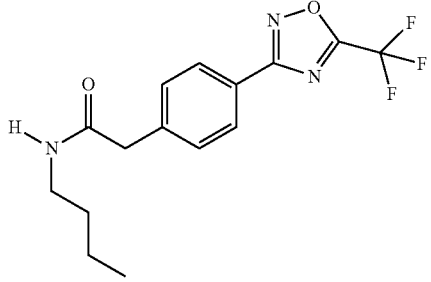 [SMILES: CCCCNC(=O)Cc1ccc(-c2noc(C(F)(F)F)n2)cc1]

$Rt_{MS1}$=4.61 min, ESIMS [M+H]$^+$=328, white powder.
1H NMR (400 MHz, DMSO-d$_6$) δ ppm: 8.10 (t, J=5.01 Hz, 1 H), 8.01 (d, J=8.31 Hz, 2 H), 7.50 (d, J=8.07 Hz, 2 H), 3.52 (s, 2 H), 3.00-3.14 (m, 2 H), 1.33-1.49 (m, 2 H), 1.14-1.33 (m, 2 H), 0.86 (t, J=7.21 Hz, 3 H).

Example 7

N-(2-methoxyethyl)-2-(4-(5-(trifluoromethyl)-1,2,4-oxadiazol-3-yl)phenyl)acetamide

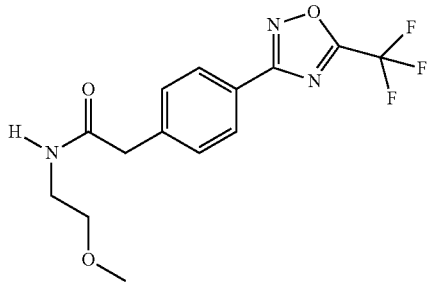 [SMILES: COCCNC(=O)Cc1ccc(-c2noc(C(F)(F)F)n2)cc1]

$Rt_{MS1}$=3.81 min, ESIMS [M+H]$^+$=330, white powder.
1 H NMR (400 MHz, DMSO-d$_6$) δ ppm: 8.24 (br. s., 1 H), 8.00 (d, J=8.07 Hz, 2 H), 7.50 (d, J=8.07 Hz, 2 H), 3.55 (s, 2 H), 3.35 (t, J=5.62 Hz, 2 H), 3.19-3.27 (m, 5 H).

Example 8

Ethyl 2-(2-(4-(5-(trifluoromethyl)-1,2,4-oxadiazol-3-yl)phenyl)acetamido)acetate

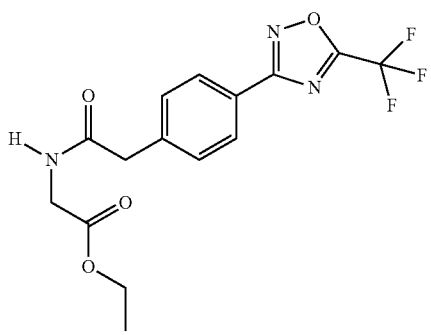 [SMILES: CCOC(=O)CNC(=O)Cc1ccc(-c2noc(C(F)(F)F)n2)cc1]

$Rt_{MS1}$=4.12 min, ESIMS [M+H]$^+$=358, white powder.
1 H NMR (400 MHz, DMSO-d$_6$) δ ppm: 8.60 (t, J=5.75 Hz, 1 H), 8.01 (d, J=8.07 Hz, 2 H), 7.52 (d, J=8.31 Hz, 2 H), 4.09 (q, J=7.09 Hz, 2 H), 3.86 (d, J=5.87 Hz, 2 H), 3.62 (s, 2 H), 1.17 (t, J=7.09 Hz, 3 H).

Example 9

1-Morpholino-2-(4-(5-(trifluoromethyl)-1,2,4-oxadiazol-3-yl)phenyl)ethanone

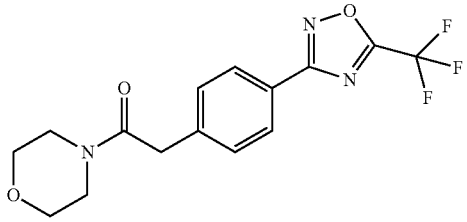 [SMILES: O=C(Cc1ccc(-c2noc(C(F)(F)F)n2)cc1)N1CCOCC1]

$Rt_{MS1}$=3.94 min, ESIMS [M+H]$^+$=342, white powder.
1 H NMR (400 MHz, DMSO-d$_6$) δ ppm: 8.02 (d, J=8.07 Hz, 2 H), 7.47 (d, J=8.07 Hz, 2 H), 3.86 (s, 2 H), 3.40-3.61 (m, 8 H).

Example 10

1-(4-methylpiperazin-1-yl)-2-(4-(5-(trifluoromethyl)-1,2,4-oxadiazol-3-yl)phenyl)ethanone

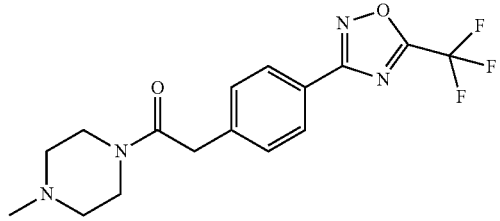 [SMILES: CN1CCN(C(=O)Cc2ccc(-c3noc(C(F)(F)F)n3)cc2)CC1]

$Rt_{MS1}$=2.92 min, ESIMS [M+H]$^+$=355, white powder.
1 H NMR (400 MHz, DMSO-d$_6$) δ ppm: 8.01 (d, J=8.31 Hz, 2 H), 7.47 (d, J=8.31 Hz, 2 H), 3.85 (s, 2 H), 3.50 (m, 4 H), 2.17-2.25 (m, 7 H).

Example 11

N-methoxy-N-methyl-2-(4-(5-(trifluoromethyl)-1,2,4-oxadiazol-3-yl)phenyl)acetamide

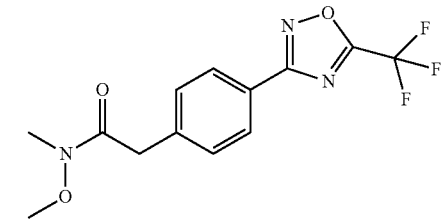 [SMILES: CON(C)C(=O)Cc1ccc(-c2noc(C(F)(F)F)n2)cc1]

$Rt_{MS1}$=4.33 min, ESIMS [M+H]$^+$=316, white powder.
1H NMR (400 MHz, DMSO-d$_6$) δ ppm: 8.01 (d, J=8.07 Hz, 2 H), 7.49 (d, J=8.07 Hz, 2 H), 3.87 (s, 2 H), 3.34 (s, 2 H), 3.13 (s, 3 H).

Examples 12 to 69 and 76-80

General method used for HATU coupling

To 4-(5-trifluoromethyl-[1,2,4]oxadiazol-3-yl)-benzoic acid (40 mg, 0.155 mmol) in DMF (500 μL) were added HATU (70.7 mg, 0.186 mmol) and NMM (34.1 μL, 0.310 mmol). The reaction was stirred for 30 min, the appropriate amine (0.186 mmol) added and then stirred for another hour. The reaction mixture was subjected to purification by reverse phase prep-HPLC (gradient elution, water/ACN both containing 0.1% TFA). Fractions containing the desired compound were combined and freeze-dried. The resulting material was dissolved in a mix of ACN/MeOH. They were loaded on a PL-HCO3 MP cartridge (from StratoSpheres™ SPE) and eluted with ACN (3 ml). The eluate was diluted with water (10 ml) and freeze-dried to yield the final compound.

Preparation of 4-(5-trifluoromethyl-[1,2,4]oxadiazol-3-yl)-benzoic acid

Intermediate 12a: 4-(N-hydroxycarbamimidoyl)-benzoic acid

To 4-cyanobenzoic acid (5 g, 34.0 mmol) in EtOH (150 mL) were added NH2OH.HCl (4.96 g, 71.4 mmol) in water (15 mL) and K2CO3 (7.51 g, 54.4 mmol) in water (30 mL) then 8-hydroxyquinoline (0.064 g, 0.442 mmol). The reaction was stirred at reflux temperature for 4 h. The solvent was removed in vacuo. Water (150 mL) was added and the pH adjusted to 3 using 2M HCl. The white precipitate was filtered off and washed with water to yield E-50734-EXPO37 (3.37 g, 18.71 mmol, 55.0% yield) as a white solid. The mother liquor was extracted with ethyl acetate (75 mL) twice. The combined organics were dried, filtered and condensed in vacuo to obtain: 571 mg (2.54 mmol, 8.0%, 80% purity) as green solid.

$Rt_{MS2}$=2.08 min, ESIMS [M+H]$^+$=181, white salt
1H NMR (400 MHz, DMSO-d6) δ ppm: 12.98 (br. s., 1 H), 9.86 (s, 1 H), 7.93 (d, J=8.31 Hz, 2 H), 7.79 (d, J=8.31 Hz, 2 H), 5.91 (s, 2 H).

Intermediate 12b: 4-(5-trifluoromethyl-[1,2,4]oxadiazol-3-yl)-benzoic acid

To 4-(N-hydroxycarbamimidoyl)-benzoic acid (3.37 g, 18.71 mmol) in dry THF (62.4 mL) was added dropwise (over 30 min) TFAA (3.96 mL, 28.1 mmol). The white insoluble starting material solubilised during addition. The light yellow solution was stirred at RT under inert atmosphere for 2 h. The reaction mixture was condensed in vacuo after 2 h. The crude was washed with EtOAc (100 ml) to afford E-50734-EXPO42 (3.72 g, 14.41 mmol, 77% yield) as a white solid.

$Rt_{MS1}$=2.11. ESIMS [M+H]$^+$ no ionisation.
1H NMR (400 MHz, DMSO-d$_6$): ppm: 8.14-8.23 (m, 4 H) 13.39 (br. s., 1 H). $^{19}$F NMR (377 MHz, DMSO-d$_6$): −64.69 (s, 3F).

Example 12

N-ethyl-4-(5-(trifluoromethyl)-1,2,4-oxadiazol-3-yl)benzamide

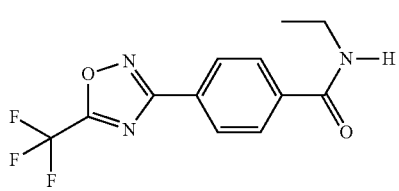 [SMILES: CCNC(=O)c1ccc(-c2noc(C(F)(F)F)n2)cc1]

$Rt_{MS1}$=2.08 min, ESIMS [M+H]$^+$=286, white powder
1H NMR (400 MHz, DMSO-d$_6$) δ ppm: 8.71 (t, J=5.38 Hz, 1 H), 8.16 (d, J=8.80 Hz, 2 H), 8.06 (d, J=8.56 Hz, 2 H), 3.32 (m, 2 H), 1.15 (t, J=7.21 Hz, 3 H).

Example 13

N-(2-hydroxyethyl)-4-(5-(trifluoromethyl)-1,2,4-oxadiazol-3-yl)benzamide

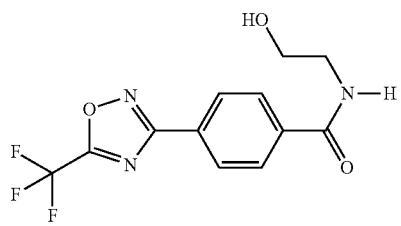 [SMILES: O=C(NCCO)c1ccc(-c2noc(C(F)(F)F)n2)cc1]

$Rt_{MS1}$=1.65 min, ESIMS [M+H]$^+$=302, white powder
1H NMR (400 MHz, DMSO-d$_6$) δ ppm: 8.69 (t, J=5.14 Hz, 1 H), 8.16 (d, J=8.56 Hz, 2 H), 8.08 (d, J=8.56 Hz, 2 H), 4.76 (t, J=5.62 Hz, 1 H), 3.35 (m, 2 H), 3.53 (m, 2 H).

Example 14

N-ethyl-N-methyl-4-(5-(trifluoromethyl)-1,2,4-oxadiazol-3-yl)benzamide

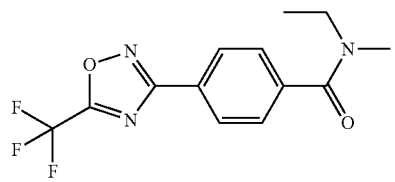 [SMILES: CCN(C)C(=O)c1ccc(-c2noc(C(F)(F)F)n2)cc1]

$Rt_{MS1}$=2.18 min, ESIMS [M+H]$^+$=300, white powder
1H NMR (400 MHz, DMSO-d$_6$) δ ppm: 8.12 (d, J=8.56 Hz, 2 H), 7.62 (m, 2 H, rota), 3.18-3.49 (2q, J=6.80 Hz, 2 H, rota), 2.89+3.31 (2s, 3 H, rota), 1.14+1.07 (2t, J=6.80 Hz, 3 H, rota).

Example 15

N-(2-hydroxyethyl)-N-methyl-4-(5-(trifluoromethyl)-1,2,4-oxadiazol-3-yl)benzamide

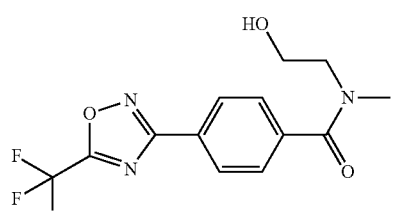

$Rt_{MS1}$=1.67 min, ESIMS [M+H]$^+$=316, colorless resin
1H NMR (400 MHz, DMSO-d$_6$) δ ppm: 8.03-8.19 (m, 2 H, rota), 7.59-7.69 (m, 2 H, rota), 4.84 (t, J=5.62 Hz, 1 H), 3.54+3.66 (2q, J=5.62 Hz, 2 H, rota), 3.24-3.51 (m, 2 H), 2.91+3.06 (2s, 3 H, rota).

Example 16

N-(2-methoxyethyl)-4-(5-(trifluoromethyl)-1,2,4-oxadiazol-3-yl)benzamide

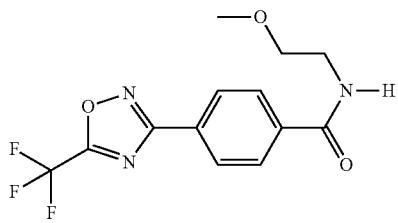 [SMILES: COCCNC(=O)c1ccc(-c2noc(C(F)(F)F)n2)cc1]

Rt$_{MS1}$=1.98 min, ESIMS [M+H]$^+$=316, white powder
1H NMR (400 MHz, DMSO-d$_6$) δ ppm: 8.78 (m, 1 H), 8.17 (d, J=8.56 Hz, 2 H), 8.07 (d, J=8.80 Hz, 2 H), 3.43-3.50 (m, 4 H), 3.28 (s, 3 H).

Example 17

N-(3-hydroxyypropyl)-4-(5-(trifluoromethyl)-1,2,4-oxadiazol-3-yl)benzamide

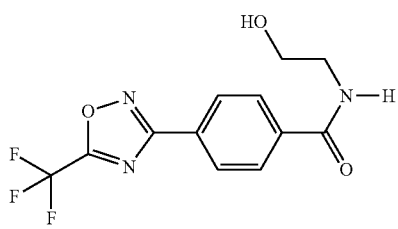 [SMILES: O=C(NCCO)c1ccc(-c2noc(C(F)(F)F)n2)cc1]

Rt$_{MS1}$=1.73 min, ESIMS [M+H]$^+$=316, white powder
1H NMR (400 MHz, DMSO-d$_6$) δ ppm: 8.69 (t, J=5.38 Hz, 1 H), 8.16 (d, J=8.31 Hz, 2 H), 8.06 (d, J=8.31 Hz, 2 H), 4.50 (t, J=5.01 Hz, 1 H), 3.48 (m, 2 H), 3.30-3.38 (m, 2 H), 1.70 (m, 2 H).

Example 18

N-(2-methoxyethyl)-N-methyl-4-(5-(trifluoromethyl)-1,2,4-oxadiazol-3-yl)benzamide

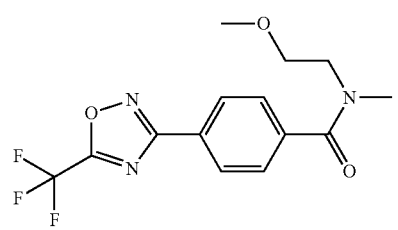 [SMILES: COCCN(C)C(=O)c1ccc(-c2noc(C(F)(F)F)n2)cc1]

Rt$_{MS1}$=2.08 min, ESIMS [M+H]$^+$=330, white powder
1H NMR (400 MHz, DMSO-d$_6$) δ ppm: 8.12 (m, 2 H, rota), 7.62 (m, 2 H, rota), 3.58-3.64 (m, 2 H, rota), 3.35-3.45 (m, 2 H, rota), 3.12+3.33 (2s, 3 H, rota), 2.92+3.05 (2s, 3 H, rota).

Example 19

N-cyclopropyl-4-(5-(trifluoromethyl)-1,2,4-oxadiazol-3-yl)benzamide

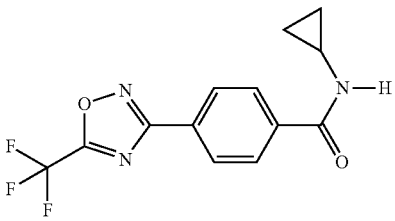 [SMILES: O=C(NC1CC1)c1ccc(-c2noc(C(F)(F)F)n2)cc1]

Rt$_{MS1}$=2.08 min, ESIMS [M+H]$^+$=298, white powder
1H NMR (400 MHz, DMSO-d$_6$) δ ppm 8.68 (d, J=4.40 Hz, 1 H), 8.15 (d, J=8.80 Hz, 2 H), 8.04 (d, J=8.56 Hz, 2 H), 2.88 (m, 1 H), 0.67-0.80 (m, 2 H) 0.54-0.63 (m, 2 H).

Example 20

N-isopropyl-4-(5-(trifluoromethyl)-1,2,4-oxadiazol-3-yl)benzamide

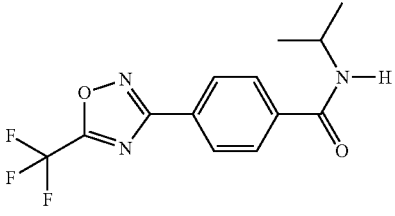 [SMILES: CC(C)NC(=O)c1ccc(-c2noc(C(F)(F)F)n2)cc1]

Rt$_{MS1}$=2.26 min, ESIMS [M+H]$^+$=300, white powder
1H NMR (400 MHz, DMSO-d$_6$) δ ppm 8.48 (d, J=8.31 Hz, 1 H), 8.16 (d, J=8.56 Hz, 2 H), 8.06 (d, J=8.56 Hz, 2 H), 4.07-4.17 (m, 1 H), 1.20 (s, 3 H), 1.13 (s, 3 H).

Example 21

N-(3-methoxyypropyl)-4-(5-(trifluoromethyl)-1,2,4-oxadiazol-3-yl)benzamide

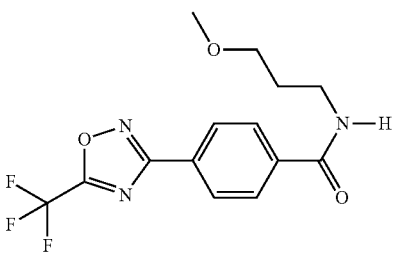 [SMILES: COCCCNC(=O)c1ccc(-c2noc(C(F)(F)F)n2)cc1]

Rt$_{MS1}$=2.06 min, ESIMS [M+H]$^+$=330, white powder
1H NMR (400 MHz, DMSO-d$_6$) δ ppm: 8.71 (t, J=5.50 Hz, 1 H) 8.16 (d, J=8.80 Hz, 2 H), 8.06 (d, J=8.80 Hz, 2 H), 3.39 (t, J=6.36 Hz, 2 H), 3.29-3.36 (m, 2 H), 3.25 (s, 3 H), 1.74-1.82 (quin, J=6.40 Hz, 2 H).

Example 22

N-(2-fluoroethyl)-4-(5-(trifluoromethyl)-1,2,4-oxadiazol-3-yl)benzamide

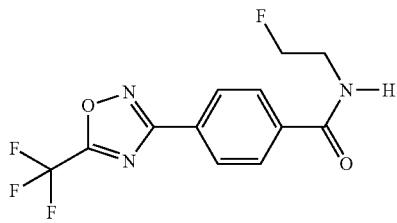 [SMILES: O=C(NCCF)c1ccc(-c2noc(C(F)(F)F)n2)cc1]

Rt$_{MS1}$=2.04 min, ESIMS [M+H]$^+$=303, white powder
1H NMR (400 MHz, DMSO-d$_6$) δ ppm: 8.96 (t, J=5.99 Hz, 1 H), 8.18 (d, J=8.56 Hz, 2 H), 8.09 (d, J=8.80 Hz, 2 H), 4.64-4.61 (m, 1 H), 4.52-4.50 (m, 1 H), 3.65-3.55 (m, 2 H).

Example 23

Pyrrolidin-1-yl(4-(5-(trifluoromethyl)-1,2,4-oxadiazol-3-yl)phenyl)methanone

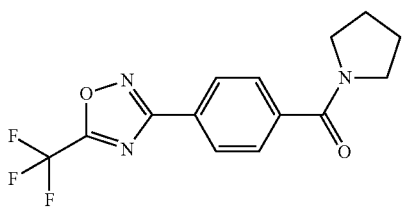 [SMILES: O=C(c1ccc(-c2noc(C(F)(F)F)n2)cc1)N1CCCC1]

Rt$_{MS1}$=2.18 min, ESIMS [M+H]$^+$=312, white powder
1H NMR (400 MHz, DMSO-d$_6$) δ ppm: 8.12 (d, J=8.56 Hz, 2 H), 7.75 (d, J=8.56 Hz, 2 H), 3.50 (t, J=6.72 Hz, 2 H), 3.39 (t, J=6.48 Hz, 2 H), 1.79-1.93 (m, 4 H).

Example 24

N-isopropyl-N-methyl-4-(5-(trifluoromethyl)-1,2,4-oxadiazol-3-yl)benzamide

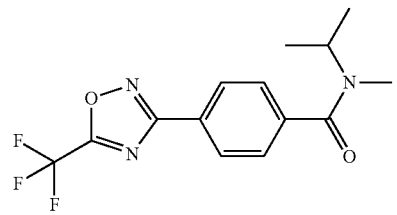 [SMILES: CC(C)N(C)C(=O)c1ccc(-c2noc(C(F)(F)F)n2)cc1]

Rt$_{MS1}$=2.34 min, ESIMS [M+H]$^+$=314, white powder
1H NMR (400 MHz, DMSO-d$_6$) δ ppm: 8.12 (d, J=8.07 Hz, 2 H), 7.60 (m, 2 H), 3.76-4.74 (m, 1 H, rota), 2.69-2.89 (2s, 3 H, rota), 1.11-1.18 (m, 6 H).

Example 25

N-cyclobutyl-4-(5-(trifluoromethyl)-1,2,4-oxadiazol-3-yl)benzamide

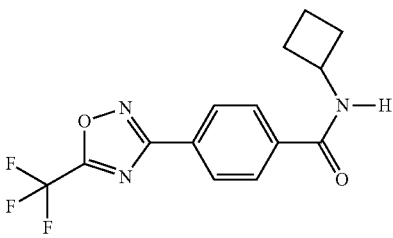 [SMILES: O=C(NC1CCC1)c1ccc(-c2noc(C(F)(F)F)n2)cc1]

Rt$_{MS1}$=2.36 min, ESIMS [M+H]$^+$=312, white powder
1H NMR (400 MHz, DMSO-d$_6$) δ ppm 8.86 (d, J=7.34 Hz, 1 H), 8.16 (d, J=8.31 Hz, 2 H), 8.07 (d, J=8.07 Hz, 2 H), 4.45 (m, 1 H), 2.21-2.24 (m, 2 H) 2.07-2.13 (m, 2 H), 1.66-1.74 (m, 2H).

Example 26

N-(cyclopropylmethyl)-4-(5-(trifluoromethyl)-1,2,4-oxadiazol-3-yl)benzamide

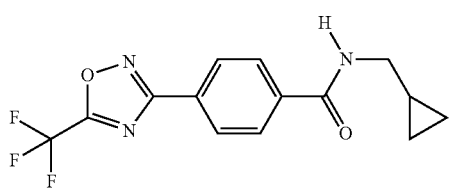 [SMILES: O=C(NCC1CC1)c1ccc(-c2noc(C(F)(F)F)n2)cc1]

Rt$_{MS1}$=2.32 min, ESIMS [M+H]$^+$=312, white powder
1H NMR (400 MHz, DMSO-d$_6$) δ ppm: 8.82 (t, J=5.50 Hz, 1 H), 8.17 (d, J=8.80 Hz, 2 H), 8.08 (d, J=8.56 Hz, 2 H), 3.17 (m, 2 H), 1.00-1.11 (m, 1 H), 0.40-0.48 (m, 2 H), 0.21-0.28 (m, 2H).

Example 27

N-isobutyl-4-(5-(trifluoromethyl)-1,2,4-oxadiazol-3-yl)benzamide

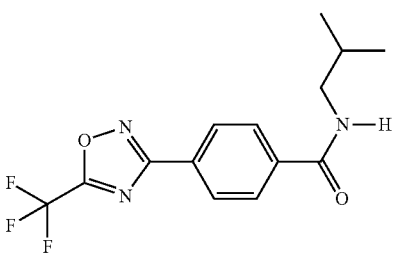 [SMILES: CC(C)CNC(=O)c1ccc(-c2noc(C(F)(F)F)n2)cc1]

Rt$_{MS1}$=2.44 min, ESIMS [M+H]$^+$=314, white powder
1H NMR (400 MHz, DMSO-d$_6$) δ ppm: 8.71 (t, J=5.62 Hz, 1 H), 8.16 (d, J=8.56 Hz, 2 H), 8.06 (d, J=8.56 Hz, 2 H), 3.11 (m, 2 H), 1.87 (m, 1 H), 0.92 (s, 3 H), 0.90 (s, 3 H).

Example 28

(R)—N-(1-hydroxyypropan-2-yl)-4-(5-(trifluoromethyl)-1,2,4-oxadiazol-3-yl)benzamide

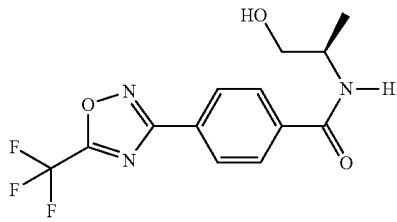 [SMILES: C[C@H](CO)NC(=O)c1ccc(-c2noc(C(F)(F)F)n2)cc1]

Rt$_{MS1}$=1.77 min, ESIMS [M+H]$^+$=316, white powder
1H NMR (400 MHz, DMSO-d$_6$) δ ppm: 8.36 (d, J=8.07 Hz, 1 H), 8.16 (d, J=8.56 Hz, 2 H), 8.08 (d, J=8.80 Hz, 2 H), 4.76 (t, J=5.75 Hz, 1 H), 4.00-4.10 (m, 1 H), 3.44-3.52 (m, 1 H), 3.34-3.41 (m, 1 H), 1.15 (d, J=6.85 Hz, 3 H).

Example 29

N-cyclopentyl-4-(5-(trifluoromethyl)-1,2,4-oxadiazol-3-yl)benzamide

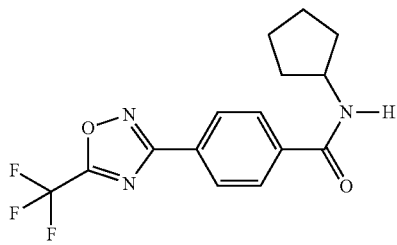 [SMILES: O=C(NC1CCCC1)c1ccc(-c2noc(C(F)(F)F)n2)cc1]

Rt$_{MS1}$=2.48 min, ESIMS [M+H]$^+$=326, white powder
1H NMR (400 MHz, DMSO-d$_6$) δ ppm: 8.54 (d, J=7.34 Hz, 1 H), 8.15 (d, J=8.56 Hz, 2 H), 8.06 (d, J=8.56 Hz, 2 H), 4.18-4.31 (m, 1 H), 1.84-1.98 (m, 2 H), 1.65-1.79 (m, 2 H), 1.47-1.62 (m, 4 H).

Example 30

N-(pentan-3-yl)-4-(5-(trifluoromethyl)-1,2,4-oxadiazol-3-yl)benzamide

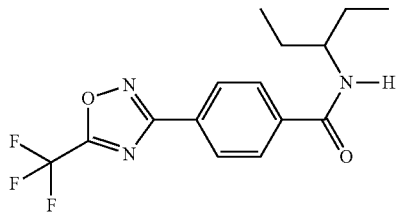 [SMILES: CCC(CC)NC(=O)c1ccc(-c2noc(C(F)(F)F)n2)cc1]

Rt$_{MS1}$=2.56 min, ESIMS [M+H]$^+$=328, white powder
1H NMR (400 MHz, DMSO-d$_6$) δ ppm: 8.29 (d, J=8.31 Hz, 1 H), 8.16 (d, J=8.31 Hz, 2 H), 8.07 (d, J=8.07 Hz, 2 H), 3.76-3.82 (m, 1 H), 1.41-1.61 (m, 4 H), 0.87 (t, J=7.34 Hz, 6 H).

Example 31

N-(2-(dimethylamino)ethyl)-4-(5-(trifluoromethyl)-1,2,4-oxadiazol-3-yl)benzamide

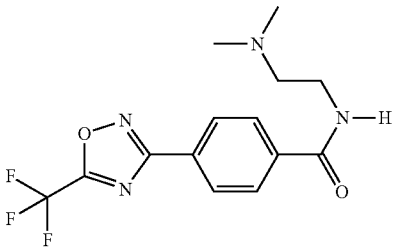 [SMILES: CN(C)CCNC(=O)c1ccc(-c2noc(C(F)(F)F)n2)cc1]

Rt$_{MS1}$=1.37 min, ESIMS [M+H]$^+$=329, white powder
1H NMR (400 MHz, DMSO-d$_6$) δ ppm: 8.64 (t, J=5.62 Hz, 1 H), 8.17 (d, J=8.56 Hz, 2 H), 8.06 (d, J=8.80 Hz, 2 H), 3.35-3.41 (m, 2 H), 2.42 (t, J=6.85 Hz, 2 H), 2.18 (s, 6 H).

To a suspension of Intermediate 12b (1 g, 3.87 mmol) in DCM (20 ml) was added COMU (1.891 g, 4.26 mmol) and DIPEA (0.812 ml, 4.65 mmol). The yellow solution was stirred for 2 min at rt and turned red. 2-Dimethylaminoethylamine (0.518 ml, 4.65 mmol) was added and the reaction mixture was stirred at reflux for 1 hr. After cooling to rt, the mixture was washed with water, saturated aqueous NH$_4$Cl and extrated with EtOAc. The organic layer was dried over Na$_2$SO$_4$ and the solvent was removed in vacuo. The crude product was purified by flash chromatography (ISCO CombiFlash Rf, 120 g silicagel; A=dichloromethane, B=DCM:7N NH$_3$ in MeOH (9:1), 2% hold for 5 min, gradient to 50% B over 15 min). Fractions containing the product where combined to yield 1.355 g. The final product (1.015 g) was obtained after crystallisation from heptane as a white solid.

Example 32

Morpholino(4-(5-(trifluoromethyl)-1,2,4-oxadiazol-3-yl)phenyl)methanone

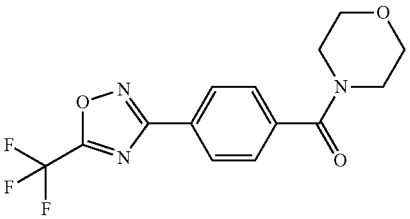 [SMILES: O=C(c1ccc(-c2noc(C(F)(F)F)n2)cc1)N1CCOCC1]

Rt$_{MS1}$=1.95 min, ESIMS [M+H]$^+$=327, white powder
1H NMR (400 MHz, DMSO-d$_6$) δ ppm 8.14 (d, J=8.56 Hz, 2 H), 7.66 (d, J=8.56 Hz, 2 H), 3.50-3.75 (m, 6 H), 3.28-3.43 (m, 2 H).

Example 33

Piperidin-1-yl(4-(5-(trifluoromethyl)-1,2,4-oxadiazol-3-yl)phenyl)methanone

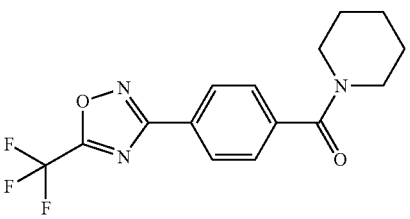 [SMILES: O=C(c1ccc(-c2noc(C(F)(F)F)n2)cc1)N1CCCCC1]

Rt$_{MS1}$=2.44 min, ESIMS [M+H]$^+$=326, white powder
1H NMR (400 MHz, DMSO-d$_6$) δ ppm 8.13 (d, J=8.56 Hz, 2 H), 7.61 (d, J=8.56 Hz, 2 H), 3.2-3.68 (m, 4 H), 1.37-1.69 (m, 6 H).

Example 34

N-cyclohexyl-4-(5-(trifluoromethyl)-1,2,4-oxadiazol-3-yl)benzamide

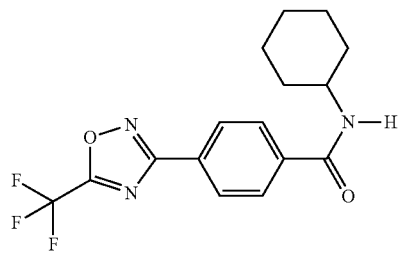 [SMILES: O=C(NC1CCCCC1)c1ccc(-c2noc(C(F)(F)F)n2)cc1]

Rt$_{MS1}$=2.64 min, ESIMS [M+H]$^+$=340, white powder
1H NMR (400 MHz, DMSO-d$_6$) δ ppm: 8.46 (d, J=7.58 Hz, 1 H), 8.15 (d, J=8.80 Hz, 2 H), 8.06 (d, J=8.56 Hz, 2 H), 3.77 (m, 1 H), 1.83-1.59 (m, 5 H), 1.26-1.39 (m, 4 H), 1.14 (m, 1 H).

Example 35

N-phenyl-4-(5-(trifluoromethyl)-1,2,4-oxadiazol-3-yl)benzamide

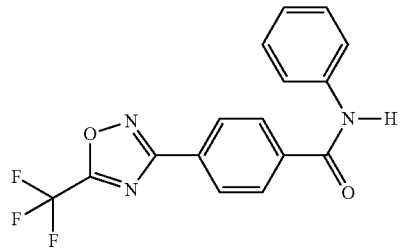 [SMILES: O=C(Nc1ccccc1)c1ccc(-c2noc(C(F)(F)F)n2)cc1]

Rt$_{MS1}$=2.61 min, ESIMS [M+H]$^+$=334, white powder
1H NMR (400 MHz, DMSO-d$_6$) δ ppm: 10.49 (s, 1 H), 8.24 (d, J=8.56 Hz, 2 H), 8.18 (d, J=8.80 Hz, 2 H), 7.80 (d, J=7.58 Hz, 2 H), 7.38 (dd, J=7.58 Hz, 2 H), 7.14 (dd, J=7.58 Hz, 1 H).

Example 36

(4-methylpiperazin-1-yl)(4-(5-(trifluoromethyl)-1,2,4-oxadiazol-3-yl)phenvyl)methanone

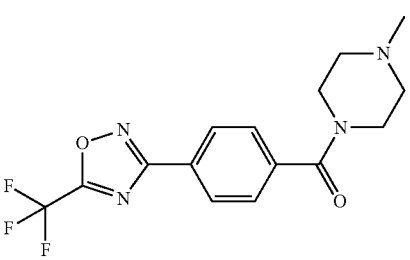 [SMILES: CN1CCN(C(=O)c2ccc(-c3noc(C(F)(F)F)n3)cc2)CC1]

Rt$_{MS1}$=1.29 min, ESIMS [M+H]$^+$=341, white powder
1H NMR (400 MHz, DMSO-d$_6$) δ ppm: 8.13 (d, J=8.56 Hz, 2 H), 7.63 (d, J=8.56 Hz, 2 H), 3.28-3.70 (m, 4 H), 2.24-2.42 (m, 4 H), 2.20 (s, 3 H).

Example 37

N-(2-(dimethylamino)ethyl)-N-methyl-4-(5-(trifluoromethyl)-1,2,4-oxadiazol-3-yl)benzamide

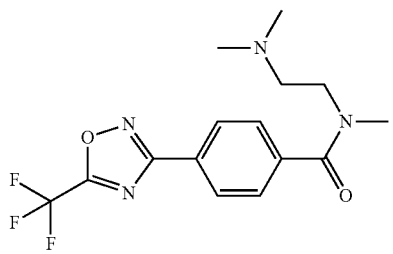 [SMILES: CN(C)CCN(C)C(=O)c1ccc(-c2noc(C(F)(F)F)n2)cc1]

Rt$_{MS1}$=1.37 min, ESIMS [M+H]$^+$=343, white powder
1H NMR (400 MHz, DMSO-d$_6$) δ ppm: 8.13 (d, J=8.07 Hz, 2 H), 7.61 (d, J=8.07 Hz, 2 H), 3.23-3.61 (m, 2 H), 2.88+3.04 (2s, 3 H, rota), 2.30-2.56 (m, 2 H) 1.90+2.28 (2s, 6 H, rota).

Example 38

N-(1-methylpiperidin-4-yl)-4-(5-(trifluoromethyl)-1,2,4-oxadiazol-3-yl)benzamide

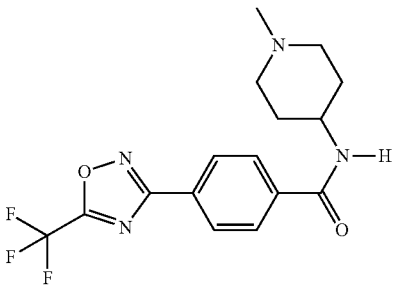 [SMILES: CN1CCC(NC(=O)c2ccc(-c3noc(C(F)(F)F)n3)cc2)CC1]

Rt$_{MS1}$=1.41 min, ESIMS [M+H]$^+$=355, white powder
1H NMR (400 MHz, DMSO-d$_6$) δ ppm 8.51 (d, J=7.58 Hz, 1 H), 8.15 (d, J=8.56 Hz, 2 H), 8.06 (d, J=8.80 Hz, 2 H), 3.69-3.81 (m, 1 H), 2.76-2.79 (m, 2 H), 2.17 (s, 3 H), 1.95 (t, J=11.13 Hz, 2 H), 1.72-1.82 (m, 2 H), 1.51-1.68 (m, 2 H).

Example 39

(4-(dimethylamino)piperidin-1-yl)(4-(5-(trifluoromethyl)-1,2,4-oxadiazol-3-yl)phenyl)methanone

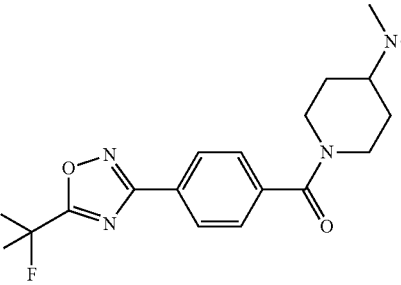

Rt$_{MS1}$=1.37 min, ESIMS [M+H]$^+$=369, white powder
1H NMR (400 MHz, DMSO-d$_6$) δ ppm: 8.13 (d, J=8.56 Hz, 2 H), 7.63 (d, J=8.31 Hz, 2 H), 4.44 (m, 1 H), 3.55 (m, 1 H), 3.05 (m, 1 H), 2.88 (m, 1 H), 2.42 (m, 1 H), 2.18 (s, 6 H), 1.83 (m, 1 H), 1.68 (m, 1 H), 1.37 (m, 2 H).

Example 40

N-(3-(1H-imidazol-1-yl)propyl)-4-(5-(trifluoromethyl)-1,2,4-oxadiazol-3-yl)benzamide

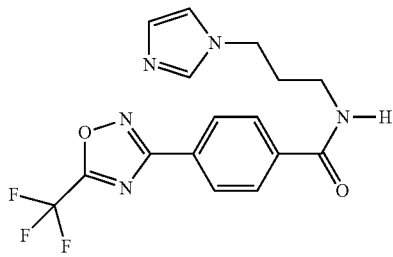 [SMILES: O=C(NCCCn1ccnc1)c1ccc(-c2noc(C(F)(F)F)n2)cc1]

Rt$_{MS1}$=1.43 min, ESIMS [M+H]$^+$=366, white powder
1H NMR (400 MHz, DMSO-d$_6$) δ ppm: 8.76 (t, J=5.87 Hz, 1 H), 8.17 (d, J=8.31 Hz, 2 H), 8.07 (d, J=8.31 Hz, 2 H), 7.68 (s, 1 H), 7.23 (s, 1 H), 6.90 (s, 1 H), 4.04 (t, J=6.85 Hz, 2 H), 3.24-3.29 (m, 2 H), 1.95-2.02 (m, 2 H).

Example 41

N-(4-(dimethylamino)phenyl)-4-(5-(trifluoromethyl)-1,2,4-oxadiazol-3-yl)benzamide

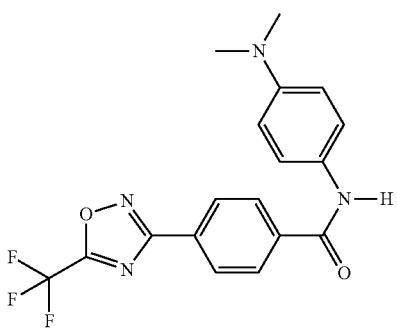 [SMILES: CN(C)c1ccc(NC(=O)c2ccc(-c3noc(C(F)(F)F)n3)cc2)cc1]

Rt$_{MS1}$=1.67 min, ESIMS [M+H]$^+$=377, dark grey powder
1H NMR (400 MHz, DMSO-d$_6$) δ ppm: 10.23 (s, 1 H) 8.21 (d, J=8.56 Hz, 2 H), 8.17 (d, J=8.56 Hz, 2 H), 7.60 (d, J=9.54 Hz, 2 H), 6.75 (d, J=9.05 Hz, 2 H), 2.89 (s, 6 H).

Example 42

(4-phenylpiperazin-1-yl)(4-(5-(trifluoromethyl)-1,2,4-oxadiazol-3-yl)phenyl)methanone

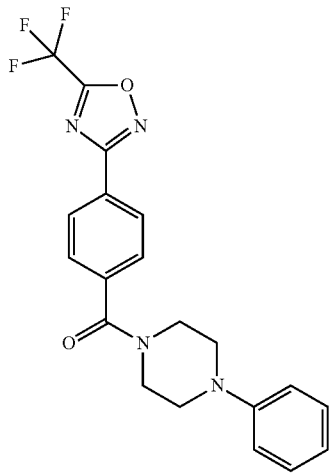 [SMILES: O=C(c1ccc(-c2noc(C(F)(F)F)n2)cc1)N1CCN(c2ccccc2)CC1]

Rt$_{MS1}$=2.44 min, ESIMS [M+H]$^+$=403, white powder
1H NMR (400 MHz, DMSO-d$_6$) δ ppm: 8.16 (d, J=8.31 Hz, 2 H), 7.64-7.75 (m, 2 H), 7.24 (dd, J=8.68, 7.21 Hz, 2 H), 6.97 (d, J=7.82 Hz, 2 H), 6.82 (t, J=7.34 Hz, 1 H), 3.80 (br. s., 2 H) 3.49 (br. s., 2 H), 3.06-3.29 (m, 4 H).

Example 43

(4-benzylpiperidin-1-yl)(4-(5-(trifluoromethyl)-1,2,4-oxadiazol-3-yl)phenyl)methanone

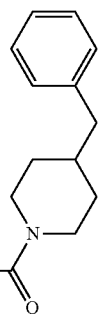

Rt$_{MS1}$=3.03 min, ESIMS [M+H]$^+$=416, white powder
1H NMR (400 MHz, DMSO-d$_6$) δ ppm: 8.12 (d, J=8.56 Hz, 2 H), 7.60 (d, J=8.31 Hz, 2 H), 7.28 (t, J=7.58 Hz, 2 H), 7.17-7.19 (m, 3 H), 4.47 (m, 1 H), 3.51 (m, 1 H), 3.01 (m, 1 H), 2.75 (m, 1H), 2.53-2.55 (m, 2 H), 1.81 (m, 1 H), 1.06-1.74 (m, 4 H).

Example 44

N-(4-(morpholinomethyl)benzyl)-4-(5-(trifluoromethyl)-1,2,4-oxadiazol-3-yl)benzamide

Rt$_{MS1}$=1.59 min, ESIMS [M+H]$^+$=447, white powder
1H NMR (400 MHz, DMSO-d$_6$) δ ppm: 9.27 (t, J=5.87 Hz, 1 H), 8.18 (d, J=8.56 Hz, 2 H), 8.11 (d, J=8.56 Hz, 2 H), 7.28 (m, 4 H), 4.49 (d, J=5.87 Hz, 2 H), 3.53-3.58 (m, 4 H), 3.43 (s, 2 H), 2.33 (m, 4 H).

Example 45

N-phenethyl-4-(5-(trifluoromethyl)-1,2,4-oxadiazol-3-yl)benzamide

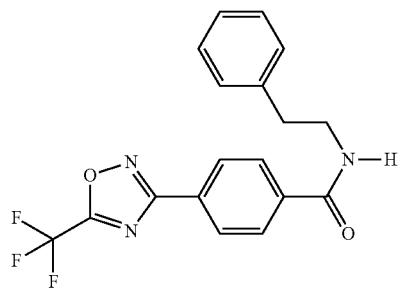 [SMILES: O=C(NCCc1ccccc1)c1ccc(-c2noc(C(F)(F)F)n2)cc1]

$Rt_{MS1}$=2.60 min, ESIMS [M+H]⁺=362, white powder
1H NMR (400 MHz, DMSO-d₆) δ ppm: 8.82 (t, J=5.87 Hz, 1 H), 8.16 (d, J=8.56 Hz, 2 H), 8.04 (d, J=8.56 Hz, 2 H), 7.18-7.34 (m, 5 H), 3.48-3.55 (m, 2 H) 2.87 (t, J=7.46 Hz, 2 H).

Example 46

N-benzyl-4-(5-(trifluoromethyl)-1,2,4-oxadiazol-3-yl)benzamide

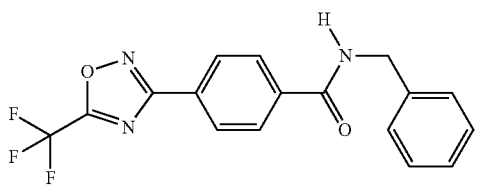 [SMILES: O=C(NCc1ccccc1)c1ccc(-c2noc(C(F)(F)F)n2)cc1]

$Rt_{MS1}$=2.52 min, ESIMS [M+H]⁺=348, white powder
1H NMR (400 MHz, DMSO-d₆) δ ppm: 9.30 (t, J=5.75 Hz, 1 H), 8.18 (d, J=8.80 Hz, 2 H), 8.12 (d, J=8.56 Hz, 2 H), 7.35 (d, J=4.40 Hz, 4 H), 7.25 (m, 1 H), 4.51 (d, J=5.87 Hz, 2 H).

Example 47

N-(ppyridin-4-yl)-4-(5-(trifluoromethyl)-1,2,4-oxadiazol-3-yl)benzamide

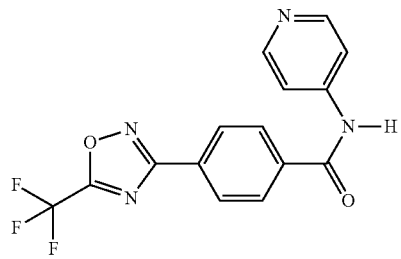 [SMILES: O=C(Nc1ccncc1)c1ccc(-c2noc(C(F)(F)F)n2)cc1]

$Rt_{MS1}$=1.57 min, ESIMS [M+H]⁺=335, white powder
1H NMR (400 MHz, DMSO-d₆) δ ppm: 10.83 (s, 1 H), 8.51 (d, J=6.36 Hz, 2 H), 8.26 (d, J=8.80 Hz, 2 H), 8.19 (d, J=8.80 Hz, 2 H), 7.79-7.82 (d, J=6.36 Hz, 2 H).

Example 48

N-(ppyridin-3-yl)-4-(5-(trifluoromethyl)-1,2,4-oxadiazol-3-yl)benzamide

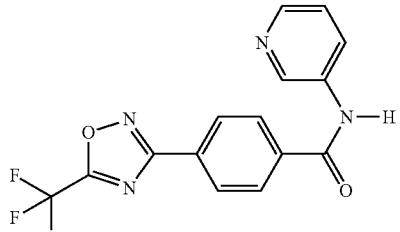

$Rt_{MS1}$=1.53 min, ESIMS [M+H]⁺=335, white powder
1H NMR (400 MHz, DMSO-d₆) δ ppm: 10.70 (s, 1 H), 8.95 (m, 1 H), 8.35 (dd, J=4.65 Hz, 1.47 Hz, 1 H), 8.19-8.27 (m, 5 H), 7.43 (dd, J=8.56, 4.89 Hz, 1 H).

Example 49

N-((1-methylpiperidin-4-yl)methyl)-4-(5-(trifluoromethyl)-1,2,4-oxadiazol-3-yl)benzamide

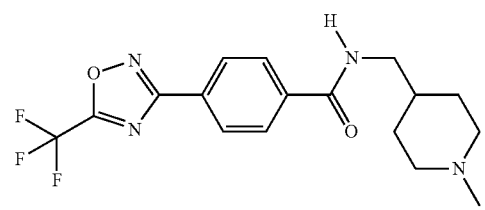 [SMILES: CN1CCC(CNC(=O)c2ccc(-c3noc(C(F)(F)F)n3)cc2)CC1]

$Rt_{MS1}$=1.43 min, ESIMS [M+H]⁺=369, white powder
1H NMR (400 MHz, DMSO-d₆) δ ppm: 8.71 (t, J=5.62 Hz, 1 H), 8.16 (d, J=8.56 Hz, 2 H), 8.06 (d, J=8.56 Hz, 2 H), 3.17 (dd, J=6.36 Hz, 2 H), 2.75 (m, 2 H), 2.14 (s, 3 H), 1.80 (t, 2 H), 1.65 (m, 2 H), 1.47-1.56 (m, 1 H), 1.13-1.24 (m, 2 H).

Example 50

(S)—N-(1-hydroxyypropan-2-yl)-4-(5-(trifluoromethyl)-1,2,4-oxadiazol-3-yl)benzamide

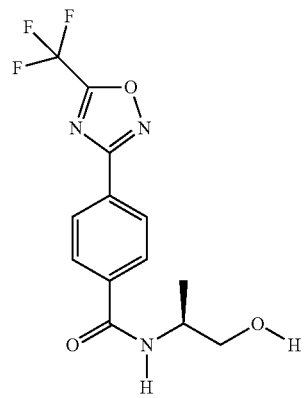 [SMILES: C[C@@H](CO)NC(=O)c1ccc(-c2noc(C(F)(F)F)n2)cc1]

$Rt_{MS1}$=1.77 min, ESIMS [M+H]⁺=316.2, white powder.
hu 1H NMR (400 MHz, DMSO-d₆) δ ppm: 8.36 (d, J=7.83 Hz, 1 H), 8.15-8.17 (m, 2 H), 8.04-8.10 (m, 2 H), 4.76 (t, J=5.75 Hz, 1 H), 4.05 (m, 1 H), 3.34-3.53 (m, 2 H), 1.15 (d, J=6.85 Hz, 3 H).

Example 51

N-(2-(dimethylamino)propyl)-4-(5-(trifluoromethyl)-1,2,4-oxadiazol-3-yl)benzamide

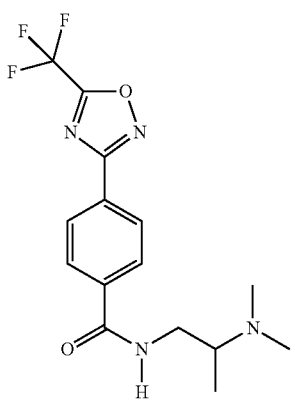 [SMILES: CC(CNC(=O)c1ccc(-c2noc(C(F)(F)F)n2)cc1)N(C)C]

Rt$_{MS1}$=1.41 min, ESIMS [M+H]$^+$=343, white powder.
$^1$H NMR (400 MHz, DMSO-d$_6$) δ ppm: 8.54 (t, J=5.62 Hz, 1 H), 8.13-8.20 (m, 2 H), 8.04-8.06 (m, J=8.60 Hz, 2 H), 3.15-3.41 (m, 2 H), 2.80 (m, 1 H), 2.20 (s, 6 H), 0.92 (d, J=6.60 Hz, 3 H).

Example 52

N-(2-(dimethylamino)-2-oxoethyl)-4-(5-(trifluoromethyl)-1,2,4-oxadiazol-3-yl)benzamide

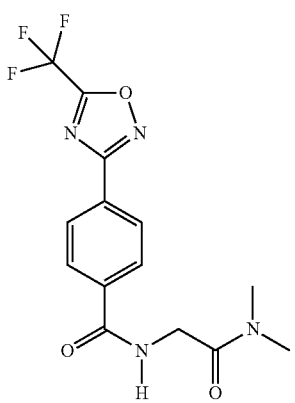 [SMILES: CN(C)C(=O)CNC(=O)c1ccc(-c2noc(C(F)(F)F)n2)cc1]

Rt$_{MS1}$=1.78 min, ESIMS [M+H]$^+$=343, white powder.
$^1$H NMR (400 MHz, DMSO-d$_6$) δ ppm: 8.79 (t, J=5.87 Hz, 1 H), 8.15-8.24 (m, 2 H) 8.07-8.14 (m, 2 H), 4.14 (d, J=5.87 Hz, 2 H), 3.03 (s, 3 H), 2.87 (s, 3 H).

Example 53

N-(1-(dimethylamino)propan-2-yl)-4-(5-(trifluoromethyl)-1,2,4-oxadiazol-3-yl)benzamide

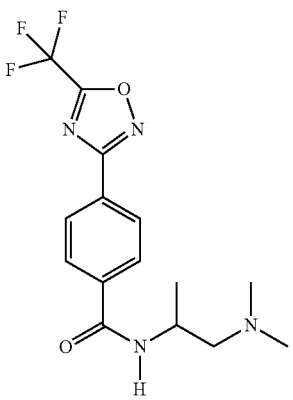 [SMILES: CC(CN(C)C)NC(=O)c1ccc(-c2noc(C(F)(F)F)n2)cc1]

Rt$_{MS1}$=1.43 min, ESIMS [M+H]$^+$=343, white powder.
$^1$H NMR (400 MHz, DMSO-d$_6$) δ ppm: 8.40 (d, J=8.31 Hz, 1 H), 8.14-8.19 (m, 2 H), 8.03-8.10 (m, 2 H), 4.09-4.27 (m, 1 H), 2.18-2.44 (m, 2 H), 2.17 (s, 6 H), 1.15 (d, J=6.60 Hz, 3 H).

Example 54

(3-hydroxypyrrolidin-1-yl)(4-(5-(trifluoromethyl)-1,2,4-oxadiazol-3-yl)phenyl)methanone

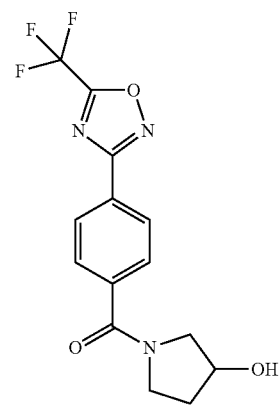 [SMILES: O=C(c1ccc(-c2noc(C(F)(F)F)n2)cc1)N1CCC(O)C1]

Rt$_{MS1}$=1.67 min, ESIMS [M+H]$^+$=328, colorless resin
$^1$H NMR (400 MHz, DMSO-d$_6$) δ ppm: 8.13 (d, J=8.56 Hz, 2 H), 7.75 (dd, J=8.56, 4.40 Hz, 2 H), 4.98+5.06 (2d, J=3.67 Hz, 1 H, rota), 4.18-4.42 (m, 1 H), 3.50-3.67 (m, 2.5H, rota), 3.40 (m, 1 H), 3.19 (m, 0.5H, rota), 1.72-2.04 (m, 2 H).

Example 55

Tert-butyl 4-(4-(5-(trifluoromethyl)-1,2,4-oxadiazol-3-yl)benzoyl)piperazine-1-carboxylate

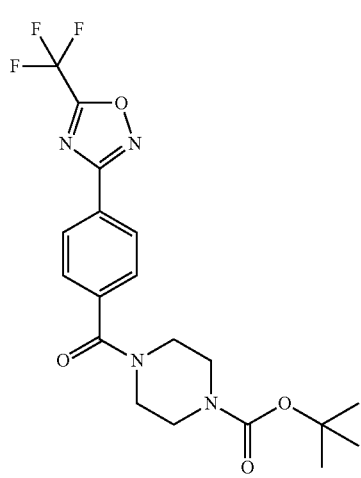 [SMILES: CC(C)(C)OC(=O)N1CCN(C(=O)c2ccc(-c3noc(C(F)(F)F)n3)cc2)CC1]

Rt$_{MS1}$=2.58 min, ESIMS [M+H]$^+$=427.1, white powder.
$^1$H NMR (400 MHz, DMSO-d$_6$) δ ppm: 8.14 (d, J=8.60 Hz, 2 H), 7.66 (, J8.6019 Hz, 2 H), 3.34-3.72 (m, 8 H), 1.41 (s, 9 H).

Example 56

N-(1-tetrahydroxy-2 H-butan-2-yl)-4-(5-(trifluoromethyl)-1,2,4-oxadiazol-3-yl)benzamide

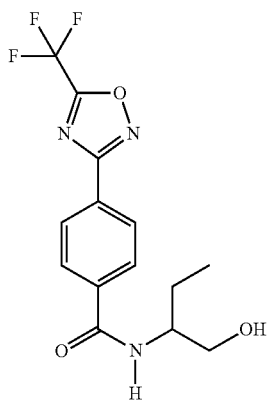 [SMILES: CCC(CO)NC(=O)c1ccc(-c2noc(C(F)(F)F)n2)cc1]

Rt$_{MS1}$=1.19 min, ESIMS [M+H]$^+$=330.3, white powder.
$^1$H NMR (400 MHz, DMSO-d$_6$) bppm: 8.27 (d, J=8.56 Hz, 1 H), 8.13-8.19 (m, 2 H), 8.06-8.11 (m, 2 H), 4.71 (t, J=5.87 Hz, 1 H), 3.90 (m, 1 H), 3.37-3.53 (m, 2 H), 1.40-1.74 (m, 2 H), 0.89 (t, J=7.34 Hz, 3 H).

Example 57

N-(tetrahydro-2H-pyran-4-yl)-4-(5-(trifluoromethyl)-1,2,4-oxadiazol-3-yl)benzamide

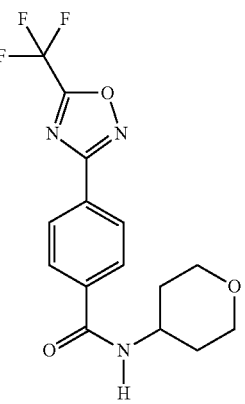

Rt$_{MS1}$=2.02 min, ESIMS [M+H]$^+$=342.3, white powder.
$^1$H NMR (400 MHz, DMSO-d$_6$) δ ppm: 8.57 (d, J=7.58 Hz, 1 H), 8.13-8.21 (m, 2 H), 8.04-8.11 (m, 2 H), 3.96-4.11 (m, 1 H), 3.84-3.94 (m, 2 H), 3.35-3.45 (m, 2 H), 1.73-1.87 (m, 2 H), 1.52-1.69 (m, 2 H).

Example 58

N-(1-hydroxy-4-methylpentan-2-yl)-4-(5-(trifluoromethyl)-1,2,4-oxadiazol-3-yl)benzamide

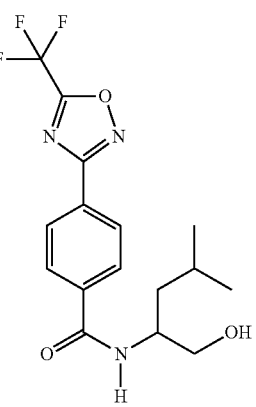

Rt$_{MS1}$=2.26 min, ESIMS [M+H]$^+$=358.3, white powder.
$^1$H NMR (400 MHz, DMSO-d$_6$) δ ppm: 8.26 (d, J=8.56 Hz, 1 H), 8.12-8.19 (m, 2 H), 8.04-8.11 (m, 2 H), 4.71 (t, J=5.75 Hz, 1 H), 4.08 (m, 1 H), 3.35-3.48 (m, 2 H), 1.62 (m, 1 H), 1.34-1.53 (m, 2 H), 0.90 (t, J=6.72 Hz, 6 H).

Example 59

4-[4-(5-trifluoromethyl-[1,2,4]oxadiazol-3-yl)-benzoylamino]-piperidine-1-carboxylic acid tert-butyl ester

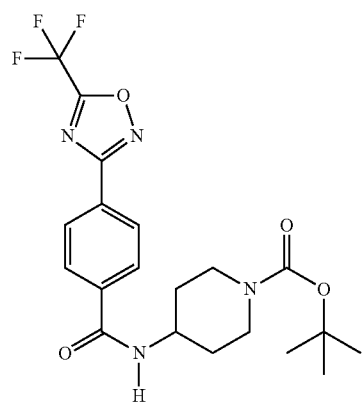 [SMILES: CC(C)(C)OC(=O)N1CCC(NC(=O)c2ccc(-c3noc(C(F)(F)F)n3)cc2)CC1]

Rt$_{MS1}$=2.62 min, ESIMS [M+H]$^+$=441.3, white powder.
$^1$H NMR (400 MHz, DMSO-d$_6$) δ ppm: 8.54 (d, J=7.83 Hz, 1 H), 8.13-8.20 (m, 2 H), 8.02-8.11 (m, 2 H), 3.87-4.10 (m, 3 H), 2.73-2.98 (m, 2 H), 1.75-1.87 (m, 2 H), 1.36-1.50 (m, 11 H).

Example 60 tert-butyl (2-(4-(5-(trifluoromethyl)-1,2,4-oxadiazol-3-yl)benzamido)cyclohexyl)carbamate

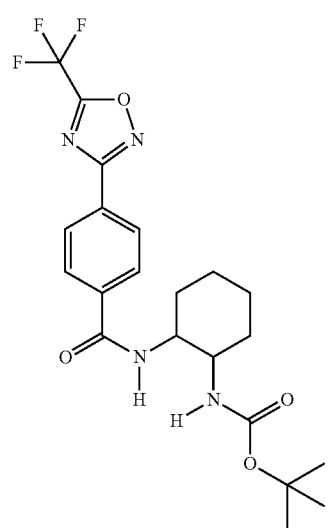 [SMILES: CC(C)(C)OC(=O)NC1CCCCC1NC(=O)c1ccc(-c2noc(C(F)(F)F)n2)cc1]

Rt$_{MS1}$=2.78 min, ESIMS [M+H]$^+$=455.3, white powder.
$^1$H NMR (400 MHz, DMSO-d$_6$) δ ppm: 8.34 (d, J=8.80 Hz, 1 H), 8.10-8.15 (m, 2 H), 7.99-8.06 (m, 2 H), 6.74 (d, J=9.05 Hz, 1 H), 3.71 (m, 1 H), 3.40 (m, 1H), 1.74-1.87 (m, 2 H), 1.64-1.74 (m, 2H), 1.17-1.46 (m, 13H).

Example 61

N-(2-hydroxycyclohexyl)-4-(5-(trifluoromethyl)-1,2,4-oxadiazol-3-yl)benzamide

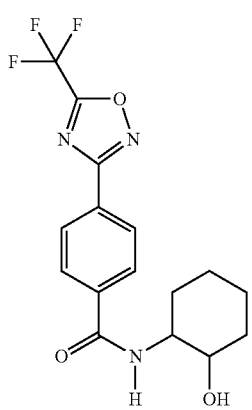 [SMILES: O=C(NC1CCCCC1O)c1ccc(-c2noc(C(F)(F)F)n2)cc1]

Rt$_{MS1}$=2.13 min, ESIMS [M+H]$^+$=356.3, white powder.
$^1$H NMR (400 MHz, DMSO-d$_6$) δ ppm: 8.13-8.20 (m, 2 H), 8.06-8.12 (m, 3 H), 4.70 (d, J=3.67 Hz, 1 H), 3.83-3.92 (m, 2 H), 1.25-1.85 (m, 8 H).

Example 62

Tert-butyl 3-(4-(5-(trifluoromethyl)-1,2,4-oxadiazol-3-yl)benzamido)piperidine-1-carboxylate

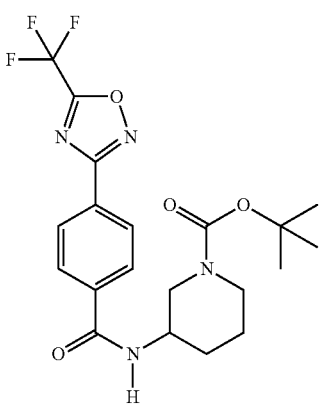 [SMILES: CC(C)(C)OC(=O)N1CCCC(NC(=O)c2ccc(-c3noc(C(F)(F)F)n3)cc2)C1]

Rt$_{MS1}$=2.66 min, ESIMS [M+H]$^+$=441.3, white powder.
$^1$H NMR (400 MHz, DMSO-d$_6$) δ ppm: 8.52 (d, J=7.09 Hz, 1 H), 8.14-8.20 (m, 2 H), 8.03-8.11 (m, 2 H), 3.57-4.12 (m, 3.7H, rota), 2.75-3.08 (m, 1.7H, rota), 1.91 (m, 1 H), 1.73 (m, 1 H), 1.56 (m, 1 H), 1.46 (m, 1 H), 1.38 (br. s., 9 H).

Example 63

N-(2-(methylamino)-2-oxoethyl)-4-(5-(trifluoromethyl)-1,2,4-oxadiazol-3-yl)benzamide

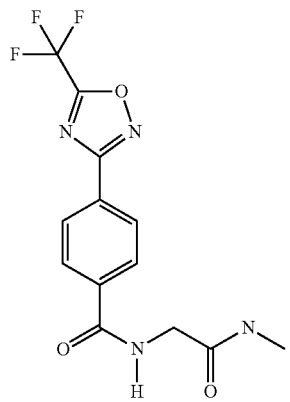 [SMILES: CNC(=O)CNC(=O)c1ccc(-c2noc(C(F)(F)F)n2)cc1]

$Rt_{MS1}$=1.63 min, ESIMS [M+H]$^+$=329.2, white powder.
$^1$H NMR (400 MHz, DMSO-d$_6$) δ ppm: 8.99 (t, J=5.75 Hz, 1 H), 8.19 (d, J=8.31 Hz, 2 H), 8.12 (d, J=8.56 Hz, 2 H), 7.88 (m, 1 H), 3.86 (d, J=6.11 Hz, 2 H), 2.61 (d, J=4.65 Hz, 3 H).

Example 64

N-(1-acetylpiperidin-4-yl)-4-(5-(trifluoromethyl)-1,2,4-oxadiazol-3-yl)benzamide

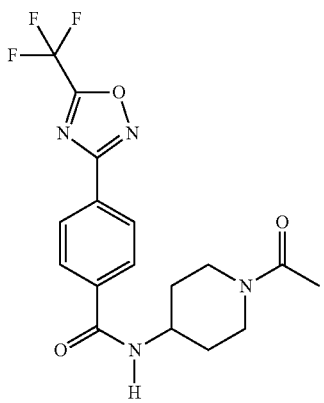 [SMILES: CC(=O)N1CCC(NC(=O)c2ccc(-c3noc(C(F)(F)F)n3)cc2)CC1]

$Rt_{MS1}$=1.86 min, ESIMS [M+H]$^+$=383.2, white powder.
$^1$H NMR (400 MHz, DMSO-d$_6$) δ ppm: 8.55 (d, J=7.82 Hz, 1 H), 8.16-8.18 (m, 2 H) 8.06-8.08 (m, J=8.56 Hz, 2 H), 4.35 (m, 1 H), 4.03 (m, 1 H) 3.82 (m, 1 H), 3.15 (m, 1 H), 2.70 (m, 1 H), 2.02 (s, 3 H), 1.77-1.95 (m, 2 H), 1.32-1.57 (m, 2 H).

Example 65

N-(1,2,2,6,6-pentamethylpiperidin-4-yl)-4-(5-(trifluoromethyl)-1,2,4-oxadiazol-3-yl)benzamide

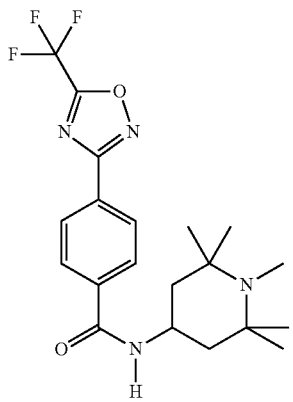 [SMILES: CN1C(C)(C)CC(NC(=O)c2ccc(-c3noc(C(F)(F)F)n3)cc2)CC1(C)C]

$Rt_{MS1}$=1.59 min, ESIMS [M+H]$^+$=411.3, white powder.
$^1$H NMR (400 MHz, DMSO-d$_6$) δ ppm: 8.44 (d, J=7.58 Hz, 1 H), 8.12-8.18 (m, 2 H), 8.03-8.09 (m, 2 H), 4.20 (m, 1 H), 2.19 (s, 3 H), 1.71 (m, 2 H), 1.40-1.50 (m, 2 H), 1.10 (s, 6 H), 1.05 (s, 6H).

Example 66

Tert-butyl 3-(4-(5-(trifluoromethyl)-1,2,4-oxadiazol-3-yl)benzamido)pyrrolidine-1-carboxylate

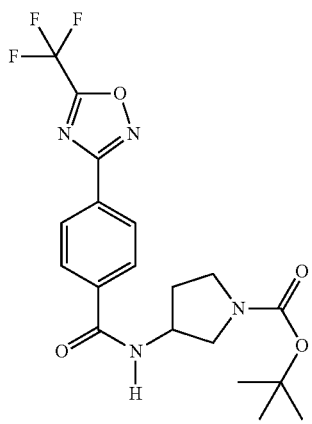 [SMILES: CC(C)(C)OC(=O)N1CCC(NC(=O)c2ccc(-c3noc(C(F)(F)F)n3)cc2)C1]

$Rt_{MS1}$=2.53 min, ESIMS [M+H]$^+$=427.3, white powder.
$^1$H NMR (400 MHz, DMSO-d$_6$) δ ppm: 8.80 (d, J=6.60 Hz, 1 H), 8.14-8.21 (m, 2 H), 8.04-8.11 (m, 2 H), 4.45 (m, 1H), 3.16-3.64 (m, 4 H), 1.85-2.19 (m, 2 H), 1.41 (s, 9 H).

Example 67

N-(2-methoxypyridin-4-yl)-4-(5-(trifluoromethyl)-1,2,4-oxadiazol-3-yl)benzamide

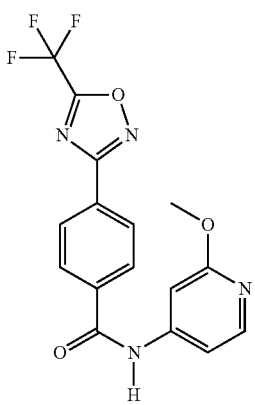 [SMILES: COc1cc(NC(=O)c2ccc(-c3noc(C(F)(F)F)n3)cc2)ccn1]

Rt$_{MS1}$=1.79 min, ESIMS [M+H]$^+$=365.2, white powder.
$^1$H NMR (400 MHz, DMSO-d$_6$) δ ppm: 10.76 (s, 1 H), 8.22-8.27 (m, 2 H), 8.15-8.21 (m, 2 H), 8.11 (d, J=5.87 Hz, 1 H), 7.37 (m, J=5.60 Hz, 1 H), 7.34 (m, J=1.20 Hz, 1 H), 3.86 (s, 3 H).

Example 68

N-(2,6-dimethylpyridin-4-yl)-4-(5-(trifluoromethyl)-1,2,4-oxadiazol-3-yl)benzamide

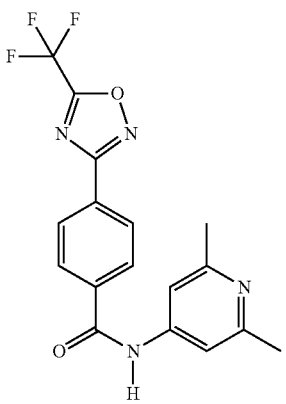 [SMILES: Cc1cc(NC(=O)c2ccc(-c3noc(C(F)(F)F)n3)cc2)cc(C)n1]

Rt$_{MS1}$=1.67 min, ESIMS [M+H]$^+$=363.2, white powder.
$^1$H NMR (400 MHz, DMSO-d$_6$) δ ppm: 10.63 (s, 1 H), 8.21-8.28 (m, 2 H), 8.15-8.20 (m, 2 H), 7.49 (s, 2 H), 2.42 (s, 6 H).

Example 69

N-(2-(tert-butyl)pyridin-4-yl)-4-(5-(trifluoromethyl)-1,2,4-oxadiazol-3-yl)benzamide

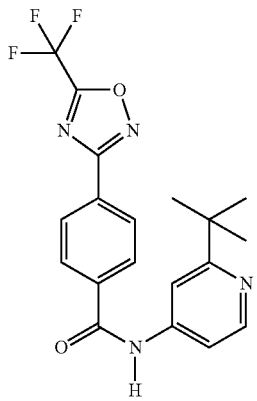 [SMILES: CC(C)(C)c1cc(NC(=O)c2ccc(-c3noc(C(F)(F)F)n3)cc2)ccn1]

Rt$_{MS1}$=1.89 min, ESIMS [M+H]$^+$=391.2, white powder.
$^1$H NMR (400 MHz, DMSO-d$_6$) δ ppm: 10.73 (br. s., 1 H), 8.46 (d, J=5.62 Hz, 1 H), 8.23-8.28 (m, 2 H), 8.17-8.22 (m, 2 H), 7.78-7.89 (m, 1 H), 7.65-7.76 (m, 1 H), 1.33 (s, 12H).

Example 70

N-(2-methylpyridin-4-yl)-4-(5-(trifluoromethyl)-1,2,4-oxadiazol-3-yl)benzamide

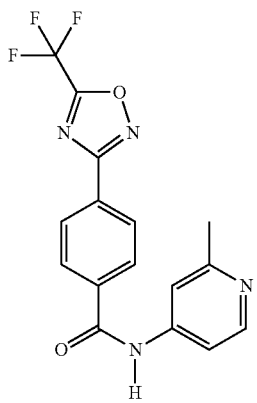

To compound 12b, 4-(5-trifluoromethyl-[1,2,4]oxadiazol-3-yl)-benzoic acid, (40 mg, 0.155 mmol) in DMF (516 μL) was added TFFH (82 mg, 0.310 mmol), 2-methylpyridin-4-amine (33.5 mg, 0.310 mmol) and DIPEA (81 μL, 0.465 mmol). The reaction was stirred at 50° C. for 1.5 h. The reaction mixture was subjected to purification by reverse phase prep-HPLC (gradient elution, water/MeCN both containing 0.1% TFA). Fractions containing the desired compound were combined and freeze-dried. The resulting material was dissolved in a mix of ACN/MeOH. They were loaded on a PL-HCO3 MP cartridge (from StratoSpheres™ SPE) and eluted with ACN (3 ml). The eluate was diluted with water (10 ml) and freeze-dried to yield the final compound.
Rt$_{MS1}$=1.61 min, ESIMS [M+H]$^+$=349.2, white powder.
$^1$H NMR (400 MHz, DMSO-d$_6$) δ ppm: 10.72 (s, 1 H), 8.37 (m, 1 H), 8.22-8.28 (m, 2 H), 8.16-8.21 (m, 2 H), 7.70 (m, 1 H), 7.60 (m, 1 H), 2.46 (s, 3 H).

Example 71

N-(2-fluoropyridin-4-yl)-4-(5-(trifluoromethyl)-1,2,4-oxadiazol-3-yl)benzamide

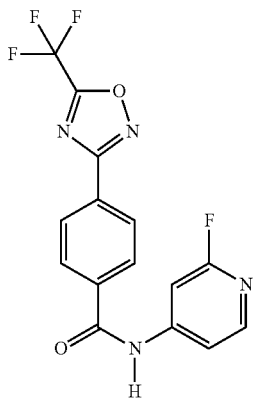 [SMILES: Cc1cc(NC(=O)c2ccc(-c3noc(C(F)(F)F)n3)cc2)ccn1]

N-(2-fluoropyridin-4-yl)-4-(5-(trifluoromethyl)-1,2,4-oxadiazol-3-yl)benzamide was prepared using a process analogous to that used in Example 70.

$Rt_{MS1}$=2.46 min, ESIMS [M+H]$^+$=353.2, white powder.

Examples 72-75

General method of amide bond formation with TFFH

To compound 12b, 4-(5-trifluoromethyl-[1,2,4]oxadiazol-3-yl)-benzoic acid, (30 mg, 0.116 mmol) in DMF (387 µL) were added TFFH (61.4 mg, 0.232 mmol) and DIPEA (60.9 µL, 0.349 mmol). It was stirred at RT for 1 h before the appropriate aminopyridine (0.232 mmol) was added and the reaction was stirred at 70° C. for 1.5 h. The reaction mixture was subjected to purification by reverse phase prep-HPLC (gradient elution, water/MeCN both containing 0.1% TFA). Fractions containing the desired compound were combined and freeze-dried. Due to their (moderate) volatility the compounds were tested in Test 1 as TFA salts.

Example 72

N-(2-hydroxypyridin-4-yl)-4-(5-(trifluoromethyl)-1,2,4-oxadiazol-3-yl)benzamide

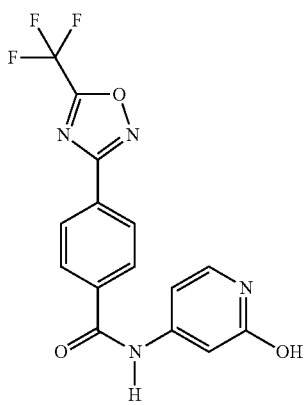 [SMILES: N#Cc1cc(NC(=O)c2ccc(-c3noc(C(F)(F)F)n3)cc2)ccn1]

$Rt_{MS1}$=1.79 min, ESIMS [M+H]$^+$=351.2, white powder.
$^1$H NMR (400 MHz, DMSO-d$_6$ as TFA salt) δ ppm: 11.35 (br. s., 1 H), 10.53 (s, 1 H), 8.23-8.25 (m, 2 H), 8.12-8.14 (m, 2 H), 7.37 (d, J=7.09 Hz, 1 H), 6.94 (d, J=1.96 Hz, 1 H), 6.61 (dd, J=7.21, 1.83 Hz, 1 H).

Example 73

N-(2-cyanopyridin-4-yl)-4-(5-(trifluoromethyl)-1,2,4-oxadiazol-3-yl)benzamide

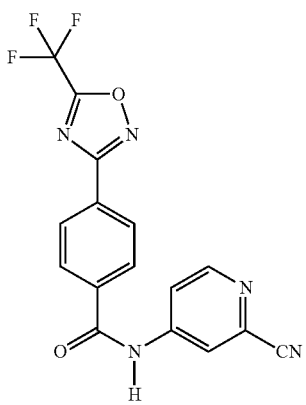

$Rt_{MS1}$=1.89 min, ESIMS [M+H]$^+$=360.2, white powder.
$^1$H NMR (400 MHz, DMSO-d$_6$ as TFA salt) δ ppm: 11.17 (s, 1 H), 8.69 (d, J=5.62 Hz, 1 H), 8.36 (d, J=2.20 Hz, 1 H), 8.28 (m, 2 H), 8.21 (m, 2 H), 8.06 (dd, J=5.62, 1.96 Hz, 1 H).

Example 74

4-(5-(Trifluoromethyl)-1,2,4-oxadiazol-3-yl)-N-(2-(trifluoromethyl)pyridin-4-yl)benzamide

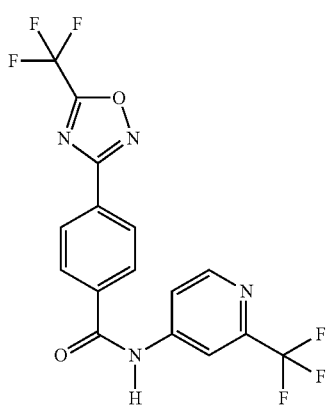 [SMILES: O=C(Nc1ccnc(C(F)(F)F)c1)c1ccc(-c2noc(C(F)(F)F)n2)cc1]

$Rt_{MS1}$=2.72 min, ESIMS [M+H]$^+$=403.2, white solid.
$^1$H NMR (400 MHz, DMSO-d$_6$ as TFA salt) δ ppm: 11.15 (s, 1 H), 8.71 (d, J=5.38 Hz, 1 H), 8.20-8.34 (m, 6 H), 8.08 (d, J=5.38 Hz, 1 H).

Example 75

N-(2-chloropyridin-4-yl)-4-(5-(trifluoromethyl)-1,2,4-oxadiazol-3-yl)benzamide

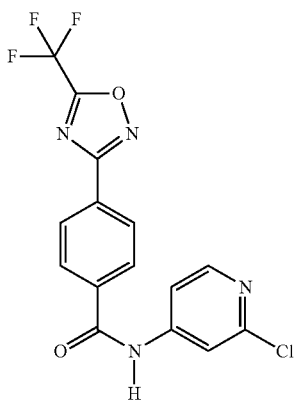 [SMILES: O=C(Nc1ccnc(Cl)c1)c1ccc(-c2noc(C(F)(F)F)n2)cc1]

Rt$_{MS1}$=2.53 min, ESIMS [M+H]$^+$=369.1, white powder.
$^1$H NMR (400 MHz, DMSO-d$_6$ as TFA salt) δ ppm: 11.02 (s, 1 H), 8.35 (d, J=5.62 Hz, 1 H), 8.27 (m, 2 H), 8.20 (m, 2 H), 7.98 (d, J=1.47 Hz, 1 H), 7.77 (dd, J=5.62, 1.71 Hz, 1 H).

Examples 76-80

General method for cleavage of BOC protecting group

Examples 76 to 80 were made using the general method described in Example 12 except that Boc protected products were dissolved in DCM (0.2 molar) and TFA added. The reaction was stirred for 1 h at RT, before the solvent was condensed in vacuum. The reaction mixture was subjected to purification by reverse phase prep-HPLC (gradient elution, water/MeCN both containing 0.1% TFA). Fractions containing the desired compound were combined and freeze-dried. The resulting material was dissolved in a mix of ACN/MeOH. They were loaded on a PL-HCO3 MP cartridge (from Strato-Spheres™ SPE) and eluted with ACN (3 ml). The eluate was diluted with water (10 ml) and freeze-dried to yield the final compound.

Example 76

N-(piperidin-4-yl)-4-(5-(trifluoromethyl)-1,2,4-oxadiazol-3-yl)benzamide

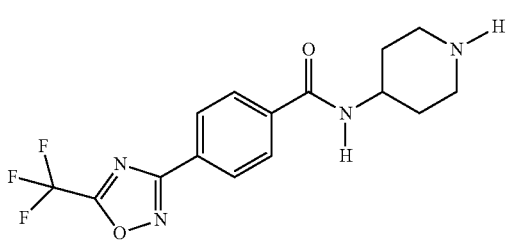 [SMILES: O=C(NC1CCNCC1)c1ccc(-c2noc(C(F)(F)F)n2)cc1]

Rt$_{MS1}$=1.40 min, ESIMS [M+H]$^+$=341.3, white powder.
$^1$H NMR (400 MHz, DMSO-d$_6$) δ ppm: 8.50 (d, J=8.31 Hz, 1 H), 8.12-8.18 (m, 2 H), 8.04-8.10 (m, 2 H), 3.85 (m, 1 H), 2.92-3.00 (m, 2 H), 2.52-2.57 (m, 2 H), 1.71-1.79 (m, 2 H), 1.37-1.50 (m, 2 H).

Example 77

N-(2-aminocyclohexyl)-4-(5-(trifluoromethyl)-1,2,4-oxadiazol-3-yl)benzamide

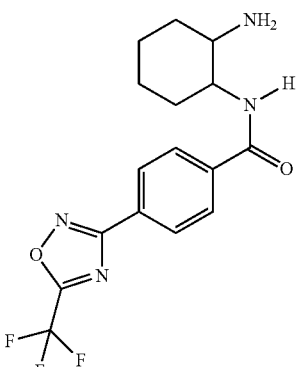

Rt$_{MS1}$=1.52 min, ESIMS [M+H]$^+$=355.3, white powder.
1 H NMR (400 MHz, DMSO-d$_6$) δ ppm: 8.39 (d, J=8.07 Hz, 1 H), 8.15-8.17 (m, 2 H), 8.08-8.10 (m, 2 H), 3.48 (m, 1 H), 2.60 (m, 1 H), 1.63-1.88 (m, 5.5H, rota), 1.09-1.29 (m, 4.5H, rota).

Example 78

N-(piperidin-2-ylmethyl)-4-(5-(trifluoromethyl)-1,2,4-oxadiazol-3-yl)benzamide

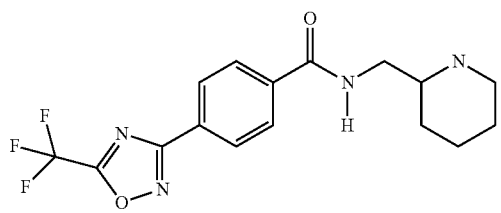 [SMILES: O=C(NCC1CCCCN1)c1ccc(-c2noc(C(F)(F)F)n2)cc1]

Rt$_{MS1}$=1.44 min, ESIMS [M+H]$^+$=355.3, white powder.
$^1$H NMR (400 MHz, DMSO-d$_6$) δ ppm: 8.63 (t, J=5.62 Hz, 1 H), 8.15-8.17 (m, 2 H), 8.06-8.08 (m, 2 H), 3.12-3.29 (m, 2 H), 2.93 (m, 1 H), 2.62 (m, 1 H), 2.43 (m, 1 H), 1.74 (m, 1 H), 1.61 (m, 1 H), 1.48 (m, 1 H), 1.18-1.36 (m, 2 H), 1.00 (m, 1 H).

Example 79

N-(piperidin-3-yl)-4-(5-(trifluoromethyl)-1,2,4-oxadiazol-3-yl)benzamide

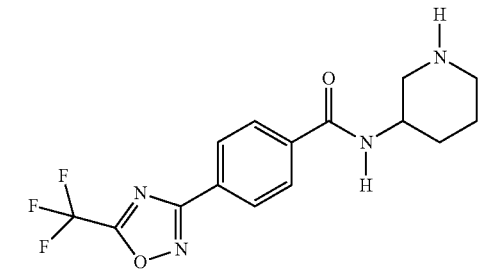 [SMILES: O=C(NC1CCCNC1)c1ccc(-c2noc(C(F)(F)F)n2)cc1]

Rt$_{MS1}$=1.42 min, ESIMS [M+H]$^+$=341.6, white powder.
$^1$H NMR (400 MHz, DMSO-d$_6$) δ ppm: 8.38 (d, J=7.83 Hz, 1 H), 8.10-8.20 (m, 2 H), 8.02-8.10 (m, 2 H), 3.83 (m, 1 H), 2.97 (d, J=15.16 Hz, 1 H), 2.80 (d, J=12.23 Hz, 1 H), 2.60 (m, 1 H), 2.33-2.44 (m, 2 H) 1.88 (m, 1 H) 1.65 (m, 1 H) 1.31-1.49 (m, 2 H).

Example 80

N-(pyrrolidin-3-yl)-4-(5-(trifluoromethyl)-1,2,4-oxadiazol-3-yl)benzamide

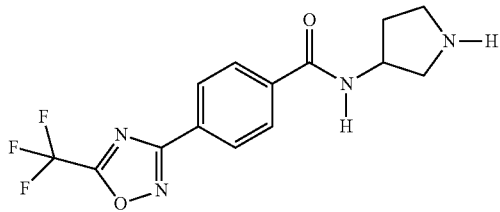 [SMILES: O=C(NC1CCNC1)c1ccc(-c2noc(C(F)(F)F)n2)cc1]

Rt$_{MS1}$=1.37 min, ESIMS [M+H]$^+$=327.3, white powder.
$^1$H NMR (400 MHz, DMSO-d$_6$) δ ppm: 8.57 (d, J=8.56 Hz, 1 H), 8.12-8.21 (m, 2 H), 8.02-8.12 (m, 2 H), 4.32 (m, 1 H), 2.84-3.06 (m, 2 H), 2.61-2.82 (m, 2 H), 2.54 (m, 1H), 1.63-2.01 (m, 2H).

Example 81

(R)—N-(1-(dimethylamino)propan-2-yl)-4-(5-(trifluoromethyl)-1,2,4-oxadiazol-3-yl)benzamide

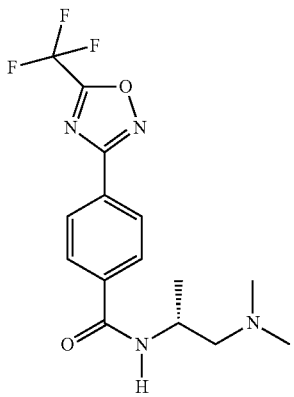 [SMILES: C[C@H](CN(C)C)NC(=O)c1ccc(-c2noc(C(F)(F)F)n2)cc1]

To a solution of compound 12b, 4-(5-trifluoromethyl-[1,2,4]oxadiazol-3-yl)-benzoic acid, (120 mg, 0.465 mmol) in DCM (1549 µL) was added COMU (268.0 mg, 0.604 mmol) and DIPEA (243 µL) at rt. Intermediate 81d (90 mg, 0.511 mmol) was added after 15 min and the solution was stirred at 50° C. for 1.5 hrs. The volatile solvent was removed, the crude was dissolved in MeOH and subjected to purification by reverse phase prep-HPLC (gradient elution, water/ACN both containing 0.1% TFA). Fractions containing the desired product were combined and freeze-dried. The resulting material was dissolved in a mix of ACN/MeOH, loaded on a PL-HCO3 MP cartridge (from StratoSpheres™ SPE) and eluted with ACN (3 ml). The eluate was diluted with water (10 ml) and freeze-dried to yield product 81 (58.4 mg, 0.169 mmol, 36.3% yield) as white solid.

Rt$_{MS1}$=3.03 min, ESIMS [M+H]$^+$=343.2, white solid.
$^1$H NMR (400 MHz, DMSO-d$_6$) δ ppm: 8.38 (m, 1 H), 8.16-8.20 (m, 2 H), 8.01-8.07 (m, 2 H), 4.16 (m, 1 H), 2.41 (m, 1 H), 2.17-2.30 (m, 7 H), 1.15 (d, J=6.60 Hz, 3 H).

The chiral amine used in the synthesis of (R)—N-(1-(dimethylamino)propan-2-yl)-4-(5-(trifluoromethyl)-1,2,4-oxadiazol-3-yl)benzamide was prepared as follows. The first two steps were carried out as described in Chirality (2003), Vol. 15(9), 777-782.

Intermediate 81a:
(R)-2-tert-butoxycarbonylamino-propionic acid

To a suspension of D-alanine (1 g, 11.22 mmol) in water (5.6 mL)/MeOH (2.80 mL) (2:1) K$_2$CO$_3$ (1.55 g, 11.22 mmol) was added at 0-5° C., followed by a solution of Boc$_2$OO (2.61 mL, 11.22 mmol) in MeOH (2.80 mL) over 5 min. The resulting suspension was stirred for 23 h at rt. The reaction mixture was poured into water and acidified to pH=3 with aqueous citric acid solution. The white cloudy solution was extracted with DCM (3×). Organic layers were combined, washed with brine, dried over MgSO$_4$, filtered and the solvent removed to yield 1.78 g, 9.43 mmol (R)-2-tert-butoxycarbonylamino-propionic acid.
$^1$H NMR (400 MHz, DMSO-d$_6$) δ ppm: 12.14-12.63 (m, 1 H), 6.97-7.19 (m, 1 H), 3.76-4.00 (m, 1 H), 1.38 (s, 9 H), 1.22 (d, J=7.09 Hz, 3 H).

Intermediate 81b:
((R)-1-Dimethylcarbamoyl-ethyl)-carbamic acid tert-butyl ester To a solution of (R)-2-tert-Butoxycarbonylamino-propionic acid (1.78 g, 9.43 mmol) in DCM (7.85 mL) was added portion wise DCC (2.14 g, 10.37 mmol) cooled in an ice bath. After stirring at room temperature for 30 min, dimethylamine (2 M in THF) (6.13 mL, 12.25 mmol) was added. The resulting solution was stirred overnight (18 h) until reaction was completed. The reaction mixture was filtered through silica gel and eluted with Ethyl acetate. Then the filtrate was evaporated off. The solvent was removed to yield (1.71 g, 7.12 mmol, 76% yield, 90% purity) ((R)-1-Dimethylcarbamoyl-ethyl)-carbamic acid tert-butyl ester as a yellow oil. The product was used in the next step without further purification.
$^1$H NMR (400 MHz, DMSO-d$_6$) δ ppm 6.84 (m, 1 H), 4.32 (m, 1 H). 3.00 (s, 3 H), 2.82 (s, 3 H), 1.37 (s, 9 H), 1.12 (d, J=6.85 Hz, 3 H).

Intermediate 81c: ((R)-2-Dimethylamino-1-methyl-ethyl)-carbamic acid tert-butyl ester Reduction was carried out according to Chem. Eur. J. (2008), 14(17), 51116-5119. To an ice-cooled lithium aluminum hydride (in Et$_2$O) (21.35 mL, 21.35 mmol) solution was added drop wise a solution of ((R)-1-dimethylcarbamoyl-ethyl)-carbamic acid tert-butyl ester (1.7105 g, 7.12 mmol) in Et$_2$O (2-3 mL). The reaction mixture was stirred at 0° C. until disappearance of the starting material. The reaction mixture was carefully quenched by sequential addition of water (1.2 mL), 15% (w/w) NaOH (1.2 mL) and water (3.6 mL). Then EtOAc was added and the solids were filtered and washed with EtOAc. The filtrated was dried over MgSO$_4$, filtered and evaporated off. Then the crude was dissolved in DCM, filtered and evaporated off to give 1.4543 g, 6.47 mmol, 91% yield ((R)-2-Dimethylamino-1-methyl-ethyl)-carbamic acid tert-butyl ester as yellowish oil. The crude was used without any further purification and characterization.

Intermediate 81d:
(R)—N,N-dimethyl-propane-1,2-diamine

A solution of ((R)-2-dimethylamino-1-methyl-ethyl)-carbamic acid tert-butyl ester (1.42 g, 6.30 mmol) in HCl (4M in dioxane) (15.74 mL, 63.0 mmol) was stirred at room temperature for 20 h and a white precipitate was formed. The white solid was filtered and suspended in EtOAc. The white cloudy solution was filtered and dried to give (R)—N,N-dimethyl-propane-1,2-diamine (777.1 mg, 4.39 mmol, 69.8% yield) as a white solid.

$^1$H NMR (400 MHz, DMSO-d$_6$) δ ppm: 10.65-11.23 (m, 1 H), 8.63 (br. s., 3 H), 3.77 (br.s., 1 H), 3.41 (dd, J=13.69, 7.58 Hz, 1 H), 3.25 (dd, J=13.69, 3.67 Hz, 1 H), 2.83 (br. s., 6 H), 1.33 (d, J=6.60 Hz, 3 H).

Examples 82-87

General method of amide bond formation with oxalylchloride

To a solution of compound 12b, 4-(5-trifluoromethyl-[1,2,4]oxadiazol-3-yl)-benzoic acid, (80 mg, 0.310 mmol), oxalyl chloride (81 μL, 0.930 mmol) and cat. DMF (2-3 droplets) in dry DCM (1 mL) was stirred at room temperature for 3 h. The reaction mixture was cooled to 0° C., then a solution of the appropriate amine (0.372 mmol) and DIPEA (173 μL, 0.992 mmol) in dry DCM (1 mL) added slowly and the reaction mixture stirred for 5-10 min. at 0° C. The resulting solution was allowed to warm up to rt overnight. The reaction mixture was concentrated under high vacuum and subjected to purification by reverse phase prep-HPLC (gradient elution, water/ACN both containing 0.1% TFA). Fractions containing the desired compound were combined and freeze-dried. The resulting material was dissolved in a mix of ACN/MeOH, then loaded onto a PL-HCO3 MP cartridge (from StratoSpheres™ SPE) and eluted with ACN (3 ml). The eluate was diluted with water (10 ml) and freeze-dried to yield the final compound.

Example 82

(S)—N-(1-(dimethylamino)propan-2-yl)-4-(5-(trifluoromethyl)-1,2,4-oxadiazol-3-yl)benzamide

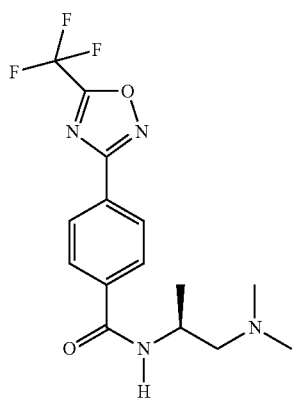 [SMILES: C[C@@H](CN(C)C)NC(=O)c1ccc(-c2noc(C(F)(F)F)n2)cc1]

Rt$_{MS1}$=3.03 min, ESIMS [M+H]$^+$=343.2, white solid.
$^1$H NMR (400 MHz, DMSO-d$_6$) δ ppm: 8.38 (m, 1 H), 8.12-8.20 (m, 2 H), 8.00-8.11 (m, 2 H), 4.16 (m, 1 H), 2.41 (m, 1 H), 2.17-2.30 (m, 7 H), 1.15 (d, J=6.60 Hz, 3 H).

Example 83

(S)—N-(1-(dimethylamino)-3-methylbutan-2-yl)-4-(5-(trifluoromethyl)-1,2,4-oxadiazol-3-yl)benzamide

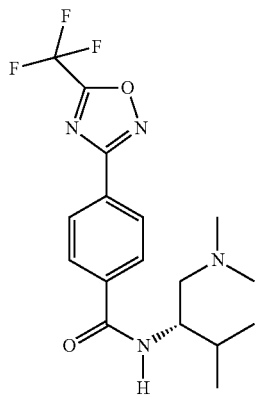 [SMILES: CC(C)[C@@H](CN(C)C)NC(=O)c1ccc(-c2noc(C(F)(F)F)n2)cc1]

Rt$_{MS1}$=3.53 min, ESIMS [M+H]$^+$=371.2, white solid.
$^1$H NMR (400 MHz, DMSO-d$_6$) δ ppm: 8.23 (m, 1 H), 8.13-8.19 (m, 2 H), 8.02-8.09 (m, 2H), 4.02 (m, 1 H), 2.29 (m, 1 H), 2.16 (s, 6 H), 1.84 (m, 1 H), 0.91 (t, J=7.09 Hz, 6 H).

Example 84

(R)—N-(1-(dimethylamino)-3-methylbutan-2-yl)-4-(5-(trifluoromethyl)-1,2,4-oxadiazol-3-yl)benzamide

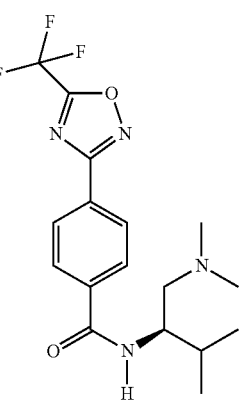

Rt$_{MS1}$=3.53 min, ESIMS [M+H]$^+$=371.2, white solid.
$^1$H NMR (400 MHz, DMSO-d$_6$) δ ppm: 8.24 (m, 1 H), 8.13-8.19 (m, 2 H), 8.02-8.10 (m, 2H), 4.03 (m, 1 H), 2.45 (m, 1H), 2.28 (m, 1 H), 2.16 (s, 6 H), 1.84 (m, 1 H), 0.91 (t, J=7.09 Hz, 6 H).

Example 85

(R)—N-(1-(dimethylamino)-4-methylpentan-2-yl)-4-(5-(trifluoromethyl)-1,2,4-oxadiazol-3-yl)benzamide

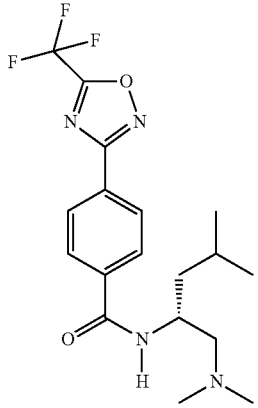 [SMILES: CC(C)C[C@H](CN(C)C)NC(=O)c1ccc(-c2noc(C(F)(F)F)n2)cc1]

$Rt_{MS1}$=3.85 min, ESIMS [M+H]$^+$=385.2, white solid.
$^1$H NMR (400 MHz, DMSO-d$_6$) δ ppm: 8.30 (m, 1 H), 8.13-8.20 (m, 2 H), 8.00-8.09 (m, 2 H), 4.22 (m, 1 H), 2.34 (m, 1H), 2.22 (m, 1 H), 2.16 (s, 6 H), 1.33-1.50 (m, 2 H) 1.57-1.68 (m, 1H), 0.90 (d, J=6.60 Hz, 6 H).

Example 86

(R)—N-(pyyrrolidin-3-yl)-4-(5-(trifluoromethyl)-1,2,4-oxadiazol-3-yl)benzamide

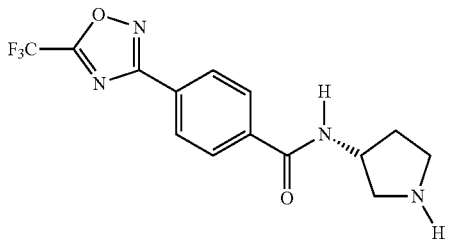

$Rt_{MS1}$=1.41 min, ESIMS [M+H]$^+$=327.3, white solid.
$^1$H NMR (400 MHz, DMSO-d$_6$) δ ppm: 8.15-8.17 (m, 2 H), 8.06-8.08 (m, 2 H), 4.45 (m, 0.2H, rota), 4.34 (m, 0.8 H, rota), 3.4-3.7 (m, 1.2 H, rota), 2.91-3.00 (m, 1.2 H, rota), 2.69-2.78 (m, 1.6H), 2.0 (m, 1.4 H), 1.66-1.72 (m, 0.6 H, rota).

Example 87

(S)—N-(pyrrolidin-3-yl)-4-(5-(trifluoromethyl)-1,2,4-oxadiazol-3-yl)benzamide

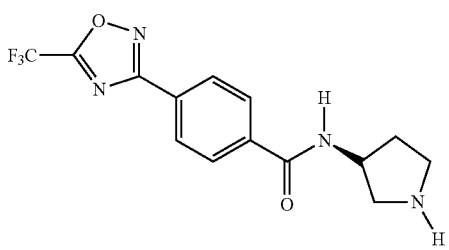

$Rt_{MS1}$=1.41 min, ESIMS [M+H]$^+$=327.3, white solid.
$^1$H NMR (400 MHz, MeOD-d$_4$) δ ppm: 8.24 (d, J=8.56 Hz, 2 H), 8.04 (d, J=8.56 Hz, 2 H), 4.50-4.58 (m, 1 H), 3.26-3.31 (m, 1 H), 3.15-3.24 (m, 1 H), 3.02-3.10 (m, 1 H), 2.94-3.02 (m, 1H), 2.19-2.33 (m, 1 H), 1.84-2.00 (m, 1 H).

Example 88

(R)—N-(1-(dimethylamino)propan-2-yl)-2-fluoro-4-(5-(trifluoromethyl)-1,2,4-oxadiazol-3-yl)benzamide

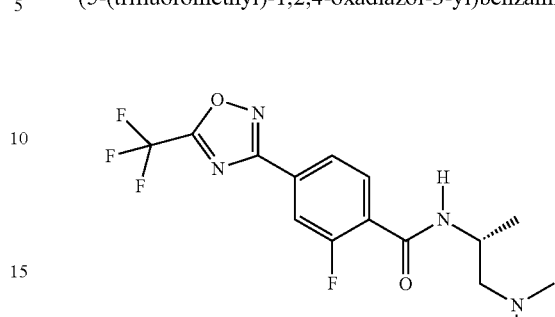

To a solution of intermediate 88b (80 mg, 0.29 mmol) in DCM (966 μL) was added COMU (167 mg, 0.377 mmol) and DIPEA (101 μL) at rt. Intermediate 81d (55.8 mg, 0.319 mmol) was added after 15 min and the solution was stirred at 50° C. for 1.5 hrs. The volatile solvent was removed, the crude was dissolved in MeOH and subjected to purification by reverse phase prep-HPLC (gradient elution, water/ACN both containing 0.1% TFA). Fractions containing the desired product were combined and freeze-dried. The resulting material was dissolved in a mix of ACN/MeOH, loaded on a PL-HCO3 MP cartridge (from StratoSpheres™ SPE) and eluted with ACN (3 ml). The eluate was diluted with water (10 ml) and freeze-dried to yield product 88 (72.8 mg, 0.198 mmol, 68.3% yield) as yellow oil.

$Rt_{MS1}$=3.09 min, ESIMS [M+H]$^+$=361.2, yellow oil
$^1$H NMR (400 MHz, DMSO-d$_6$) δ ppm: 8.44 (d, J=5.14 Hz, 1 H), 7.91-8.06 (m, 2 H), 7.86 (t, J=7.34 Hz, 1 H), 4.27 (br. s., 1 H), 3.57 (s, 6 H), 3.32 (s, 2 H), 1.18 (d, J=6.60 Hz, 3 H).

The 2-fluoro-4-(5-(trifluoromethyl)-1,2,4-oxadiazol-3-yl) benzoic acid used in the coupling reaction with COMU was prepared as follows.

Intermediate 88a:
2-Fluoro-4-(N-hydroxycarbamimidoyl)-benzoic acid

To a solution of 4-Cyano-2-fluorobenzoic acid (1 g, 6.06 mmol) in EtOH (10.09 mL) was added NH2OH.HCl (0.884 g, 12.72 mmol) previously dissolved in water (5 mL) and aqueous solution K$_2$CO$_3$ (1.339 g, 9.69 mmol) in water (15 mL). Then 8-hydroxyquinone (0.011 g, 0.079 mmol) was added. The resulting solution was stirred at reflux for 4 h. EtOH was evaporated from the reaction mixture, then acidified to pH 3 with aqueous HCl (2 N) solution. The precipitate was filtered, washed with water and dried to yield 2-fluoro-4-(N-hydroxycarbamimidoyl)-benzoic acid (786.3 mg, 3.89 mmol, 64.2% yield) as yellowish solid. The crude was used without further purification. $^1$H NMR (400 MHz, DMSO-d$_6$) δ ppm: 13.21 (m, 1 H), 10.01 (s, 1 H), 7.85 (t, J=7.95 Hz, 1 H), 7.44-7.69 (m, 2 H), 5.99 (br. s., 2 H).

Intermediate 88b: 2-Fluoro-4-(5-(trifluoromethyl)-1,2,4-oxadiazol-3-yl)benzoic acid To a suspension of 2-fluoro-4-(N-hydroxycarbamimidoyl)-benzoic acid (786.3 mg, 3.89 mmol) in THF (13 ml)

was added drop wise TFAA (0.824 ml, 5.83 mmol) over 30 min. The solution was stirred for 4 h. After evaporation, crude product was washed with EtOAc and filtered on a glass sinter funnel. After drying, 2-fluoro-4-(5-(trifluoromethyl)-1,2,4-oxadiazol-3-yl)benzoic acid (1.044 g, 3.71 mmol, 95% yield) was obtained as a greenish solid.

$Rt_{MS1}$=2.30 min, ESIMS [M+H]$^+$=250.1, greenish solid.

$^1$H NMR (400 MHz, DMSO-d$_6$) δ ppm: 13.66 (m, 1 H), 8.11 (t, J=7.70 Hz, 1 H), 8.00 (d, J=8.31 Hz, 1 H), 7.94 (d, J=11.00 Hz, 1 H).

Examples 89-95

General method for coupling with COMU

To a suspension of 2-fluoro-4-(5-(trifluoromethyl)-1,2,4-oxadiazol-3-yl)benzoic acid (1 eq) and COMU (1 eq) in DCM was added DIPEA (1 eq). The red solution was stirred at rt and then the appropriate amine (1 eq) previously dissolved in DCM+DIPEA (1 eq) was added. The resulting solution was stirred at 50° C. for 1.5 h. The reaction mixture was concentrated under high vacuum and subjected to purification by reverse phase prep-HPLC (gradient elution, water/ACN both containing 0.1% TFA). Fractions containing the desired compound were combined and freeze-dried. The resulting material was dissolved in dioxane, loaded on a PL-HCO3 MP cartridge (from StratoSpheres™ SPE) and eluted with dioxane (3 ml). The eluate was diluted with water (3 ml) and freeze-dried to yield the final compound.

Example 89

(R)—N-(1-(dimethylamino)-3-methylbutan-2-yl)-2-fluoro-4-(5-(trifluoromethyl)-1,2,4-oxadiazol-3-yl)benzamide

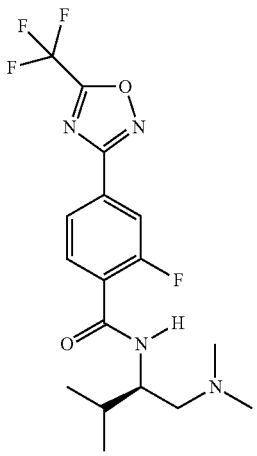 [SMILES: CC(C)[C@H](CN(C)C)NC(=O)c1ccc(-c2noc(C(F)(F)F)n2)cc1F]

$Rt_{MS1}$=3.57 min, ESIMS [M+H]$^+$=389.2, yellow oil $^1$H NMR (400 MHz, DMSO-d$_6$) δ ppm: 8.43 (d, J=9.05 Hz, 1 H), 7.89-8.13 (m, 3 H), 4.25 (m, 1H), 3.26-3.34 (m, 2 H), 2.75-2.94 (m, 6 H), 1.85 (m, 1 H), 0.96 (t, J=7.34 Hz, 6 H).

Example 90

N-(2,6-dimethylpyridin-4-yl)-2-fluoro-4-(5-(trifluoromethyl)-1,2,4-oxadiazol-3-yl)benzamide

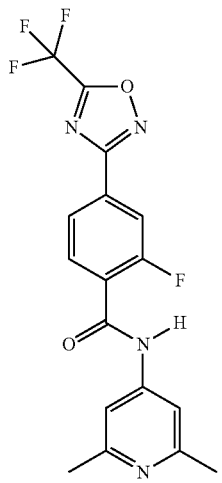 [SMILES: Cc1cc(NC(=O)c2ccc(-c3noc(C(F)(F)F)n3)cc2F)cc(C)n1]

$Rt_{MS1}$=3.58 min, ESIMS [M+H]$^+$=381.1, yellowish oil $^1$H NMR (400 MHz, DMSO-d$_6$) δ ppm: 10.83 (s, 1 H), 7.97-8.12 (m, 2 H), 7.92 (t, J=7.46 Hz, 1H), 7.38 (s, 2 H), 2.41 (s, 6 H).

Example 91

2-fluoro-N-(1-hydroxyypropan-2-yl)-4-(5-(trifluoromethyl)-1,2,4-oxadiazol-3-yl)benzamide

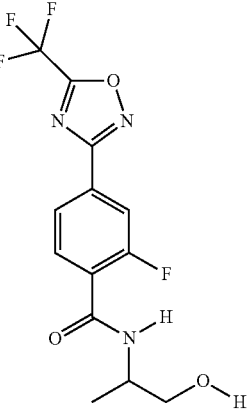

$Rt_{MS1}$=3.98 min, ESIMS [M+H]$^+$=334.1, deep pink solid $^1$H NMR (400 MHz, DMSO-d$_6$) δ ppm: 8.28 (d, J=8.07 Hz, 1H), 7.86-8.03 (m, 2 H), 7.82 (t, J=7.58 Hz, 1 H), 4.78 (t, J=5.62 Hz, 1 H), 4.00 (ddd, J=13.57, 6.72, 6.60 Hz, 1 H), 3.46 (m, 1H), 3.44 (m, 1H), 1.14 (d, J=6.85 Hz, 3 H).

Example 92

(R)—N-(1-(dimethylamino)-3-phenylpropan-2-yl)-4-(5-(trifluoromethyl)-1,2,4-oxadiazol-3-yl)benzamide

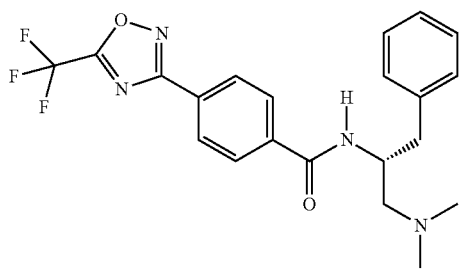 [SMILES: CN(C)C[C@@H](Cc1ccccc1)NC(=O)c1ccc(-c2noc(C(F)(F)F)n2)cc1]

$Rt_{MS1}$=3.83 min, ESIMS [M+H]$^+$=419.2, white solid
$^1$H NMR (400 MHz, MeOD) δ ppm: 8.13-8.29 (m, 2 H), 7.87-7.98 (m, 2 H), 7.14-7.29 (m, 5H), 4.64 (m, 1 H), 2.69-3.04 (m, 4 H), 2.62 (s, 6H).

Example 93

(S)—N-(1-(dimethylamino)-3-phenylpropan-2-yl)-4-(5-(trifluoromethyl)-1,2,4-oxadiazol-3-yl)benzamide

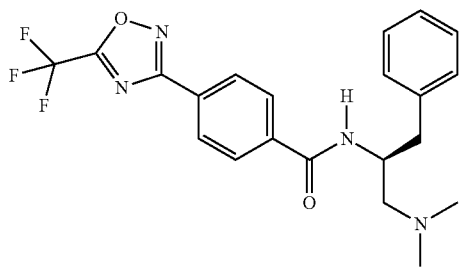 [SMILES: CN(C)C[C@H](Cc1ccccc1)NC(=O)c1ccc(-c2noc(C(F)(F)F)n2)cc1]

$Rt_{MS1}$=3.82 min, ESIMS [M+H]$^+$=419.2, yellowish solid
$^1$H NMR (400 MHz, MeOD) δ ppm: 8.21 (m, 2 H), 7.92 (m, 2H), 7.26-7.37 (m, 4 H), 7.21 (m, 1 H), 4.65 (m, 1 H), 2.96-3.15 (m, 2 H), 2.78-2.96 (m, 2 H), 2.62 (br. s., 6 H).

Example 94

N-(1-(dimethylamino)propan-2-yl)-N-methyl-4-(5-(trifluoromethyl)-1,2,4-oxadiazol-3-yl)benzamide

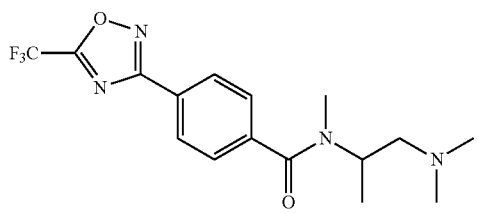 [SMILES: CC(CN(C)C)N(C)C(=O)c1ccc(-c2noc(C(F)(F)F)n2)cc1]

$Rt_{MS1}$=3.56 min, ESIMS [M+H]$^+$=357.2, yellowish solid.
$^1$H NMR (400 MHz, DMSO-d$_6$, 373K) δ ppm: 8.07-8.09 (m, 2 H), 7.54-7.56 (m, 2 H), 4.40 (bs, 1 H), 2.90-2.94 (m, 2 H), 2.79 (s, 3 H), 2.15 (s, 6H), 1.15 (m, 3H).

Example 95

(R)-2-fluoro-N-(pyyrrolidin-3-yl)-4-(5-(trifluoromethyl)-1,2,4-oxadiazol-3-yl)benzamide

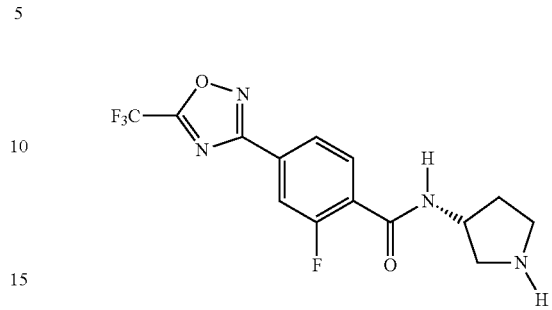

$Rt_{MS1}$=1.39 min, ESIMS [M+H]$^+$=345.3, yellowish solid.
$^1$H NMR (400 MHz, DMSO-d$_6$) δ ppm: 7.24 (d, J=1.47 Hz, 1 H), 7.15 (d, J=10.76 Hz, 1 H), 7.07 (t, 1 H), 3.71 (m, 1 H), 2.45-2.55 (m, 3 H), 2.34 (m, 1 H), 2.24 (m, 1 H), 2.13 (m, 1 H), 1.45 (m, 1 H), 1.07 (m, 1 H).

Example 96

N-phenyl-4-(5-(trifluoromethyl)-1,2,4-oxadiazol-3-yl)benzenesulfonamide

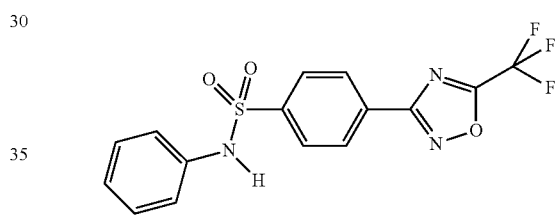

N-Hydroxy-4-phenylsulfamoyl-benzamidine (175 mg, 0.571 mmol) was dissolved in pyridine (1902 μL). TFAA (161 μL, 1.141 mmol) was added and the reaction mixture was stirred at 75° C. for 12 h. The mixture was diluted with EtOAc and water+0.1N HCl. The phases were separated, the aqueous phase extracted and the combined organic layers were washed with 0.1N HCl and brine. After drying over magnesium sulfate, the solution was concentrated under vacuum to give a yellow solid. The crude product was subjected to purification by reverse phase prep-HPLC (gradient elution, water/MeCN both containing 0.1% TFA). Fractions containing the desired compound were combined and freeze-dried. The resulting mixture was dissolved in a mix of dioxane/water. They were load in a PL-HCO3 MP cartridge (from StratoSpheres™ SPE) and eluted with dioxane. The eluate was freeze-dried to yield the final compound.

$Rt_{UPLC}$=1.17 min, ESIMS [M+H]$^-$=338, white solid.
$^1$H NMR (400 MHz, DMSO-d$_6$) δ ppm: 10.46 (s, 1 H), 8.23 (m, J=8.56 Hz, 2 H), 7.96 (m, J=8.80 Hz, 2 H), 7.24 (m, 2 H), 7.08 (m, 3 H).

Intermediate 96a:
4-Cyano-N-phenyl-benzenesulfonamide

To a solution of 4-cyanobenzene-1-sulfonyl chloride (200 mg, 0.992 mmol) in pyridine (4960 μL) was added aniline (100 μL, 1.091 mmol) and the reaction mixture stirred overnight at rt. The reaction mixture was diluted with EtOAc and water+0.1N HCl. The phases were separated, the aqueous phase extracted and the combined organic layers washed with 0.1N HCl and brine. After drying over magnesium sulfate, the solution was concentrated under vacuum to yield 4-cyano-N-phenyl-benzenesulfonamide 198 mg (0.652 mmol) of yellow oil.

$Rt_{UPLC}$=0.92 min, ESIMS [M+H]$^+$=259, yellow oil
$^1$H NMR (400 MHz, CHLOROFORM-d) δ ppm: 7.86 (d, J=8.56 Hz, 2 H), 7.74 (d, J=8.56 Hz, 2H), 7.31 (s, 2 H), 7.19 (m, 1 H), 7.07 (d, J=9.54 Hz, 2 H).

Intermediate 96b:
N-Hydroxy-4-phenylsulfamoyl-benzamidine

4-Cyano-N-phenyl-benzenesulfonamide (crude) (198 mg, 0.652 mmol), Sodium bicarbonate (547 mg, 6.52 mmol) and NH$_2$OH.HCl (453 mg, 6.52 mmol) was dissolved in EtOH (2172 μL) and the resulting solution stirred overnight at 60° C. The mixture was diluted with EtOAc and water. The water phase was extracted and the combined organic phases washed with brine, then dried over magnesium sulfate. After evaporation of the solvent, 175 mg (0.571 mmol) of a white solid was obtained. The product was used without purification in the next step.

$Rt_{UPLC}$=0.67 min, ESIMS [M+H]$^+$=292
$^1$H NMR (400 MHz, DMSO-d$_6$) δ ppm: 10.30 (s, 1 H), 9.92 (s, 1 H), 7.80 (m, J=8.56 Hz, 2 H), 7.73 (m, J=8.56 Hz, 2 H), 7.22 (t, J=7.83 Hz, 2 H), 7.09 (d, J=7.82 Hz, 2 H), 7.02 (m, 1 H).

The following Examples 97-102 were made using a method analogous to that described above for Example 96.

Example 97

N-benzyl-4-(5-(trifluoromethyl)-1,2,4-oxadiazol-3-yl)benzenesulfonamide

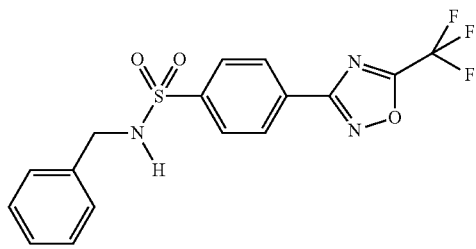 [SMILES: O=S(=O)(NCc1ccccc1)c1ccc(-c2noc(C(F)(F)F)n2)cc1]

$Rt_{UPLC}$=1.19 min, ESIMS [M+H]$^-$=382, white solid.
$^1$H NMR (400 MHz, DMSO-d$_6$) δ ppm: 8.42 (t, J=6.36 Hz, 1 H), 8.24 (m, 2 H), 8.00 (m, 2 H), 7.26 (m, 5 H), 4.06 (d, J=6.36 Hz, 2 H).

Example 98

N-(2-(dimethylamino)ethyl)-4-(5-(trifluoromethyl)-1,2,4-oxadiazol-3-yl)benzenesulfonamide

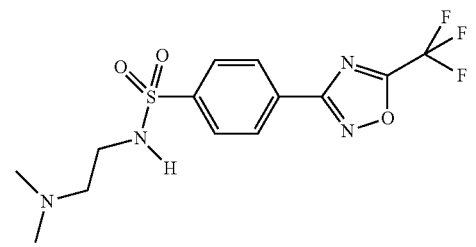 [SMILES: CN(C)CCNS(=O)(=O)c1ccc(-c2noc(C(F)(F)F)n2)cc1]

$Rt_{UPLC}$=0.71 min, ESIMS [M+H]$^+$=365, white solid.
$^1$H NMR (400 MHz, DMSO-d$_6$) as TFA salt δ ppm: 9.57 (br. s., 1 H), 8.32 (m, 2 H), 8.25 (m, 1H), 8.06 (d, J=8.56 Hz, 2 H), 3.15 (m, 4 H), 2.79 (s, 6 H).

Example 99

N-(2-(dimethylamino)ethyl)-N-methyl-4-(5-(trifluoromethyl)-1,2,4-oxadiazol-3-yl)benzenesulfonamide

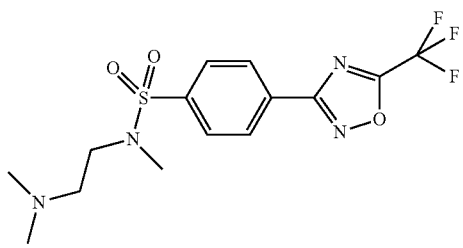 [SMILES: CN(C)CCN(C)S(=O)(=O)c1ccc(-c2noc(C(F)(F)F)n2)cc1]

$Rt_{UPLC}$=0.75 min, ESIMS [M+H]$^+$=379, colorless oil.
$^1$H NMR (400 MHz, DMSO-d$_6$) δ ppm: 9.50 (br. s., 1 H), 8.34 (m, J=8.56 Hz, 2 H), 8.08 (m, J=8.56 Hz, 2 H), 3.34 (br. s., 4 H), 2.86 (s, 6 H), 2.76 (s, 3 H), Example 100

N-(ppyridin-3-yl)-4-(5-(trifluoromethyl)-1,2,4-oxadiazol-3-yl)benzenesulfonamide

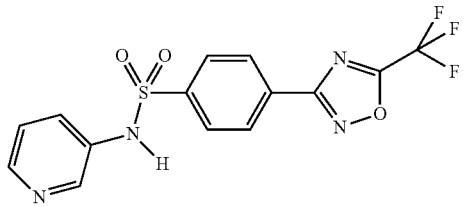 [SMILES: O=S(=O)(Nc1cccnc1)c1ccc(-c2noc(C(F)(F)F)n2)cc1]

$Rt_{UPLC}$=0.99 min, ESIMS [M+H]$^+$=371, white solid
$^1$H NMR (400 MHz, DMSO-d$_6$) δ ppm: 10.76 (s, 1 H), 8.24-8.28 (m, 4 H), 7.98 (d, J=8.31 Hz, 2 H), 7.51 (d, J=8.31 Hz, 1 H), 7.30 (d, J=12.72 Hz, 1 H).

Example 101

N-(cyclohexylmethyl)-4-(5-(trifluoromethyl)-1,2,4-oxadiazol-3-yl)benzenesulfonamide

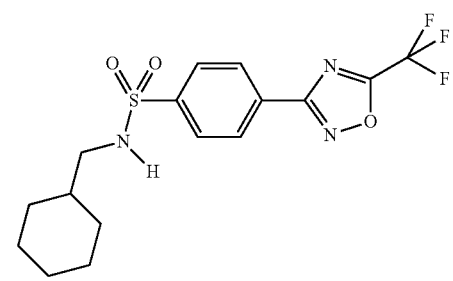 [SMILES: O=S(=O)(NCC1CCCCC1)c1ccc(-c2noc(C(F)(F)F)n2)cc1]

Rt$_{UPLC}$=1.32 min, ESIMS [M+H]$^-$=388, white solid
$^1$H NMR (400 MHz, DMSO-d$_6$) δ ppm: 8.28 (m, J=8.56 Hz, 2 H), 8.01 (m, J=8.80 Hz, 2 H), 2.63 (d, J=6.85 Hz, 2 H), 1.58-1.64 (m, 5 H), 1.32 (br. s., 1 H), 1.07-1.12 m, 2 H), 0.78-0.83 (m, 2 H).

Example 102

(R)—N-(pyrrolidin-3-yl)-4-(5-(trifluoromethyl)-1,2,4-oxadiazol-3-yl)benzenesulfonamide

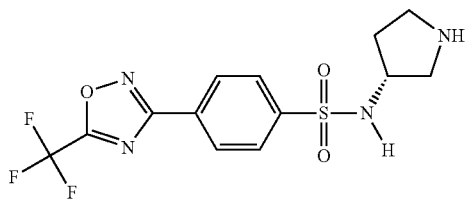 [SMILES: O=S(=O)(N[C@@H]1CCNC1)c1ccc(-c2noc(C(F)(F)F)n2)cc1]

(R)—N-(pyrrolidin-3-yl)-4-(5-(trifluoromethyl)-1,2,4-oxadiazol-3-yl)benzenesulfonamide was synthesized as (R)-3-[4-(5-trifluoromethyl-[1,2,4]oxadiazol-3-yl)-benzenesulfonylamino]-pyrrolidine-1-carboxylic acid tert-butyl ester and the Boc protecting group removed as follows: (277 mg, 0.612 mmol) of the crude coupling product was dissolved in HCl in Dioxane (1531 μL, 6.12 mmol) and stirred for 12 hr. It was concentrated to dryness to receive a brown solid. The crude product was subjected to purification by reverse phase prep-HPLC (gradient elution, water/MeCN both containing 0.1% TFA). Fractions containing the desired compound were combined and freeze-dried. The resulting mixture was dissolved in a mix of AcCN/water. They were load in a PL-HCO3 MP cartridge (from StratoSpheres™ SPE) and eluted with ACN. The eluate was freeze-dried to yield the final compound.

Rt$_{UPLC}$=1.19 min, ESIMS [M+H]$^+$=363, white solid
$^1$H NMR (400 MHz, DMSO-d$_6$) δ ppm: 8.29 (d, J=8.56 Hz, 2 H), 8.03-8.07 (m, 2 H), 3.74 (m, 0.3, rota), 3.56 (m, 0.7 H, rota), 3.27 (m, 1.5 H, rota), 3.15 (m, 0.3 H, rota), 2.96 (m, 0.2 H, rota), 2.76 (s, 1 H), 2.68 (m, 1 H), 2.38 (m, 0.8 H, rota), 2.33 (m, 0.2 H, rota), 1.90 (m, 0.3 H, rota), 1.73 (s, 1 H), 1.36 (m, 0.7 H, rota).

Example 103

N-o-tolyl-4-(5-trifluoromethyl-[1,2,4]oxadiazol-3-yl)-benzenesulfonamide

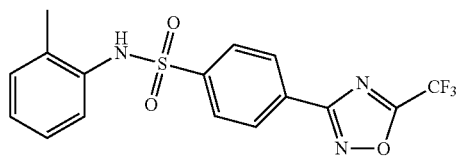 [SMILES: Cc1ccccc1NS(=O)(=O)c1ccc(-c2noc(C(F)(F)F)n2)cc1]

To a solution of N-hydroxy-4-o-tolylsulfamoyl-benzamidine (171 mg, 0.56 mmol) in pyridine (3 mL), TFAA (0.79 mL, 5.6 mmol) was added slowly (strong exothermic reaction!). The clear yellow solution was stirred and heated at 75° C. for 18 hrs. Subsequently the reaction mixture was cooled to room temperature. Water and dichloromethane were added and the mixture acidified with 6 M hydrochloric acid. The aqueous layer was separated and re-extracted twice with dichloromethane. The combined organic layers were dried with sodium sulfate, filtered and the solvent evaporated under reduced pressure. The resulting brown oil was purified by flash chromatography (ISCO CombiFlash Rf, 12 g silicagel; A=dichloromethane, B=ethanol, A:B 100:0 to 95:5) to give N-o-tolyl-4-(5-trifluoromethyl-[1,2,4]oxadiazol-3-yl)-benzenesulfonamide (213 mg, 0.54 mmol; 96% yield) as beige solid.

Rt$_{UPLC}$=7.950 min, ESIMS [M–1]+=382;
1H NMR (400 MHz, DMSO-d$_6$) δ ppm 9.86 (s, 1 H), 8.17-8.32 (m, 2 H), 7.78-7.92 (m, 2 H), 7.03-7.23 (m, 3 H), 6.95 (m, 1 H), 1.99 (s, 3 H).

Intermediate 103a:
4-cyano-N-o-tolyl-benzenesulfonamide

O-toluidine (Fluka; 0.118 mL, 1.1 mmol) was added to a clear light yellow solution of 4-cyano-benzenesulfonyl chloride (ABCR GmbH & Co. KG; 202 mg, 1 mmol) in pyridine (5 mL). The resulting clear red-brown solution was then stirred at room temperature for 18 hrs. Subsequently the reaction mixture was diluted with water (50 mL) and ethyl acetate (50 mL). The liquid layers were separated and the aqueous fraction was re-extracted twice with ethyl acetate (25 mL). The combined organic layers were washed with 0.1 M hydrochloric acid and brine (50 mL each), dried with sodium sulfate, filtered and evaporated under reduced pressure. The residue was dried under high vacuum to give 4-cyano-N-o-tolyl-benzenesulfonamide (314 mg, 0.92 mmol, 92% yield) as pale brown oil.

Rt$_{UPLC}$=0.96 min, ESIMS [M–1]+=271;
1H NMR (400 MHz, DMSO-d$_6$) δ ppm 9.93 (br. s., 1 H), 7.95-8.15 (m, 2 H), 7.75-7.86 (m, 2 H), 7.39 (m, 1 H), 7.03-7.24 (m, 2 H) 6.82-6.99 (m, 1 H), 1.98 (s, 2 H).

Intermediate 103b:
N-hydroxy-4-o-tolylsulfamoyl-benzamidine

To a solution of 4-cyano-N-o-tolyl-benzenesulfonamide (214 mg, 0.629 mmol) in ethanol (3 mL), hydroxylamine hydrochloride (437 mg, 6.29 mmol) and sodium hydrogen carbonate (528 mg, 6.29 mmol) were added and the resulting suspension was stirred at 60° C. for 18 hrs. Subsequently the reaction mixture was filtered. The precipitate was washed with ethanol and the combined eluents were evaporated under reduced pressure. The residue was dried under high vacuum (45° C., 3 hrs) to give N-hydroxy-4-o-tolylsulfamoyl-benzamidine (345 mg, 0.56 mmol, 89% crude yield, purity 49.6%) as beige solid.

Rt$_{UPLC}$=1.879 min, ESIMS [M+1]+=306.1
The following Examples 104-116 were made using a method analogous to that described above for Example 103.

Example 104

N-(2-chlorophenyl)-4-(5-(trifluoromethyl)-1,2,4-oxadiazol-3-yl)benzenesulfonamide

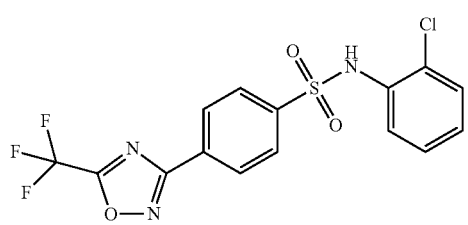

Rt$_{UPLC}$=7.977 min; ESIMS [M−1]+=402; beige solid;
1H NMR (400 MHz, DMSO-d$_6$) δ ppm 10.32 (s, 1 H), 8.19-8.31 (m, 2 H), 7.91 (m, J=8.53 Hz, 2 H), 7.41 (dd, J=7.84, 1.44 Hz, 1 H), 7.17-7.36 (m, 3 H).

Example 105

N-m-tolyl-4-(5-(trifluoromethyl)-1,2,4-oxadiazol-3-yl)benzenesulfonamide

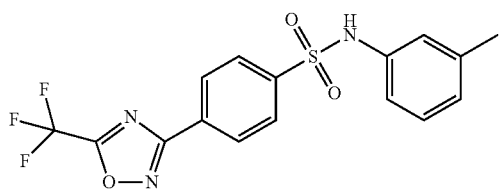 [SMILES: Cc1cccc(NS(=O)(=O)c2ccc(-c3noc(C(F)(F)F)n3)cc2)c1]

Rt$_{UPLC}$=7.983 min; ESIMS [M−1]+=382; beige solid;
1H NMR (400 MHz, DMSO-d$_6$) δ ppm 10.43 (s, 1 H), 8.24-8.22 (m, J=8.16 Hz, 2 H), 7.98-7.96 (m, J=8.28 Hz, 2 H), 7.14 (m, 1 H), 6.71-6.98 (m, 3 H), 2.19 (s, 3H).

Example 106

N-(3-fluorophenyl)-4-(5-(trifluoromethyl)-1,2,4-oxadiazol-3-yl)benzenesulfonamide

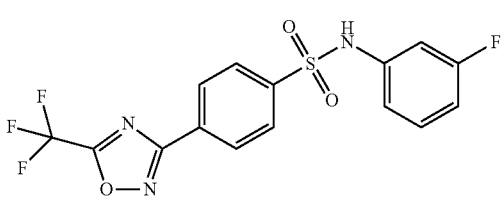 [SMILES: O=S(=O)(Nc1cccc(F)c1)c1ccc(-c2noc(C(F)(F)F)n2)cc1]

Rt$_{UPLC}$=7.833 min; ESIMS [M−1]+=386; white solid;
1H NMR (400 MHz, DMSO-d$_6$) δ ppm 10.80 (s, 1 H), 8.27-8.25 (m, J=8.16 Hz, 2 H) 8.01-7.99 (m, J=8.28 Hz, 2 H) 7.28 (d, J=8.16 Hz, 1H), 6.77-6.99 (m, 3 H).

Example 107

N-(3-chlorophenyl)-4-(5-(trifluoromethyl)-1,2,4-oxadiazol-3-yl)benzenesulfonamide

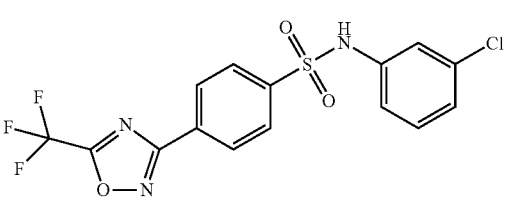 [SMILES: O=S(=O)(Nc1cccc(Cl)c1)c1ccc(-c2noc(C(F)(F)F)n2)cc1]

Rt$_{UPLC}$=8.153 min; ESIMS [M−1]+=402; white solid;
1H NMR (400 MHz, DMSO-d$_6$) δ ppm 10.80 (s, 1 H), 8.25-8.27 (m, J=8.41 Hz, 2 H), 8.01-7.99 (m, J=8.41 Hz, 2 H) 7.30 (m, 1 H), 6.99-7.19 (m, 3 H).

Example 108

N-p-tolyl-4-(5-(trifluoromethyl)-1,2,4-oxadiazol-3-yl)benzenesulfonamide

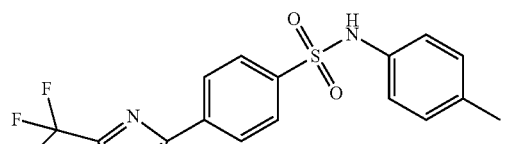

Rt$_{MS5}$=7.369 min; ESIMS [M−1]+=382; white solid;
1H NMR (400 MHz, DMSO-d$_6$) δ ppm 10.31 (s, 1 H), 8.15-8.30 (m, 2 H), 7.86-7.97 (m, 2 H), 7.00-7.09 (m, 2 H), 6.90-7.00 (m, 2 H), 2.18 (s, 3 H).

Example 109

N-(4-fluorophenyl)-4-(5-(trifluoromethyl)-1,2,4-oxadiazol-3-yl)benzenesulfonamide

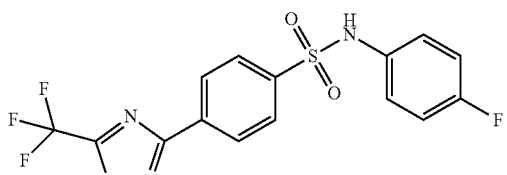

Rt$_{MS5}$=7.150 min; ESIMS [M−1]+=386; white solid;
1H NMR (400 MHz, DMSO-d$_6$) δ ppm 10.44 (s, 1 H), 8.15-8.31 (m, 2 H), 7.83-7.99 (m, 2 H), 6.99-7.18 (m, 4 H).

Example 110

N-(4-chlorophenyl)-4-(5-(trifluoromethyl)-1,2,4-oxadiazol-3-yl)benzenesulfonamide

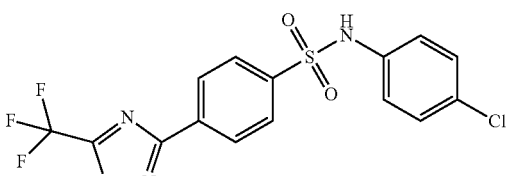

Rt$_{MS5}$=7.552 min; ESIMS [M−1]+=402; white solid;
1H NMR (400 MHz, DMSO-d$_6$) δ ppm 10.64 (br. s., 1 H), 8.23-8.25 (m, J=8.16 Hz, 2 H), 7.95-7.97 (m, J=8.16 Hz, 2 H) 7.31-7.33 (m, J=8.28 Hz, 2 H) 7.10-7.12 (m, J=8.41 Hz, 2 H).

Example 111

N-(2-fluorophenyl)-4-(5-(trifluoromethyl)-1,2,4-oxadiazol-3-yl)benzenesulfonamide

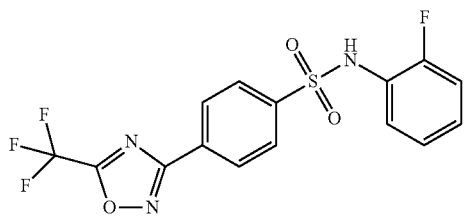 [SMILES: O=S(=O)(Nc1ccccc1F)c1ccc(-c2noc(C(F)(F)F)n2)cc1]

Rt$_{MS5}$=7.328 min; ESIMS [M−1]+=386; white solid; 1H NMR (400 MHz, DMSO-d$_6$) δ ppm 10.42 (s, 1 H), 8.25 (d, J=6.90 Hz, 2 H), 7.93 (d, J=8.16 Hz, 2 H), 7.25 (s, 2 H), 7.16 (s, 2 H).

Example 112

N-(3-(dimethylamino)propyl)-N-methyl-4-(5-(trifluoromethyl)-1,2,4-oxadiazol-3-yl)benzenesulfonamide

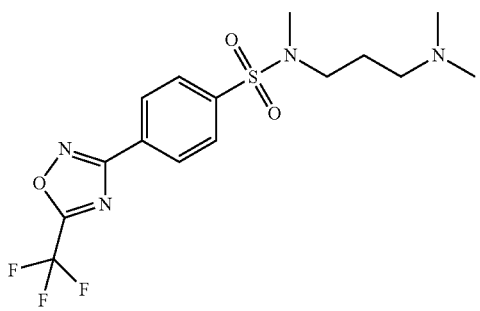 [SMILES: CN(C)CCCN(C)S(=O)(=O)c1ccc(-c2noc(C(F)(F)F)n2)cc1]

Rt$_{MS5}$=4.507 min; ESIMS [M+1]+=393; pale brown resin; 1H NMR (400 MHz, DMSO-d$_6$) δ ppm 9.37 (m, 1 H), 8.22-8.43 (m, 2 H), 7.90-8.14 (m, 2 H), 3.08 (q, J=6.61 Hz, 4 H), 2.80 (d, J=4.52 Hz, 6 H), 2.74 (s, 3 H), 1.77-2.01 (m, 2 H).

Example 113

N-(3-(dimethylamino)propyl)-4-(5-(trifluoromethyl)-1,2,4-oxadiazol-3-yl)benzenesulfonamide (TFA-salt)

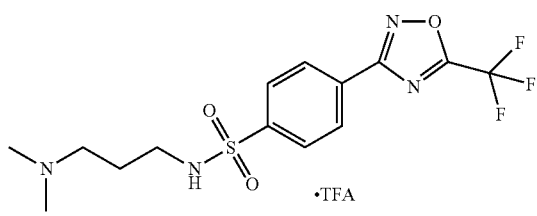 [SMILES: CN(C)CCCNS(=O)(=O)c1ccc(-c2noc(C(F)(F)F)n2)cc1]

Rt$_{MS5}$=4.330 min; ESIMS [M+1]+=379; pale brown resin; 1H NMR (400 MHz, DMSO-d$_6$) δ ppm 9.39 (m, 1 H), 8.26-8.36 (m, 2 H), 7.98-8.08 (m, 3 H), 2.99-3.12 (m, 2 H), 2.85 (q, J=6.61 Hz, 2 H), 2.74 (d, J=4.64 Hz, 6 H), 1.67-1.84 (m, 2 H).

Example 114

N,N-dimethyl-4-(5-(trifluoromethyl)-1,2,4-oxadiazol-3-yl)benzenesulfonamide

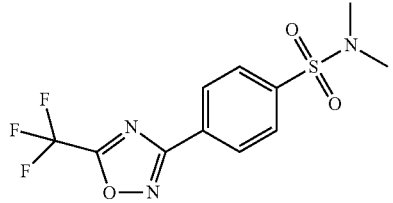 [SMILES: CN(C)S(=O)(=O)c1ccc(-c2noc(C(F)(F)F)n2)cc1]

Rt$_{MS5}$=6.640 min; ESIMS [M−1]+=322; brown resin; 1H NMR (400 MHz, DMSO-d$_6$) δ ppm 8.22-8.40 (m, 2 H), 7.87-8.09 (m, 2 H), 2.67 (s, 6 H).

Example 115

N-((1-methylpyrrolidin-3-yl)methyl)-4-(5-(trifluoromethyl)-1,2,4-oxadiazol-3-yl)benzenesulfonamide

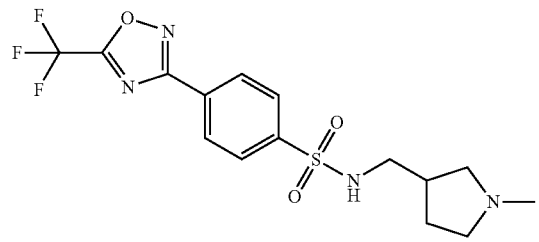 [SMILES: CN1CCC(CNS(=O)(=O)c2ccc(-c3noc(C(F)(F)F)n3)cc2)C1]

Rt$_{MS5}$=4.362 min; ESIMS [M+1]+=391; pale brown resin; 1H NMR (400 MHz, DMSO-d$_6$) δ ppm 9.81 (br. s., 1 H), 8.26-8.36 (m, 2 H), 8.14 (q, J=6.27 Hz, 1 H), 8.02 (dd, J=8.47, 1.69 Hz, 2 H), 3.64 (m, 1 H), 3.40 (m, 1 H), 3.07 (m, 1 H), 2.77-2.94 (m, 4 H), 2.69 (d, J=10.04 Hz, 1 H), 2.41 (d, J=7.15 Hz, 1 H).

Example 116

N-(3-hydroxypropyl)-4-(5-(trifluoromethyl)-1,2,4-oxadiazol-3-yl)benzenesulfonamide

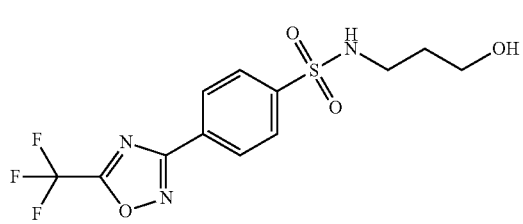 [SMILES: O=S(=O)(NCCCO)c1ccc(-c2noc(C(F)(F)F)n2)cc1]

Rt$_{MS5}$=5.697 min; ESIMS [M+1]+=352; white solid; 1H NMR (400 MHz, DMSO-d$_6$) δ ppm 8.21-8.37 (m, 2 H), 7.94-8.10 (m, 2 H), 7.81 (m, 1 H), 4.44 (t, J=5.02 Hz, 1 H), 3.22-3.44 (m, 2 H), 2.72-2.95 (m, 2 H), 1.38-1.63 (m, 2 H).

Examples 117-123

General method of amide bond formation with COMU

Examples 117-118 and 120 to 122 were prepared using a procedure analogous to that described in Example 88, whereas Examples 119 and 123 were prepared using a procedure analogous to that described in Example 3 except that the final coupling step was performed with COMU. The exact equivalents of amine, coupling reagent and base are indicated for each example.

Example 117

(S)—N-(1-(dimethylamino)-3-phenylpropan-2-yl)-2-fluoro-4-(5-(trifluoromethyl)-1,2,4-oxadiazol-3-yl)benzamide

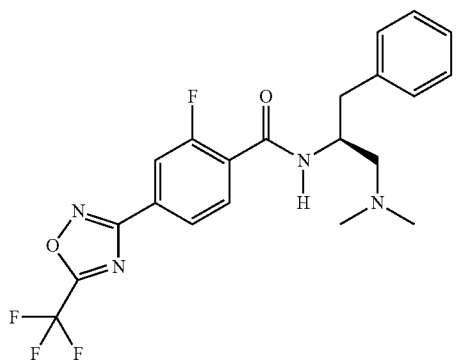 [SMILES: CN(C)C[C@H](Cc1ccccc1)NC(=O)c1ccc(-c2noc(C(F)(F)F)n2)cc1F]

Amine 1.05 eq, COMU 1 eq, DIPEA 2 eq.
$Rt_{MS4}$=3.87 min; [M+H]+=437.2; pink solid.
1H NMR (400 MHz, DMSO-$d_6$) δ ppm 8.37 (m, 1 H), 7.86-7.97 (m, 2 H), 7.63 (m, 1 H), 7.16-7.33 (m, 5 H), 4.30 (m, 1 H), 2.95 (m, 1 H), 2.74 (m, 1 H), 2.27-2.43 (m, 2 H), 2.21 (s, 6 H).

Example 118

(R)—N-(1-(dimethylamino)-3-phenylpropan-2-yl)-2-fluoro-4-(5-(trifluoromethyl)-1,2,4-oxadiazol-3-yl)benzamide

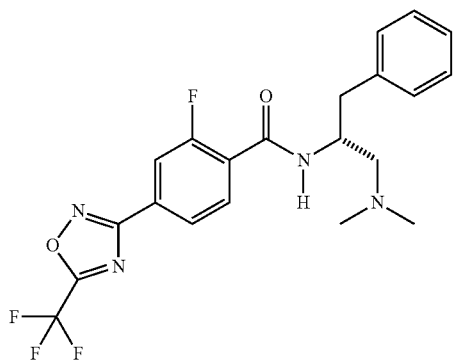 [SMILES: CN(C)C[C@@H](Cc1ccccc1)NC(=O)c1ccc(-c2noc(C(F)(F)F)n2)cc1F]

Amine 1.05 eq, COMU 1 eq, DIPEA 2 eq.
$Rt_{MS4}$=3.86 min., [M+H]+=437.2 as pink solid.
1H NMR (400 MHz, DMSO-$d_6$) δ ppm 8.37 (m, 1 H), 7.86-7.98 (m, 2 H), 7.63 (m, 1 H), 7.16-7.32 (m, 5 H), 4.28 (m, 1 H), 2.96 (m, 1 H), 2.73 (m, 1 H), 2.28-2.43 (m, 2 H), 2.21 (s, 6 H).

Example 119

N-(1-(dimethylamino)-2-methylpropan-2-yl)-4-(5-(trifluoromethyl)-1,2,4-oxadiazol-3-yl)benzamide

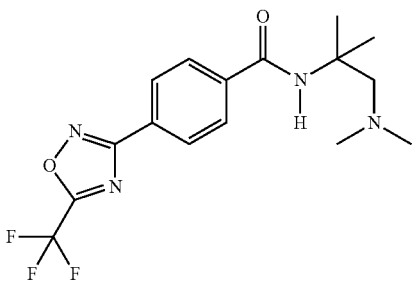 [SMILES: CN(C)CC(C)(C)NC(=O)c1ccc(-c2noc(C(F)(F)F)n2)cc1]

Amine 1.05 eq, COMU 1.25 eq, DIPEA 2 eq.
$Rt_{MS4}$=3.24 min., [M+H]+=357.3 as yellow solid.
1H NMR (400 MHz, DMSO-$d_6$) δ ppm 8.10-8.15 (m, 2 H), 7.99 (d, J=8.56 Hz, 2 H), 7.85 (s, 1 H), 2.63 (s, 2 H), 2.25 (s, 6 H), 1.36 (s, 6 H).

Example 120

N-(1-(dimethylamino)-2-methylpropan-2-yl)-2-fluoro-4-(5-(trifluoromethyl)-1,2,4-oxadiazol-3-yl)benzamide

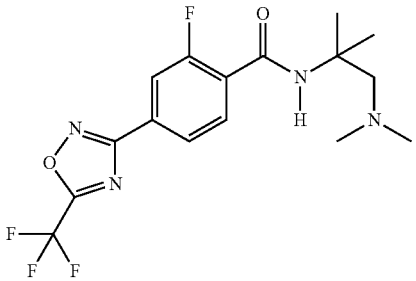 [SMILES: CN(C)CC(C)(C)NC(=O)c1ccc(-c2noc(C(F)(F)F)n2)cc1F]

Amine 1.05 eq, COMU 1.25 eq, DIPEA 2 eq.
$Rt_{MS4}$=3.24 min., [M+H]+=357.3 as yellow solid.
1H NMR (400 MHz, DMSO-$d_6$) δ ppm 8.01 (m, 1 H), 7.96 (m, 1 H), 7.89 (m, 1 H), 7.76 (m, 1 H), 2.59 (s, 2 H), 2.29 (s, 6 H), 1.34 (s, 6H).

Example 121

N-(1-(diethylamino)propan-2-yl)-2-fluoro-4-(5-(trifluoromethyl)-1,2,4-oxadiazol-3-yl)benzamide

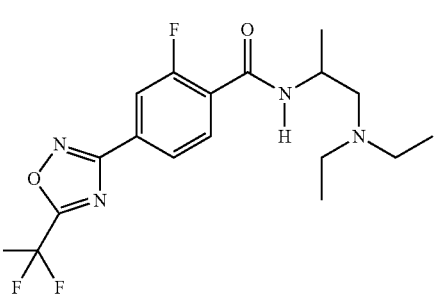

Amine 1.05 eq, COMU 1.25 eq, DIPEA 2 eq.

Rt$_{MS4}$=3.26 min., [M+H]+=388.36 as yellow solid.

1H NMR (400 MHz, DMSO-d$_6$) δ ppm 8.24 (m, 1H), 7.95-8.00 (m, 1 H), 7.92 (m, 1 H), 7.80 (m, 1 H), 4.06 (m, 1 H), 2.35 (m, 1 H), 1.16 (d, J=6.60 Hz, 3 H), 0.97 (t, J=7.09 Hz, 6 H), 1proton [(CH$_3$)CH—CH$_2$—N—(CH$_2$CH$_3$)$_2$] is under DMSO solvent peak.

Example 122

N-(2-(dimethylamino)propyl)-2-fluoro-4-(5-(trifluoromethyl)-1,2,4-oxadiazol-3-yl)benzamide

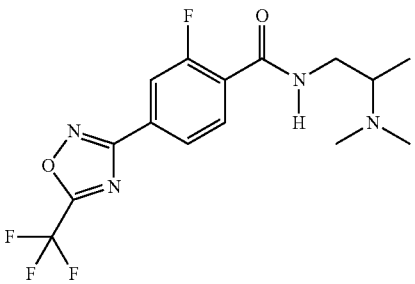 [SMILES: CC(CNC(=O)c1ccc(-c2noc(C(F)(F)F)n2)cc1F)N(C)C]

Amine 1.5 eq, COMU 1.3 eq, DIPEA 2 eq.

Rt$_{MS4}$=3.10 min., [M+H]+=361.3 as yellow oil.

1H NMR (400 MHz, DMSO-d$_6$) δ ppm 8.35 (m, 1 H) 7.90-8.01 (m, 2 H) 7.85 (m, 1 H) 3.25 (m, 2 H) 2.74 (m, 1 H) 2.20 (s, 6 H) 0.94 (d, J=6.60 Hz, 3 H).

Example 123

N-(1-(diethylamino)propan-2-yl)-4-(5-(trifluoromethyl)-1,2,4-oxadiazol-3-yl)benzamide

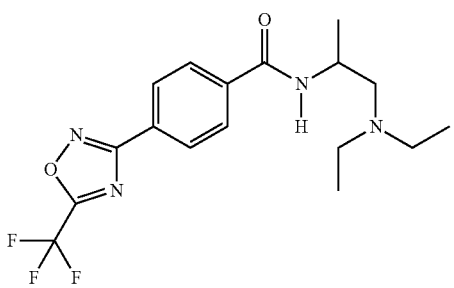 [SMILES: CCN(CC)CC(C)NC(=O)c1ccc(-c2noc(C(F)(F)F)n2)cc1]

Amine 2 eq, COMU 1.2 eq, DIPEA 3 eq.

Rt$_{MS4}$=3.37 min., [M+H]+=370.0 as white solid.

1H NMR (400 MHz, DMSO-d$_6$) δ ppm 8.30-8.39 (m, 1 H) 8.16 (d, J=8.31 Hz, 2 H) 8.01-8.09 (m, 2 H) 4.05-4.19 (m, 1 H) 1.17 (d, J=6.60 Hz, 3 H) 0.96 (t, J=7.09 Hz, 6 H).

Examples 124-156

General method for amide bond formation with EDC (HOBT DIPEA)

To a solution of the appropriate acid (150 mg, 0.510 mmol) in THF (1.700 ml) was added EDC.HCl (147 mg, 0.765 mmol), HOBT (102 mg, 0.663 mmol), the appropriate amine (1.1 eq, 0.561 mmol) and DIPEA (0.267 ml, 1.530 mmol). The resulting solution was stirred at 75° C. After 3 hrs the reaction mixture was poured in water and basified with aqueous sat. NaHCO$_3$ solution and extracted with ethyl acetate (4×30 ml). The combined organic layers were washed with brine, dried over MgSO$_4$, filtered and evaporated. The crude product was either subjected to purification by reverse phase prep-H PLC (gradient elution, water/ACN both containing 0.1% TFA) [Method A] or purified via normal phase liquid chromatography using prepacked Redisept Si=2 columns and either EtOAc and Heptane as eluent [Method B] or DCM EtOAc [Method C]. Fractions containing the desired compound were combined and freeze-dried or the organic solvent removed on HV.

The following examples have been prepared according to the above method. The exact equivalents of amine, coupling reagent and base are indicated for each example individually if different to the standard procedure (1.1 eq amine, 1.5 eq EDC.HCl, 1.3 eq HOBT, 3 eq DIPEA).

Example 124

(R)—N-(1-(dimethylamino)propan-2-yl)-2,6-difluoro-4-(5-(trifluoromethyl)-1,2,4-oxadiazol-3-yl)benzamide

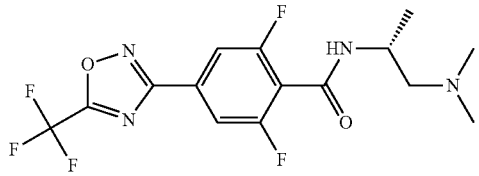 [SMILES: C[C@H](CN(C)C)NC(=O)c1c(F)cc(-c2noc(C(F)(F)F)n2)cc1F]

Rt$_{MS1}$=1.45 min., [M+H]+=378.00 as white solid.

1H NMR (400 MHz, MeOH-d$_4$) δ ppm 7.81 (d, J=7.34 Hz, 2 H), 4.28 (m, 1 H), 2.50 (d, J=7.34 Hz, 1 H), 2.41 (d, J=6.36 Hz, 1 H), 2.32 (s, 6 H), 1.28 (d, J=6.60 Hz, 3 H).

The acid intermediate used in the synthesis of Example 124 was prepared as described below.

Intermediate 124a: 4-cyano-2,6-difluorobenzoic acid

To a solution of 3,5-difluorobenzonitrile (3.48 g, 25 mmol, Fluorochem) in THF (35 ml) was added slowly butyl lithium (1.6M in hexanes) (15.63 ml, 25.00 mmol) at −75° C. The resulting solution was stirred for 1 hr at −70-75° C. Then this solution was poured on freshly crushed dry ice CO2 (44.0 g, 1000 mmol). The contents were stirred at room temperature until dry ice disappearance. The solvent was evaporated off under HV. Then residual organic layer was suspended in water and extracted with ethyl acetate (3×50 ml). The product containing aqueous layer was acidified with aqueous HCl solution and the product was re-extracted in the organic layer with Ethylacetate (4×50 ml). The combined organic layers were washed with brine, dried over MgSO$_4$, filtered and evaporated to give a white crystalline solid (2.5731 g, 13.91 mmol, 55.6% yield)

1H NMR (400 MHz, DMSO-d$_6$) δ ppm 14.32 (br. S., 1 H), 7.78-8.01 (m, 2 H).

The product was used in the next step without further purification.

Intermediate 124b: 2,6-difluoro-4-(N'-hydroxycarbamimidoyl)benzoic acid

To a solution of intermediate 124a (2.5731 g, 14.05 mmol) in EtOH (23.42 mL) was added hydroxylamine hydrochloride (2.051 g, 29.5 mmol) dissolved in water and aqueous K$_2$CO$_3$ (3.11 g, 22.48 mmol). 8-Hydroxyquinone (0.027 g, 0.183 mmol) was added. The resulting solution was stirred at reflux for 4 hrs before EtOH was removed under HV. The aqueous layer was acidified with aqueous HCl (2M) solution and extracted with ethyl acetate (3×100 ml). The combined organic layers were washed with brine, dried over MgSO$_4$, filtered and evaporated to give intermediate 118b (326.8 mg, 1.436 mmol, 10.22% yield) as off white solid. The product was used without any further purification.

1H NMR (400 MHz, DMSO-d$_6$) δ ppm 13.87 (br. S., 1 H) 10.10 (s, 1 H) 7.47 (d, J=9.54 Hz, 2 H) 6.06 (br. S., 2H).

Intermediate 124c: 2,6-difluoro-4-(5-(trifluoromethyl)-1,2,4-oxadiazol-3-yl)benzoic acid To a vigorously stirred suspension of intermediate 124b (326.8 mg, 1.512 mmol) in THF (5.040 ml) was added drop wise trifluoroacetic anhydride (0.320 ml, 2.268 mmol) over 5 min. The resulting solution was stirred at room temperature for 3 hrs. The reaction mixture was evaporated to obtain intermediate 124c (410.5 mg, 1.326 mmol, 88% yield) as pink solid.

1H NMR (400 MHz, DMSO-d$_6$) δ ppm 14.32 (br. S., 1 H), 7.91-7.85 (m, 2 H).

Example 125

(R)-2-chloro-N-(1-(dimethylamino)propan-2-yl)-4-(5-(trifluoromethyl)-1,2,4-oxadiazol-3-yl)benzamide

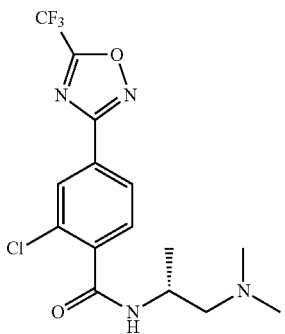 [SMILES: C[C@H](CN(C)C)NC(=O)c1ccc(-c2noc(C(F)(F)F)n2)cc1Cl]

[Method C]

Rt$_{MS1}$=1.50 min., [M+H]+=376.00 as light orange solid.

1H NMR (400 MHz, MeOH-d$_4$) δ ppm 8.20 (d, J=1.47 Hz, 1 H), 8.13 (s, 1 H) 7.73 (d, J=8.07 Hz, 1 H), 4.31 (m, 1 H), 2.54 (m, 1 H), 2.34 (s, 7 H), 1.28 (d, J=6.60 Hz, 3 H).

The acid intermediate used in the synthesis of Example 125 was prepared as described below.

Intermediate 125a: methyl 4-amino-2-chlorobenzoate

To a solution of 4-amino-2-chlorobenzoic acid (2 g, 11.66 mmol) in MeOH (55.5 mL) was added thionyl chloride (3.40 mL, 46.6 mmol) dropwise at 0° C. The resulting solution was stirred at rt. After 32 h the solvent was removed. The crude product was taken up in EtOAc and washed with sat. aqueous NaHCO$_3$ and brine. The organic layer was dried over MgSO$_4$, filtered and evaporated to dryness to give intermediate 125a (2.146 g, 11.45 mmol, 98% yield) as white solid.

1H NMR (400 MHz, DMSO-d$_6$) δ ppm 7.64 (d, J=8.56 Hz, 1 H), 6.64 (d, J=2.20 Hz, 1 H), 6.51 (dd, J=8.80, 2.20 Hz, 1 H), 6.16 (bs, 2 H), 3.73 (s, 3 H).

Intermediate 125b: methyl 2-chloro-4-cyanobenzoate

Intermediate 125a (2.146 g, 11.56 mmol) was dispersed in water (8 mL) and HCl (12 ml, 96 mmol) and the mixture was cooled to 0° C. An aqueous solution of sodium nitrite (0.885 g, 12.83 mmol) was added dropwise in such a manner that the temperature never exceeded 5° C. The resulting solution was stirred at 0-5° C. for 45 min. and neutralized by addition of solid NaHCO$_3$. The diazonium salt was added to an aqueous solution of copper (I) cyanide (1.294 g, 14.45 mmol) and sodium cyanide (1.383 g, 28.2 mmol) in water (25 mL) at 75° C. The contents were stirred for 1.5 hr at 75-80° C. After cooling the reaction mixture to rt, the product was extracted with toluene (4×100 ml). The combined organic layers were washed with brine, dried over MgSO$_4$, filtered and the solvent was removed in vacuum. The crude product was purified by flash chromatography with Isco Combiflash: 80 g Redisep column, eluent Heptane/Ethyl acetate (A/B), detection at 254 nm. Mobile phase: 5 min. (0% B), from 0 to 20% B for 10 min. then 20% B for 10 min. The priduct containing fractions were combined and evaporated to dryness to yield intermediate 125b (939 mg, 4.76 mmol, 41.1% yield) as orange solid.

1H NMR (400 MHz, DMSO-d$_6$) δ ppm 8.23 (s, 1 H), 7.96 (bs, 2 H), 3.91 (s, 3 H).

Rt$_{MS1}$=1.80 min., [M+H]+=196.1

Intermediate 125c: 2-chloro-4-cyanobenzoic acid

Intermediate 125b was dissolved in a 0.5 molar 1:1 mixture of MeOH/THF and LiOH.H$_2$O (302 mg, 7.21 mmol. The reaction was stirred for 5 hrs before the solvent was removes under vaccuum. The residue was suspended in water and acidified with aqueous HCl (2M). A pink precipitate was filtered off and dried under HV+cold trap to yield intermediate 125c (569.2 mg, 3.04 mmol, 63.3% yield) as pinkish solid.

1H NMR (400 MHz, DMSO-d$_6$) δ ppm 13.95 (br. S., 1 H), 8.18 (s, 1H), 7.85-7.96 (m, 2 H).

Rt$_{MS1}$=1.21 min., [M+H]$^+$=182.1.

Intermediate 125d: (E)-2-chloro-4-(N'-hydroxycarbamimidoyl)benzoic acid

Hydroxylamine hydrochloride (457 mg, 6.58 mmol) was dissolved in 5.2 ml Water before K$_2$CO$_3$ (693 mg, 5.02 mmol) was added. This solution was added to a stirred solution of intermediate 3 (569.2 mg, 3.13 mmol) in EtOH (5225 µL). Then 8-Hydroxyquinone (5.92 mg, 0.041 mmol) was added. The resulting mixture was allowed to reflux for 4 hrs before the EtOH was evaporated off. The aqueous layer was acidified and extracted with ethyl acetate. The combined organic layers were washed with brine, dried over MgSO$_4$, filtered and evaporated to yield intermediate 129d (276.9 mg, 1.161 mmol, 37.0% yield) as orange solid. The product was used without further purification in the next step.

1H NMR (400 MHz, DMSO-d$_6$) δ ppm 13.41 (br. S., 1 H), 9.98 (s, 1 H), 7.77-7.83 (m, 2 H), 7.73 (d, 1 H) 6.01 (br. S., 2 H).

Intermediate 125e: 2-chloro-4-(5-(trifluoromethyl)-1,2,4-oxadiazol-3-yl)benzoic acid To a vigorously stirred suspension of intermediate 125d (276.9 mg, 1.290 mmol) in THF (4.301 ml) was added dropwise trifluoroacetic anhydride (0.273 ml, 1.935 mmol) over 5 min. The resulting solution was stirred at rt for 3 hr. The reaction mixture was evaporated to dryness to yield intermediate 125e (335.6 mg, 1.032 mmol, 80% yield) as light orange solid. The crude product was used without further purification in the coupling reaction.

Rt$_{MS1}$=2.23 min., no ionisation.

The acid intermediates used in the synthesis of Examples 126-156 below were prepared as described in Example 3 (unfluorinated benzoic acid intermediates) or Example 88 (fluorinated benzoic acid intermediates).

Example 126

(R)—N-(1-(diethylamino)propan-2-yl)-2-fluoro-4-(5-(trifluoromethyl)-1,2,4-oxadiazol-3-yl)benzamide

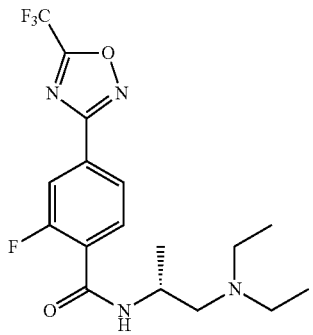

(1.1 eq amine, 1.5 eq EDC.HCl, 1.3 eq HOBT, 3 eq DIPEA). [Method C]

Rt$_{MS1}$=1.54 min., [M+H]+=388.0.00 as yellow oil.

NMR (400 MHz, MeOH-d$_4$) δ ppm 8.05 (m, 1 H), 7.88-7.99 (m, 2 H), 4.30 (m, 1 H), 2.75-2.69 (m, 5 H), 2.60 (m, 1 H), 1.30 (d, J=6.60 Hz, 3 H), 1.11 (t, J=7.21 Hz, 6 H).

Example 127

(S)—N-(1-(diethylamino)propan-2-yl)-2-fluoro-4-(5-(trifluoromethyl)-1,2,4-oxadiazol-3-yl)benzamide

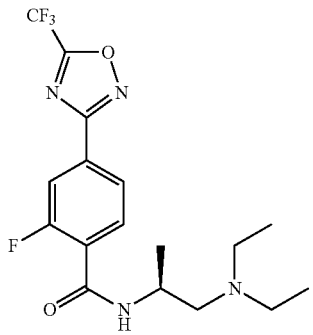 [SMILES: CCN(CC)C[C@H](C)NC(=O)c1ccc(-c2noc(C(F)(F)F)n2)cc1F]

(1.2 eq amine, 1.5 eq EDC.HCl, 1.3 eq HOBT, 3 eq DIPEA). [Method C]

Rt$_{MS1}$=1.55 min., [M+H]+=389.4 as yellow oil.

1H NMR (400 MHz, MeOH-d$_4$) δ ppm 8.05 (dd, J=8.07, 1.47 Hz, 1 H), 7.87-7.99 (m, 2 H), 4.26 (m, 1 H), 2.57-2.72 (m, 5 H), 2.54 (d, J=6.11 Hz, 1 H), 1.29 (d, J=6.60 Hz, 3 H), 1.08 (t, J=7.21 Hz, 6 H).

Example 128

(R)-2-fluoro-N-(1-(pyrrolidin-1-yl)propan-2-yl)-4-(5-(trifluoromethyl)-1,2,4-oxadiazol-3-yl)benzamide

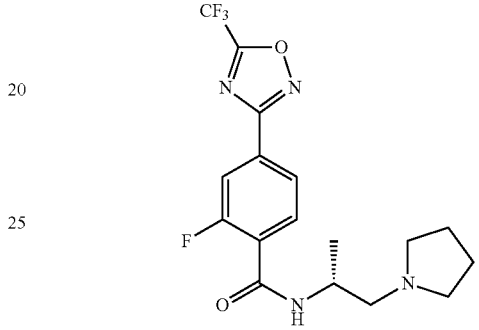

(1.2 eq amine, 1.5 eq EDC.HCl, 1.3 eq HOBT, 3 eq DIPEA). [Method C]

Rt$_{MS1}$=1.50 min., [M+H]+=387.3 as white solid.

1H NMR (400 MHz, MeOH-d$_4$) δ ppm 8.04 (d, J=8.07 Hz, 1 H), 7.85-7.99 (m, 2 H), 4.32 (m, 1 H), 2.51-2.80 (m, 6 H), 1.77-1.91 (m, 4 H), 1.30 (d, J=6.60 Hz, 3 H).

Example 129

(R)-2-fluoro-N-(1-(piperidin-1-yl)propan-2-yl)-4-(5-(trifluoromethyl)-1,2,4-oxadiazol-3-yl)benzamide

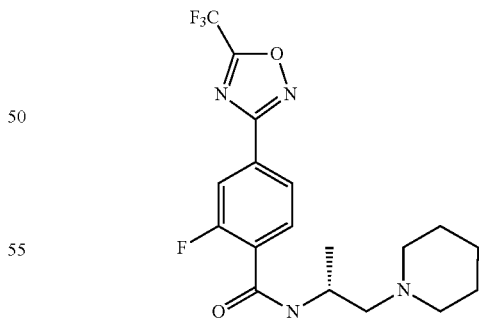

(1.2 eq amine, 1.5 eq EDC.HCl, 1.3 eq HOBT, 3 eq DIPEA). [Method C]

Rt$_{MS1}$=1.56 min., [M+H]+=401.3 as yellow thick oil.

1H NMR (400 MHz, MeOH-d$_4$) δ ppm 8.04 (d, J=1.47 Hz, 1 H), 7.87-7.99 (m, 2 H), 4.33 (m, 1 H), 2.35-2.63 (m, 6 H), 1.57-1.69 (m, 4 H), 1.43-1.54 (m, 2 H), 1.28 (d, J=6.60 Hz, 3 H).

Example 130

(R)—N-(1-(pyrrolidin-1-yl)propan-2-yl)-4-(5-(trifluoromethyl)-1,2,4-oxadiazol-3-yl)benzamide

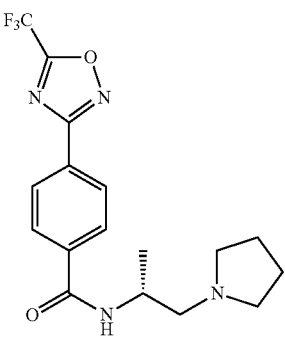 [SMILES: C[C@H](CN1CCCC1)NC(=O)c1ccc(-c2noc(C(F)(F)F)n2)cc1]

Amine: 1.2 eq, EDC: 1.3 eq HOBT: 1.15 DIPEA: 3 eq [Method C]

$Rt_{MS1}$=1.56 min., [M+H]+=369.3 as yellow thick oil.

1H NMR (400 MHz, MeOH-d$_4$) δ ppm 8.23 (d, J=8.31 Hz, 2 H), 8.05 (d, J=8.07 Hz, 2 H), 4.38 (m, 1 H), 2.81 (m, 1 H), 2.57-2.74 (m, 4 H), 2.53 (m, 1 H), 1.77-1.89 (m, 4 H), 1.29 (d, J=6.60 Hz, 3 H).

Example 131

(R)—N-(1-(piperidin-1-yl)propan-2-yl)-4-(5-(trifluoromethyl)-1,2,4-oxadiazol-3-yl)benzamide

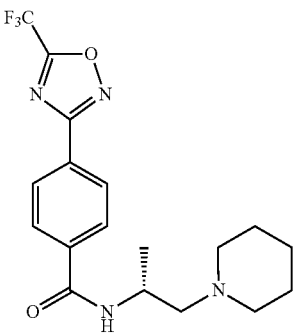 [SMILES: C[C@H](CN1CCCCC1)NC(=O)c1ccc(-c2noc(C(F)(F)F)n2)cc1]

Amine: 1.2 eq, EDC: 1.3 eq HOBT: 1.15 DIPEA: 3 eq [Method C]

$Rt_{MS1}$=1.57 min., [M+H]+=383.4 as yellow thick oil.

1H NMR (400 MHz, MeOH-d$_4$) δ ppm 8.23 (d, J=8.31 Hz, 2 H), 8.03 (d, J=8.31 Hz, 2 H), 4.38 (m, 1 H), 2.33-2.68 (m, 6 H), 1.55-1.68 (m, 4 H), 1.48 (m, J=5.62 Hz, 2 H), 1.27 (d, J=6.60 Hz, 3 H).

Example 132

(R)—N-(1-(diethylamino)propan-2-yl)-4-(5-(trifluoromethyl)-1,2,4-oxadiazol-3-yl)benzamide

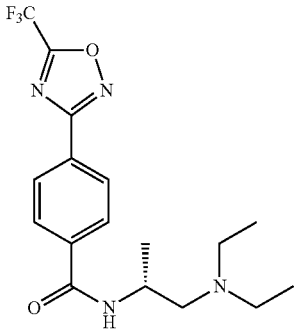

Amine: 1.2 eq, EDC: 1.3 eq HOBT: 1.15 DIPEA: 3 eq [Method C]

$Rt_{MS1}$=1.54 min., [M+H]+=371.0 as off white solid.

1H NMR (400 MHz, MeOH-d$_4$) δ ppm 8.23 (d, J=8.31 Hz, 2 H), 8.02 (d, J=8.31 Hz, 2 H), 4.30 (m, 1 H), 2.59-2.75 (m, 5 H), 2.48-2.59 (m, 1 H), 1.29 (d, J=6.60 Hz, 3 H), 1.08 (t, J=7.09 Hz, 6 H).

Example 133

(S)—N-(1-(diethylamino)propan-2-yl)-4-(5-(trifluoromethyl)-1,2,4-oxadiazol-3-yl)benzamide

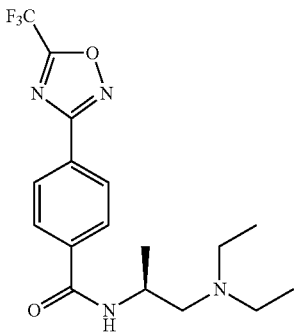 [SMILES: CCN(CC)C[C@H](C)NC(=O)c1ccc(-c2noc(C(F)(F)F)n2)cc1]

Amine: 1.2 eq, EDC: 1.3 eq HOBT: 1.15 DIPEA: 3 eq [Method C]

$Rt_{MS1}$=1.54 min., [M+H]+=371.3 as off white solid.

1H NMR (400 MHz, MeOH-d$_4$) δ ppm 8.21 (d, J=8.56 Hz, 2 H), 8.01 (d, J=8.31 Hz, 2 H), 4.30 (m, 1 H), 2.41-2.80 (m, 6 H), 1.29 (d, J=6.60 Hz, 3 H), 1.08 (t, J=7.21 Hz, 6 H).

Example 134

(R)—N-(1-(diethylamino)-3-methylbutan-2-yl)-4-(5-(trifluoromethyl)-1,2,4-oxadiazol-3-yl)benzamide

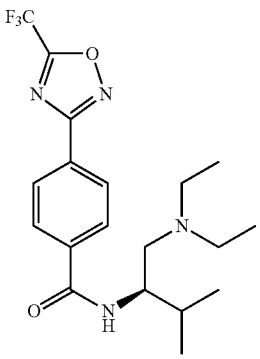 [SMILES: CCN(CC)C[C@H](NC(=O)c1ccc(-c2noc(C(F)(F)F)n2)cc1)C(C)C]

Amine: 1.0 eq, EDC: 1.3 eq HOBT: 1.15 DIPEA: 3 eq [Method C]

$Rt_{MS1}$=1.78 min., [M+H]+=398.4 as yellow thick oil.

1H NMR (400 MHz, MeOH-$d_4$) δ ppm 8.24 (d, J=8.56 Hz, 2 H), 8.03 (d, J=8.56 Hz, 2 H), 4.19 (m, 1 H), 2.56-2.76 (m, 6 H), 1.96 (m, 1 H), 0.96-1.12 (m, 12 H).

Example 135

(R)—N-(1-(diethylamino)-3-methylbutan-2-yl)-2-fluoro-4-(5-(trifluoromethyl)-1,2,4-oxadiazol-3-yl)benzamide

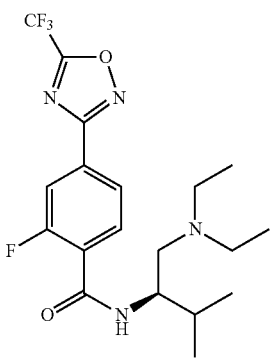 [SMILES: CCN(CC)C[C@H](NC(=O)c1ccc(-c2noc(C(F)(F)F)n2)cc1F)C(C)C]

(1.0 eq amine, 1.5 eq EDC.HCl, 1.3 eq HOBT, 3 eq DIPEA). [Method C]

$Rt_{MS1}$=1.77, 2.10 min., [M+H]+=417.4 as yellow thick oil.

1H NMR (400 MHz, MeOH-$d_4$) δ ppm 8.05 (d, J=8.07 Hz, 1 H), 7.96 (d, J=10.51 Hz, 1 H), 7.87 (t, J=7.58 Hz, 1 H), 4.18 (m, 1H), 2.55-2.74 (m, 6 H), 1.97 (m, 1 H), 0.96-1.12 (m, 12 H).

Example 136

(R)—N-(1-(ethyl(methyl)amino)propan-2-yl)-4-(5-(trifluoromethyl)-1,2,4-oxadiazol-3-yl)benzamide

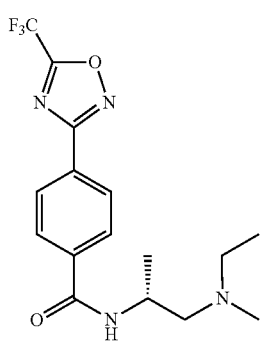 [SMILES: CCN(C)C[C@@H](C)NC(=O)c1ccc(-c2noc(C(F)(F)F)n2)cc1]

(1.2 eq amine, 1.3 eq EDC.HCl, 1.3 eq HOBT, 4 eq DIPEA). [Method C]

$Rt_{MS1}$=1.48 min., [M+H]+=357.3 as white solid.

1H NMR (400 MHz, MeOH-$d_4$) δ ppm 8.19-8.22 (m, 2 H), 8.02-8.04 (m, 2 H), 4.36 (m, 1 H), 2.36-2.71 (m, 4 H), 2.31 (d, J=2.45 Hz, 3 H), 1.21-1.31 (m, 3 H), 1.01-1.16 (m, 3 H).

Example 137

(R)—N-(1-(dipropylamino)propan-2-yl)-4-(5-(trifluoromethyl)-1,2,4-oxadiazol-3-yl)benzamide

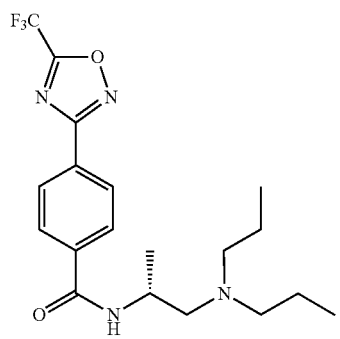 [SMILES: CCCN(CCC)C[C@@H](C)NC(=O)c1ccc(-c2noc(C(F)(F)F)n2)cc1]

(1.2 eq amine, 1.3 eq EDC.HCl, 1.3 eq HOBT, 4 eq DIPEA). [Method C]

$Rt_{MS1}$=1.76 min., [M+H]+=399.3 as white solid.

1H NMR (400 MHz, MeOH-$d_4$) δ ppm 8.23 (d, J=8.56 Hz, 2 H), 8.01 (d, J=8.56 Hz, 2 H), 4.29 (m, 1 H), 2.65 (m, 1 H), 2.42-2.57 (m, 5 H), 1.45-1.58 (m, 4 H), 1.28 (d, J=6.60 Hz, 3 H), 0.91 (t, J=7.34 Hz, 6 H).

Example 138

(R)—N-(1-(isopropyl(methyl)amino)propan-2-yl)-4-(5-(trifluoromethyl)-1,2,4-oxadiazol-3-yl)benzamide

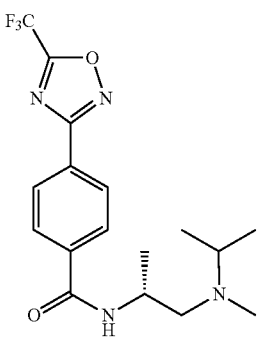 [SMILES: CC(C)N(C)C[C@@H](C)NC(=O)c1ccc(-c2noc(C(F)(F)F)n2)cc1]

(1.2 eq amine, 1.3 eq EDC.HCl, 1.3 eq HOBT, 4 eq DIPEA). [Method C]

Rt$_{MS1}$=1.53 min., [M+H]+=371.3 as white solid.

1H NMR (400 MHz, MeOH-d$_4$) δ ppm 8.18-8.25 (m, 2 H), 7.99-8.05 (m, 2 H), 4.28 (m, 1 H), 2.91 (m, 1 H), 2.63 (dd, J=12.84, 7.70 Hz, 1 H), 2.48 (dd, J=12.72, 6.11 Hz, 1 H), 2.31 (s, 3 H), 1.28 (d, J=6.60 Hz, 3 H), 1.06 (d, J=6.60 Hz, 6 H).

Example 139

(R)—N-(1-(methyl(propyl)amino)propan-2-yl)-4-(5-(trifluoromethyl)-1,2,4-oxadiazol-3-yl)benzamide

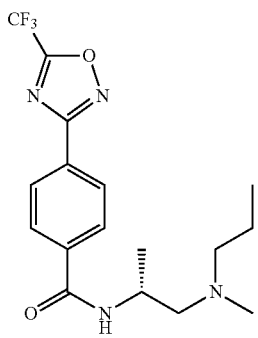 [SMILES: CCCN(C)C[C@@H](C)NC(=O)c1ccc(-c2noc(C(F)(F)F)n2)cc1]

(1.2 eq amine, 1.3 eq EDC.HCl, 1.3 eq HOBT, 4 eq DIPEA). [Method C]

Rt$_{MS1}$=1.58 min., [M+H]+=371.3 as white solid.

1H NMR (400 MHz, MeOH-d$_4$) δ ppm 8.21 (d, J=8.56 Hz, 2 H), 8.02 (d, J=8.56 Hz, 2 H), 4.35 (d, J=7.83 Hz, 1 H), 2.65 (dd, J=12.72, 8.31 Hz, 1 H), 2.35-2.50 (m, 3 H), 2.32 (s, 3 H), 1.48-1.60 (m, 2 H), 1.24-1.30 (m, 3 H), 0.92 (t, J=7.34 Hz, 3 H).

Example 140

(R)—N-(1-(ethyl(methyl)amino)propan-2-yl)-2-fluoro-4-(5-(trifluoromethyl)-1,2,4-oxadiazol-3-yl)benzamide

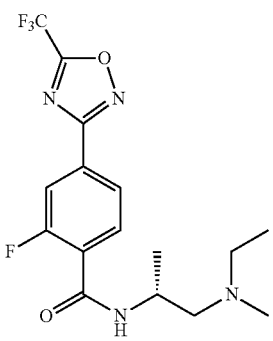 [SMILES: CCN(C)C[C@@H](C)NC(=O)c1ccc(-c2noc(C(F)(F)F)n2)cc1F]

(1.2 eq amine, 1.3 eq EDC.HCl, 1.3 eq HOBT, 3.5 eq DIPEA). [Method C]

Rt$_{MS1}$=1.47 min., [M+H]+=378.3 as yellow oil.

1H NMR (400 MHz, MeOH-d$_4$) δ ppm 8.05 (dd, J=7.95, 1.59 Hz, 1 H), 7.87-7.99 (m, 2 H), 4.32 (m, 1 H), 2.60 (d, J=7.82 Hz, 1 H), 2.48-2.58 (m, 2 H), 2.45 (q, 1 H), 2.33 (s, 3 H), 1.28 (d, J=6.60 Hz, 3 H), 1.11 (t, J=7.21 Hz, 3 H).

Example 141

(R)—N-(1-(dipropylamino)propan-2-yl)-2-fluoro-4-(5-(trifluoromethyl)-1,2,4-oxadiazol-3-yl)benzamide

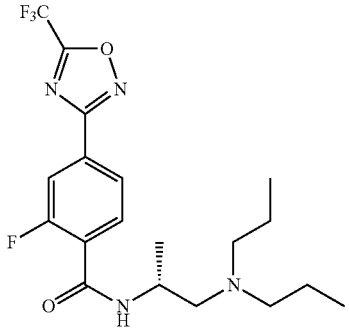 [SMILES: CCCN(CCC)C[C@@H](C)NC(=O)c1ccc(-c2noc(C(F)(F)F)n2)cc1F]

(1.2 eq amine, 1.3 eq EDC.HCl, 1.3 eq HOBT, 4 eq DIPEA). [Method C]

Rt$_{MS1}$=1.75 min., [M+H]+=417.4 as white solid.

1H NMR (400 MHz, MeOH-d$_4$) δ ppm 8.05 (m, 1 H), 7.87-7.98 (m, 2 H), 4.23 (m, 1 H), 2.62 (m, 1 H), 2.43-2.54 (m, 5 H), 1.46-1.57 (m, 4 H), 1.28 (d, J=6.60 Hz, 3 H), 0.92 (t, J=7.46 Hz, 6 H).

Example 142

(R)-2-fluoro-N-(1-(isopropyl(methyl)amino)propan-2-yl)-4-(5-(trifluoromethyl)-1,2,4-oxadiazol-3-yl)benzamide

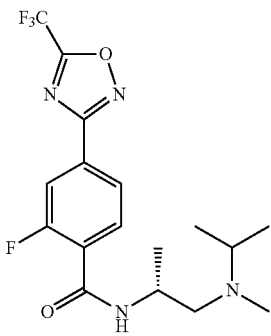 [SMILES: CC(C)N(C)C[C@@H](C)NC(=O)c1ccc(-c2noc(C(F)(F)F)n2)cc1F]

(1.2 eq amine, 1.3 eq EDC.HCl, 1.15 eq HOBT, 4 eq DIPEA). [Method C]

$Rt_{MS1}$=1.52 min., [M+H]+=389.3 as white solid.

1H NMR (400 MHz, MeOH-$d_4$) δ ppm 8.05 (dd, J=8.07, 1.47 Hz, 1 H), 7.86-8.00 (m, 2 H), 4.24 (m, 1 H), 2.90 (m, 1 H), 2.58 (m, 1 H), 2.49 (m, 1H), 1.29 (d, J=6.60 Hz, 3 H), 1.06 (d, J=6.60 Hz, 6 H).

Example 143

(R)-2-fluoro-N-(1-(methyl(propyl)amino)propan-2-yl)-4-(5-(trifluoromethyl)-1,2,4-oxadiazol-3-yl)benzamide

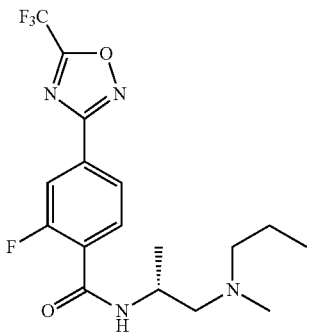

(1.2 eq amine, 1.3 eq EDC.HCl, 1.15 eq HOBT, 4 eq DIPEA). [Method C]

$Rt_{MS1}$=1.57 min., [M+H]+=389.3 as yellow oil.

1H NMR (400 MHz, MeOH-$d_4$) δ ppm 8.04 (dd, J=8.07, 1.47 Hz, 1 H), 7.86-7.97 (m, 2 H), 4.30 (m, 1 H), 2.60 (dd, J=12.72, 8.07 Hz, 1 H), 2.35-2.50 (m, 3 H), 2.32 (s, 3 H), 1.48-1.61 (m, 2 H), 1.28 (d, J=6.60 Hz, 3 H), 0.93 (t, J=7.34 Hz, 3 H).

Example 144

N-(1-(dimethylamino)propan-2-yl)-2-fluoro-N-methyl-4-(5-(trifluoromethyl)-1,2,4-oxadiazol-3-yl)benzamide

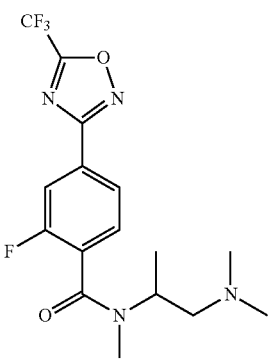 [SMILES: CC(CN(C)C)N(C)C(=O)c1ccc(-c2noc(C(F)(F)F)n2)cc1F]

(1.5 eq amine, 1.3 eq EDC.HCl, 1.15 eq HOBT, 3.1 eq DIPEA). [Method C]

$Rt_{MS1}$=1.51 min., [M+H]+=375.3 as oil.

Rotamers 1H NMR (400 MHz, MeOH-$d_4$) δ ppm 8.07 (d, J=7.82 Hz, 1 H), 7.98 (br. S., 1 H), 7.68 (m, 1 H), 5.01 (m, 0.5 H), 3.72 (m, 0.5 H), 3.01 (s, 1.4 H), 2.82 (s, 1.9 H), 2.74 (m, 0.5 H), 2.57 (m, 0.5 H), 2.35 (s, 3 H), 2.27 (m, 0.7 H), 2.08 (br. S., 3 H), 1.24 (t, J=7.46 Hz, 3 H).

The amine intermediate of formula (IV) used in the preparation of N-(1-(dimethylamino)propan-2-yl)-2-fluoro-N-methyl-4-(5-(trifluoromethyl)-1,2,4-oxadiazol-3-yl)benzamide was prepared as set out below.

Intermediate 144a: 2-((tert-butoxycarbonyl)(methyl)amino)propanoic acid

N-Me-DL-Alanine (1.5 g, 14.55 mmol) purchased from Bachem was dissolved in water (5.4 ml)/MeOH (2.7 ml) before Boc$_2$O (3.38 mL, 14.55 mmol) was added in one portion. An additional solution of Boc$_2$O (3.38 mL, 14.55 mmol) in MeOH (2.7 ml) was added over 5 min. The resulting suspension was stirred for 23 hrs at rt before the reaction mixture was poured in water and acidified to pH=3 with aqueous citric acid solution. The mixture was extracted with DCM (3×50 ml), washed with brine, dried over MgSO$_4$ and filtered. Removal of the solvent in HV yielded a transparent oil (2.6161 g, 12.87 mmol, 88% yield), which was used without further purification.

1H NMR (400 MHz, MeOH-$d_4$) δ ppm 4.25-4.76 (m, 1 H) 2.87 (br. s., 3 H) 1.47 (d, J=2.45 Hz, 9 H) 1.42 (d, J=6.60 Hz, 3 H).

Intermediate 144b: tert-butyl (1-(dimethylamino)-1-oxopropan-2-yl)(methyl)carbamate To a solution of intermediate 144a (2.6161 g, 12.87 mmol) in THF (30 mL) was added EDC.HCl (3.70 g, 19.31 mmol), HOBT (2.56 g, 16.73 mmol), Dimethylamine (2M in THF) (12.87 mL, 25.7 mmol). Then the resulting solution was stirred at 75° C. for 4-5 hrs. The reaction mixture was poured in water and basified with aqueous sat. NaHCO₃ solution then extracted with EtOAc (4×70 ml). The combined organic layers were washed with brine, dried over MgSO₄, filtered and evaporated to give tert-butyl (1-(dimethylamino)-1-oxopropan-2-yl)(methyl)carbamate (1.7619 g, 7.65 mmol, 59.4% yield) as transparent oil. The product was used without further purification in the next step.

1H NMR (400 MHz, MeOH-d₄) δ ppm 4.86-5.14 (m, 1 H) 3.06 (br. s., 3 H) 2.96 (s, 3 H) 2.77 (br. s., 3 H) 1.48 (s, 9 H) 1.27 (br. s., 3 H).

Intermediate 144c: $N^1,N^1,N^2$-trimethylpropane-1,2-diamine

To an ice-cooled solution of crude intermediate 144b (2.96 g, 12.87 mmol) in Et₂O was added dropwise a solution of LAH (1M in Et₂O) (19.31 mL, 19.31 mmol). The mixture was stirred at 0° C. until disappearance of the starting material. The reaction was carefully quenched by sequential addition of water (0.5 mL), 15% (w/w) NaOH (0.5 mL). Then diethyl ether was added and the suspension was dried with magnesium sulfate, the solids were filtered and wash with diethyl ether. The solvent was removed on HV and the crude material was dissolved in dioxane (20 ml) and cooled to 0° C. HCl (4M in dioxane) (16.09 mL, 64.4 mmol) was added slowly and the reaction was allowed to warm up to rt and stirred for 2-3 hrs. The mixture of HCl/dioxane was evaporated off under HV and captured in a cold trap to yield $N^1,N^1,N^2$-trimethylpropane-1,2-diamine (1.7276 g, 9.13 mmol, 71.0% yield) as HCl salt (viscous red oil). The amine was used for the coupling step without purification.

Example 145

(R)—N-(1-(ethyl(propyl)amino)propan-2-yl)-4-(5-(trifluoromethyl)-1,2,4-oxadiazol-3-yl)benzamide

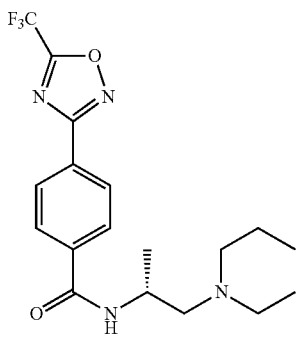 [SMILES: CCCN(CC)C[C@@H](C)NC(=O)c1ccc(-c2noc(C(F)(F)F)n2)cc1]

(1.5 eq amine, 1.3 eq EDC.HCl, 1.15 eq HOBT, 3.1 eq DIPEA). [Method C]

Rt$_{MS1}$=1.64 min., [M+H]+=385.4 as white solid.

1H NMR (400 MHz, MeOH-d₄) δ ppm 8.21 (d, J=8.31 Hz, 2 H), 8.00 (d, J=8.31 Hz, 2 H), 4.27 (m, 1 H), 2.56-2.70 (m, 3 H), 2.43-2.54 (m, 2 H), 1.61-1.43 (m, 2H), 1.26 (d, J=6.60 Hz, 3 H), 1.05 (t, J=7.21 Hz, 3 H), 0.89 (t, J=7.34 Hz, 3 H).

Example 146

(R)—N-(1-(ethyl(propyl)amino)propan-2-yl)-2-fluoro-4-(5-(trifluoromethyl)-1,2,4-oxadiazol-3-yl)benzamide

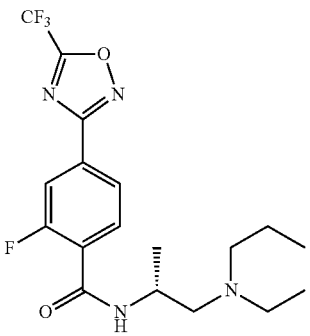

(1.2 eq amine, 1.3 eq EDC.HCl, 1.15 eq HOBT, 3 eq DIPEA). [Method C]

Rt$_{MS1}$=1.64 min., [M+H]+=403.3 as white solid.

1H NMR (400 MHz, MeOH-d₄) δ ppm 8.05 (dd, J=8.07, 1.47 Hz, 1 H), 7.86-7.99 (m, 2 H), 4.25 (m, 1 H), 2.58-2.69 (m, 3 H), 2.44-2.55 (m, 3 H), 1.45-1.59 (m, 2 H), 1.27 (d, J=6.60 Hz, 3 H), 1.07 (t, J=7.21 Hz, 3 H), 0.92 (t, J=7.46 Hz, 3 H).

Example 147

(R)—N-(1-morpholinopropan-2-yl)-4-(5-(trifluoromethyl)-1,2,4-oxadiazol-3-yl)benzamide

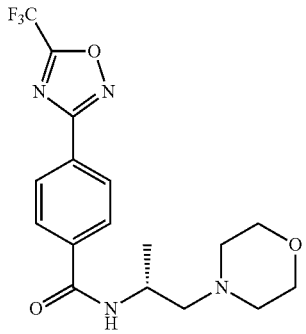

(1.2 eq amine, 1.3 eq EDC.HCl, 1.15 eq HOBT, 3 eq DIPEA). [Method C]

Rt$_{MS1}$=1.45 min., [M+H]+=385.3 as white solid.

1H NMR (400 MHz, MeOH-d$_4$) δ ppm 8.22 (d, J=8.31 Hz, 2 H), 8.01 (d, J=8.31 Hz, 2 H), 4.35 (m, 1 H), 3.67 (t, J=4.77 Hz, 4 H), 2.54-2.63 (m, 3 H), 2.49 (br. S., 2 H), 2.41 (dd, 1 H), 1.26 (d, J=6.60 Hz, 3 H).

Example 148

(R)-2-fluoro-N-(1-morpholinopropan-2-yl)-4-(5-(trifluoromethyl)-1,2,4-oxadiazol-3-yl)benzamide

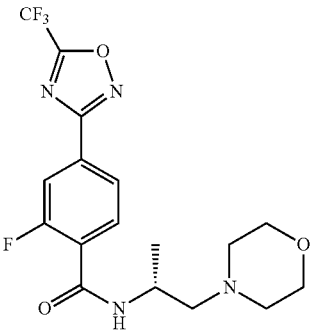 [SMILES: C[C@H](CN1CCOCC1)NC(=O)c1ccc(-c2noc(C(F)(F)F)n2)cc1F]

(1.2 eq amine, 1.3 eq EDC.HCl, 1.15 eq HOBT, 3 eq DIPEA). [Method C]

Rt$_{MS1}$=1.44 min., [M+H]+=403.3 as white solid.

1H NMR (400 MHz, MeOH-d$_4$) δ ppm 8.05 (dd, J=7.95, 1.59 Hz, 1 H), 7.96 (dd, J=10.76, 1.47 Hz, 1 H), 7.88 (dd, J=7.83, 7.09 Hz, 1 H), 4.35 (m, 1 H), 3.71 (t, J=4.65 Hz, 4 H), 2.46-2.65 (m, 5 H), 2.41 (dd, J=12.59, 5.75 Hz, 1 H), 1.28 (d, J=6.60 Hz, 3 H).

Example 149

N-(1-methylpiperidin-3-yl)-4-(5-(trifluoromethyl)-1,2,4-oxadiazol-3-yl)benzamide

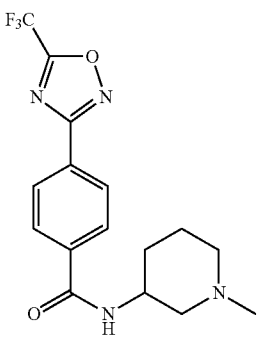 [SMILES: CN1CCCC(NC(=O)c2ccc(-c3noc(C(F)(F)F)n3)cc2)C1]

(1.2 eq amine, 1.3 eq EDC.HCl, 1.15 eq HOBT, 3 eq DIPEA). [Method C]

Rt$_{MS1}$=1.58 min., [M+H]+=371.3 as white solid.

1H NMR (400 MHz, MeOH-d$_4$) δ ppm 8.23 (d, J=8.56 Hz, 2 H), 8.03 (d, J=8.80 Hz, 2 H), 4.10-4.26 (m, 1 H), 2.88-3.06 (m, 1 H), 2.61-2.83 (m, 1 H), 2.34 (s, 3 H), 2.04-2.26 (m, 2 H), 1.96 (m, 1 H), 1.84 (m, 1 H), 1.71 (m, 1 H), 1.49 (m, 1 H).

Example 150

(R)—N-(1-(butyl(methyl)amino)propan-2-yl)-4-(5-(trifluoromethyl)-1,2,4-oxadiazol-3-yl)benzamide

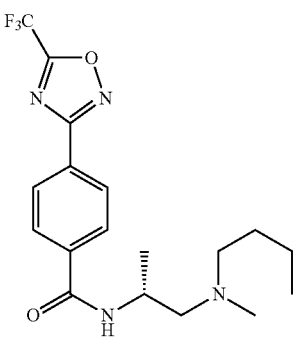

(1.2 eq amine, 1.3 eq EDC.HCl, 1.15 eq HOBT, 3 eq DIPEA). [Method C]

Rt$_{MS1}$=1.70 min., [M+H]+=385.3 as white solid.

1H NMR (400 MHz, MeOH-d$_4$) δ ppm 8.16-8.27 (m, 2 H), 7.98-8.07 (m, 2 H), 4.30-4.42 (m, 1 H), 2.66 (dd, J=12.72, 8.31 Hz, 1 H), 2.39-2.53 (m, 3 H), 2.32 (s, 3 H), 1.45-1.56 (m, 2 H), 1.30-1.41 (m, 2 H), 1.27 (d, J=6.60 Hz, 3 H), 0.94 (t, J=7.34 Hz, 3 H).

Example 151

(R)—N-(1-(butyl(methyl)amino)propan-2-yl)-2-fluoro-4-(5-(trifluoromethyl)-1,2,4-oxadiazol-3-yl)benzamide

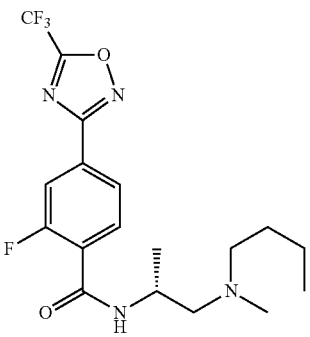 [SMILES: CCCCN(C)C[C@@H](C)NC(=O)c1ccc(-c2noc(C(F)(F)F)n2)cc1F]

(1.2 eq amine, 1.3 eq EDC.HCl, 1.15 eq HOBT, 3 eq DIPEA). [Method C]

Rt$_{MS1}$=1.70 min., [M+H]+=403.3 as white solid.

1H NMR (400 MHz, MeOH-d$_4$) δ ppm 8.05 (dd, J=7.95, 1.59 Hz, 1 H), 7.95 (dd, J=10.76, 1.47 Hz, 1 H), 7.87-7.93 (m, 1 H), 4.25-4.37 (m, 1 H) 2.60, (dd, J=12.72, 8.07 Hz, 1 H 2.36-2.52 (m, 3 H) 2.32 (s, 3 H) 1.45-1.56 (m, 2 H) 1.31-1.42 (m, 2 H) 1.28 (d, J=6.60 Hz, 3 H) 0.95 (t, J=7.34 Hz, 3 H).

Example 152

(R)—N-(1-(ethyl(isopropyl)amino)propan-2-yl)-2-fluoro-4-(5-(trifluoromethyl)-1,2,4-oxadiazol-3-yl)benzamide

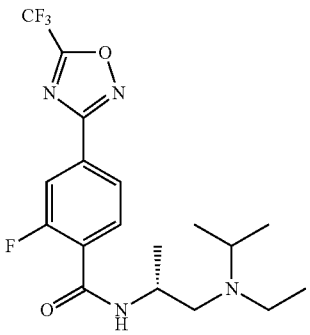 [SMILES: CCN(C[C@@H](C)NC(=O)c1ccc(-c2noc(C(F)(F)F)n2)cc1F)C(C)C]

(1.2 eq amine, 1.3 eq EDC.HCl, 1.15 eq HOBT, 3 eq DIPEA). [Method C]

$Rt_{MS1}$=1.61 min., [M+H]+=403.3 as white solid.

1H NMR (400 MHz, MeOH-$d_4$) δ ppm 8.05 (dd, J=7.95, 1.59 Hz, 1 H), 7.96 (dd, J=10.88, 1.34 Hz, 1 H), 7.91 (m, 1 H), 4.16 (d, J=6.60 Hz, 1 H), 3.05 (m, 1 H), 2.55-2.64 (m, 3 H) 2.51 (dd, 1 H), 1.29 (d, J=6.60 Hz, 3 H), 1.02-1.11 (m, 9 H).

Example 153

(R)—N-(1-methylpyrrolidin-3-yl)-4-(5-(trifluoromethyl)-1,2,4-oxadiazol-3-yl)benzamide

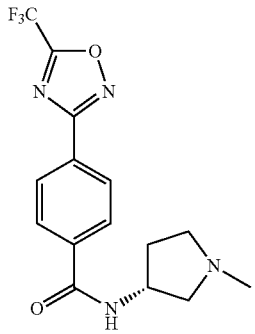 [SMILES: CN1CC[C@@H](NC(=O)c2ccc(-c3noc(C(F)(F)F)n3)cc2)C1]

The (R)-1-methylpyrrolidin-3-amine starting material used in the preparation of this compound is described in WO 2009/056551 A1 (Reference Example 5).

(1.2 eq amine, 1.3 eq EDC.HCl, 1.15 eq HOBT, 3 eq DIPEA). [Method A]

$Rt_{MS1}$=1.39 min., [M+H]+=341.2 as white solid.

1H NMR (400 MHz, MeOH-$d_4$) δ ppm 8.18-8.27 (m, 2 H), 8.00-8.07 (m, 2 H), 4.60 (dt, J=7.21, 4.46 Hz, 1 H), 2.89-3.06 (m, 2 H), 2.64-2.81 (m, 2 H), 2.50 (s, 3 H), 2.43 (m, 1 H), 1.95 (m, 1 H).

Example 154

(R)—N-(1-methylpiperidin-3-yl)-4-(5-(trifluoromethyl)-1,2,4-oxadiazol-3-yl)benzamide

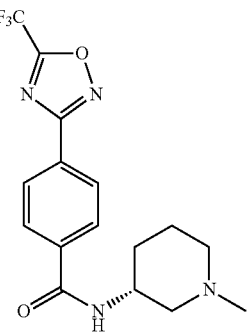

The (R)-1-methylpiperidin-3-amine used in the preparation of this compound was obtained by de-protection of (R)-tert-butyl (1-methylpiperidin-3-yl)carbamate which was prepared by a method analogous to that described in WO 2009/056551 A1 (Reference Example 5). The starting material, (R)-tert-butyl piperidin-3-ylcarbamate was purchased from CNH Technologies Inc. (Lot 13614).

(1.2 eq amine, 1.3 eq EDC.HCl, 1.15 eq HOBT, 3 eq DIPEA). [Method C]

$Rt_{MS1}$=1.45 min., [M+H]+=355.3 as white solid.

1H NMR (400 MHz, MeOH-$d_4$) δ ppm 8.19-8.27 (m, 2H), 7.99-8.06 (m, 2 H), 4.18 (m, 1 H), 2.95 (m, 1 H), 2.71 (m, 1 H), 2.34 (s, 3 H), 2.17 (br. S., 2H), 1.96 (m, 1 H), 1.84 (m, 1 H), 1.71 (m, 1 H), 1.50 (m, 1 H).

Example 155

N-(2-(diethylamino)ethyl)-4-(5-(trifluoromethyl)-1,2,4-oxadiazol-3-yl)benzamide

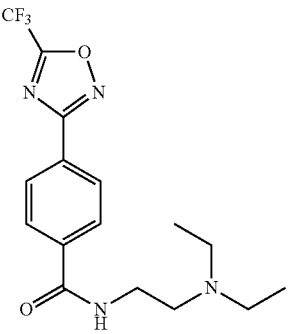 [SMILES: CCN(CC)CCNC(=O)c1ccc(-c2noc(C(F)(F)F)n2)cc1]

(1.2 eq amine, 1.3 eq EDC.HCl, 1.15 eq HOBT, 3 eq DIPEA). [Method A]

$Rt_{MS1}$=1.48 min., [M+H]+=357.3 as white solid.

1H NMR (400 MHz, MeOH-$d_4$) δ ppm 8.22 (d, J=7.83 Hz, 2 H), 7.97-8.04 (m, 2 H), 3.54 (t, J=7.09 Hz, 2 H), 2.74 (t, J=6.97 Hz, 2 H), 2.61-2.71 (m, 4 H), 1.05-1.15 (m, 6 H).

Example 156

(R)—N-(1-(benzyl(methyl)amino)propan-2-yl)-4-(5-(trifluoromethyl)-1,2,4-oxadiazol-3-yl)benzamide

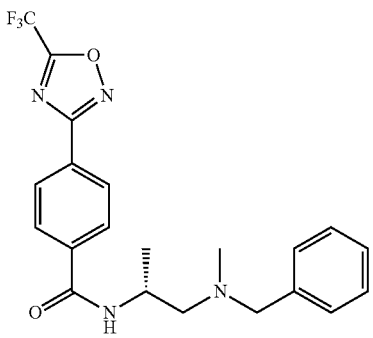 [SMILES: C[C@H](CN(C)Cc1ccccc1)NC(=O)c1ccc(-c2noc(C(F)(F)F)n2)cc1]

(1.2 eq amine, 1.3 eq EDC.HCl, 1.15 eq HOBT, 3 eq DIPEA). [Method C]

$Rt_{MS1}$=1.78 min., [M+H]+=419.3 as white solid.

1H NMR (400 MHz, MeOH-$d_4$) δ ppm 8.24 (d, J=8.56 Hz, 2H), 8.02 (d, J=8.56 Hz, 2 H), 7.18-7.37 (m, 5 H), 4.41 (m, 1 H), 3.50-3.70 (m, 2 H), 2.63 (dd, J=12.47, 8.31 Hz, 1 H), 2.46 (dd, J=12.59, 5.99 Hz, 1 H), 2.29 (s, 3 H), 1.27 (d, J=6.85 Hz, 3 H).

Example 157

N-(2-(methylamino)ethyl)-4-(5-(trifluoromethyl)-1,2,4-oxadiazol-3-yl)benzamide

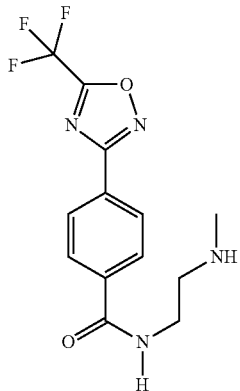 [SMILES: CNCCNC(=O)c1ccc(-c2noc(C(F)(F)F)n2)cc1]

Intermediate 157a (761 mg, 1.836 mmol) was dissolved in DCM (5 ml). After cooling to 0° C. (water/ice bath) TFA (2 ml) was added dropwise. The reaction mixture was stirred at the same temperature for 1 hr. Water was added and the pH of the mixture was adjusted to pH 7 with 1N LiOH. After phase separation the aq layer was extracted twice with DCM, combined, dried over $MgSO_4$ filtrated and the solvent was removed in vacuum. 34 mg of the crude were subjected to purification by reverse phase prep-HPLC (gradient elution, water/ACN both containing 0.1% TFA). Fractions containing the desired compound were combined and freeze-dried to yield the product as white salt.

$Rt_{MS2}$=2.14 min., [M+H]+=315.1 as white solid.

1H NMR (400 MHz, DMSO-$d_6$) δ ppm 8.91 (t, J=5.62 Hz, 1 H), 8.51 (br. S., 2 H), 8.17-8.25 (m, 2 H), 8.06-8.14 (m, 2 H), 3.59 (q, J=5.75 Hz, 2 H), 3.13 (br.s., 2 H), 2.63 (br. S., 3 H).

Intermediate 157a: tert-butyl methyl(2-(4-(5-(trifluoromethyl)-1,2,4-oxadiazol-3-yl)benzamido)ethyl)carbamate To a suspension of 4-(5-(trifluoromethyl)-1,2,4-oxadiazol-3-yl)benzoic acid (1 g, 3.87 mmol) in DCM (10 ml) was added COMU (1.825 g, 4.26 mmol) and DIPEA (0.812 ml, 4.65 mmol). The yellow solution was stirred for 2 min at rt and turned red. N-Boc-N-methyl-ethylenediamine (0.810 g, 4.65 mmol) was added and the reaction mixture was stirred at reflux for 1 hr, allowed to cool to rt and washed with water, saturated aqueous $NH_4Cl$, and extracted with EtOAc. The organic layer was dried over $Na_2SO_4$ and the solvent was removed in vacuum. The final product was purified according to Method B in Examples 124-156 general method.

Example 158

N-(2-(phenylamino)ethyl)-4-(5-(trifluoromethyl)-1,2,4-oxadiazol-3-yl)benzamide

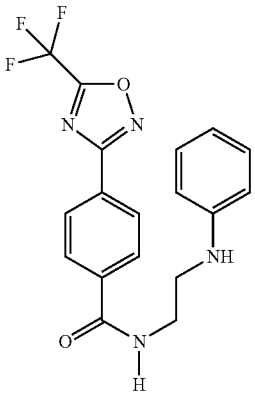 [SMILES: O=C(NCCNc1ccccc1)c1ccc(-c2noc(C(F)(F)F)n2)cc1]

Example 158 was prepared in a manner analogous to that used to make Example 157.

$Rt_{MS2}$2=4.73 min., [M+H]+=377.1 as white solid.

1H NMR (400 MHz, DMSO-$d_6$) δ ppm 8.82 (t, J=5.62 Hz, 1 H), 8.13-8.22 (m, 2 H), 8.04-8.13 (m, 2 H), 7.09 (dd, J=8.31, 7.34 Hz, 2 H), 6.63 (d, J=7.70 Hz, 2 H), 6.54 (t, J=7.21 Hz, 1 H), 5.73 (t, J=5.87 Hz, 1 H), 3.47 (q, J=6.52 Hz, 2 H), 3.24 (q, J=6.36 Hz, 2 H).

The invention claimed is:

1. A compound of formula (I), or a pharmaceutically acceptable salt thereof,

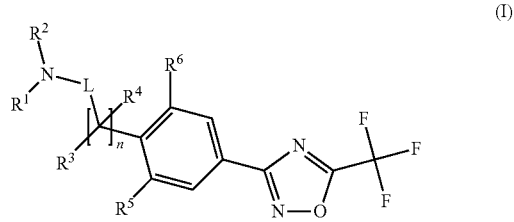

wherein

L represents —C(=O)— or —S(=O)$_m$— and m represents 1 or 2;

either

R$^1$ represents C$_{1-6}$alkyl, C$_{2-6}$alkenyl, C$_{2-6}$alkynyl, halogenC$_{1-6}$alkyl, C$_{1-6}$alkoxy, C$_{1-6}$alkoxyC$_{1-6}$alkyl, C$_{1-6}$alkylcarbonylC$_{1-6}$alkyl, C$_{1-6}$alkoxycarbonylC$_{1-6}$alkyl, hydroxyC$_{1-6}$alkyl, aminoC$_{1-6}$alkyl, C$_{1-4}$alkylaminoC$_{1-6}$alkyl, diC$_{1-4}$alkylaminoC$_{1-6}$alkyl, aminocarbonylC$_{1-6}$alkyl, C$_{1-4}$alkylaminocarbonylC$_{1-6}$alkyl, diC$_{1-4}$alkylaminocarbonylC$_{1-6}$alkyl, C$_{3-8}$cycloalkylC$_{0-6}$alkyl, phenylC$_{0-6}$alkyl, heteroarylC$_{0-6}$alkyl wherein the heteroaryl moiety is a 5- or 6- membered aromatic ring which comprises 1, 2, 3 or 4 heteroatoms individually selected from N, O and S, heterocyclylC$_{0-6}$alkyl wherein the heterocyclyl moiety is a 5- or 6- membered non-aromatic ring which comprises 1, 2 or 3 heteroatoms individually selected from N, O and S, or —CR$^7$R$^8$ wherein R$^7$ represents phenylC$_{0-5}$alkyl and R$^8$ represents diC$_{1-2}$alkylaminoC$_{1-4}$alkyl, and wherein any of said cycloalkyl, phenyl, heteroaryl and heterocyclyl moieties are optionally substituted by 1, 2, 3, 4 or 5 substituents, which may be the same or different, selected from R$^9$, R$^2$ represents hydrogen or methyl, or R$^1$ and R$^2$, together with the nitrogen atom to which they are attached, form a 5- or 6-membered non-aromatic heterocyclic ring which optionally comprises one additional heteroatom ring member selected from N and O and wherein said heterocyclic ring is optionally substituted by 1, 2, 3, 4 or 5 substituents, which may be the same or different, selected from R$^9$;

R$^3$ and R$^4$ independently represent hydrogen or methyl;

n represents 0 or 1;

R$^5$ and R$^6$ independently represent hydrogen, halogen, methyl or methoxy;

R$^9$ represents cyano, amino, halogen, hydroxy, C$_{1-4}$alkyl, C$_{2-4}$alkenyl, C$_{2-4}$alkynyl, halogenC$_{1-4}$alkyl, C$_{1-4}$alkoxy, C$_{1-4}$alkylamino, diC$_{1-4}$alkylamino, C$_{1-4}$alkylcarbonyl, C$_{1-4}$alkoxycarbonyl, aminocarbonyl, C$_{1-4}$alkylaminocarbonyl, diC$_{1-4}$alkylaminocarbonyl, or C$_{1-4}$alkoxycarbonylamino.

2. A compound according to claim 1, or a pharmaceutically acceptable salt thereof, wherein L represents —C(=O)—.

3. A compound according to claim 1, or a pharmaceutically acceptable salt thereof, wherein R$^1$ represents C$_{1-6}$alkyl, C$_{2-6}$alkenyl, C$_{2-6}$alkynyl, halogenC$_{1-6}$alkyl, C$_{1-6}$alkoxy, C$_{1-6}$alkoxyC$_{1-6}$alkyl, C$_{1-6}$alkylcarbonylC$_{1-6}$alkyl, C$_{1-6}$alkoxycarbonylC$_{1-6}$alkyl, hydroxyC$_{1-6}$alkyl, aminoC$_{1-6}$alkyl, C$_{1-4}$alkylaminoC$_{1-6}$alkyl, diC$_{1-4}$alkylaminoC$_{1-6}$alkyl, aminocarbonylC$_{1-6}$alkyl, C$_{1-4}$alkylaminocarbonylC$_{1-6}$alkyl, or diC$_{1-4}$alkylaminocarbonylC$_{1-6}$alkyl.

4. A compound according to claim 1, or a pharmaceutically acceptable salt thereof, wherein R$^1$ represents aminoC$_{1-6}$alkyl, C$_{1-4}$alkylaminoC$_{1-6}$alkyl or diC$_{1-4}$alkylaminoC$_{1-6}$alkyl.

5. A compound according to claim 1, or a pharmaceutically acceptable salt thereof, wherein R$^1$ represents C$_{1-4}$alkylaminoC$_{1-6}$alkyl or diC$_{1-4}$alkylaminoC$_{1-6}$alkyl.

6. A compound according to claim 1, or a pharmaceutically acceptable salt thereof, wherein R$^2$ represents hydrogen.

7. A compound according to claim 1, or a pharmaceutically acceptable salt thereof, wherein n represents 0.

8. A compound according to claim 1, or a pharmaceutically acceptable salt thereof, wherein R$^5$ and R$^6$ individually represent hydrogen or fluoro.

9. A compound according to claim 1, or a pharmaceutically acceptable salt thereof, wherein R$^5$ and R$^6$ both represent hydrogen.

10. A compound of formula (I), or a pharmaceutically acceptable salt thereof,

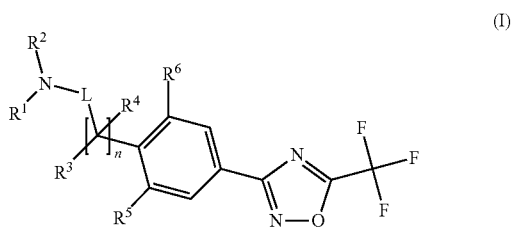

wherein

L represents —C(=O)— or —S(=O)$_m$—and m represents 1 or 2;

R$^1$ represents phenylC$_{0-6}$alkylaminoC$_{1-6}$alkyl or phenylC$_{0-6}$alkylamino(C$_{1-4}$alkyl)C$_{1-6}$alkyl, and wherein any of said phenyl moieties are optionally substituted by 1, 2, 3, 4 or 5 substituents, which may be the same or different, selected from R$^9$, R$^2$ represents hydrogen or methyl, R$^3$ and R$^4$ independently represent hydrogen or methyl;

n represents 0 or 1;

R$^5$ and R$^6$ independently represent hydrogen, halogen, methyl or methoxy; and R$^9$ represents cyano, amino, halogen, hydroxy, C$_{1-4}$alkyl, C$_{2-4}$alkenyl, C$_{2-4}$alkynyl, halogenC$_{1-4}$alkyl, C$_{1-4}$alkoxy, C$_{1-4}$alkylamino, diC$_{1-4}$alkylamino, C$_{1-4}$alkylcarbonyl, C$_{1-4}$alkoxycarbonyl, aminocarbonyl, C$_{1-4}$alkylaminocarbonyl, diC$_{1-4}$alkylaminocarbonyl or C$_{1-4}$alkoxycarbonylamino.

11. A compound according to claim 1, which is selected from:

N,N-dimethyl-4-(5-(trifluoromethyl)-1,2,4-oxadiazol-3-yl)benzamide;

N-methyl-4-(5-(trifluoromethyl)- 1,2,4-oxadiazol-3-yl)benzamide;

N-methyl-2[4-(5-trifluoromethyl-[ 1,2,4]oxadiazol-3-yl)-phenyl]-acetamide;

N,N-dimethyl-2-[4-(5-trifluoromethyl[1,2,4]oxadiazol-3-yl)-phenyl]-acetamide;

N-Isopropyl-2-[4-(5-trifluoromethyl-[1,2,4]oxadiazol-3-yl)-phenyl]-acetamide;

N-butyl-2-(4-(5-(trifluoromethyl)-1,2,4-oxadiazol-3-yl)phenyl)acetamide;

N-(2-methoxyethyl)-2-(4-(5-(trifluoromethyl)- 1,2,4-oxadiazol-3-yl)phenyl)acetamide;

ethyl 2-(2-(4-(5-(trifluoromethyl)- 1,2,4-oxadiazol-3-yl)phenyl)acetamido)acetate;

1-morpholino-2-(4-(5-(trifluoromethyl)-1,2,4-oxadiazol-3 -yl)phenyl)ethanone;

1-(4-methylpiperazin-1-yl)-2-(4-(5 -(trifluoromethyl)-1,2,4-oxadiazol-3-yl)phenyl)ethanone;

N-methoxy-N-methyl-2-(4-(5-(trifluoromethyl)-1,2,4-oxadiazol-3-yl)phenyl)acetamide;

N-ethyl-4-(5-(trifluoromethyl)-1,2,4-oxadiazol-3-yl)benzamide;

N-(2-hydroxyethyl)-4-(5-(trifluoromethyl)-1,2,4-oxadiazol-3-yl)benzamide;

N-ethyl-N-methyl-4-(5-(trifluoromethyl)-4-oxadiazol-3-yl)benzamide;

N-(2-hydroxyethyl)-N-methyl-4-(5-(trifluoromethyl)-1,2,4-oxadiazol-3-yl)benzamide;
N-(2-methoxyethyl)-4-(5-(trifluoromethyl)-1,2,4-oxadiazol-3-yl)benzamide;
N-(3-hydroxypropyl)-4-(5-(trifluoromethyl)-1,2,4-oxadiazol-3-yl)benzamide;
N-(2-methoxyethyl)-N-methyl-4-(5-(trifluoromethyl)-1,2,4-oxadiazol-3-yl)benzamide;
N-cyclopropyl-4-(5-(trifluoromethyl)- 1,2,4-oxadiazol-3-yl)benzamide;
N-isopropyl-4-(5-(trifluoromethyl)-1,2,4-oxadiazol-3-yl)benzamide;
N-(3-methoxypropyl)-4-(5-(trifluoromethyl)-1,2,4-oxadiazol-3-yl)benzamide;
N-(2-fluoroethyl)-4-(5 -(trifluoromethyl)-1,2,4-oxadiazol-3-yl)benzamide;
pyrrolidin-1-yl(4-(5-(trifluoromethyl)-1,2,4-oxadiazol-3-yl)phenyl)methanone;
N-isopropyl-N-methyl-4-(5-(trifluoromethyl)-1,2,4-oxadiazol-3-yl)benzamide;
N-cyclobutyl-4-(5-(trifluoromethyl)-1,2,4-oxadiazol-3-yl)benzamide;
N-(cyclopropylmethyl)-4-(5-(trifluoromethyl)-1,2,4-oxadiazol-3-yl)benzamide;
N-isobutyl-4-(5-(trifluoromethyl)-1,2,4-oxadiazol-3 -yl)benzamide;
(R)-N-(1-hydroxypropan-2yl)-4(5-(trifluoromethyl)-1,2,4-oxadiazol-3-yl)benzamide;
N-cyclopentyl-4-(5-(trifluoromethyl)- 1,2,4-oxadiazol-3-yl)benzamide;
N-(pentan-3-yl)-4-(5-(trifluoromethyl)-1,2,4-oxadiazol-3-yl)benzamide;
N-(2-(dimethylamino)ethyl)-4-(5-(trifluoromethyl)-1,2,4-oxadiazol-3-yl)benzamide;
morpholino(4-(5-(trifluoromethyl)-1,2,4-oxadiazol-3-yl)phenyl)methanone;
piperidin-1-yl(4-(5-(trifluoromethyl)-1,2,4-oxadiazol-3-yl)phenyl)methanone;
N-cyclohexyl-4-(5-(trifluoromethyl)-1,2,4-oxadiazol-3-yl)benzamide;
N-phenyl-4-(5-(trifluoromethyl)-1,2,4-oxadiazol-3-yl)benzamide;
(4-methylpiperazin- 1-yl)(4-(5-(trifluoromethyl)-1,2,4-oxadiazol-3-yl)phenyl)methanone;
N-(2-(dimethylamino)ethyl)-N-methyl-4-(5-(trifluoromethyl)- 1,2,4-oxadiazol-3-yl)benzamide;
N-(1-methylpiperidin-4-yl)-4-(5-(trifluoromethyl)-1,2,4-oxadiazol-3-yl)benzamide;
(4-(dimethylamino)piperidin- 1-yl)(4-(5-(trifluoromethyl)-1,2,4-oxadiazol-3-yl) phenyl)methanone;
N-(3-(1H-imidazol- 1-yl)propyl)-4-(5-(trifluoromethyl)-1,2,4-oxadiazol-3-yl)benzamide;
N-(4-(dimethylamino)phenyl)-4-(5-(trifluoromethyl)-1,2,4-oxadiazol-3-yl)benzamide;
N-phenethyl-4-(5-(trifluoromethyl)- 1,2,4-oxadiazol-3-yl)benzamide;
N-benzyl-4-(5-(trifluoromethyl)-1,2,4-oxadiazol-3-yl)benzamide;
N-(pyridin-4-yl)-4-(5-(trifluoromethyl)-1,2,4-oxadiazol-3-yl)benzamide;
N-(pyridin-3-yl)-4-(5-(trifluoromethyl)-1,2,4-oxadiazol-3-yl)benzamide;
N-((1-methylpiperidin-4-yl)methyl)-4-(5-(trifluoromethyl)-1,2,4-oxadiazol-3-yl)benzamide;
(S)-N-(1-hydroxypropan-2-yl)-4-(5-(trifluoromethyl)-1,2,4-oxadiazol-3-yl)benzamide;
N-(2-(dimethylamino)propyl)-4-(5-(trifluoromethyl)-1,2,4-oxadiazol-3-yl)benzamide;
N-(2-(dimethylamino)-2-oxoethyl)-4-(5-(trifluoromethyl)-1,2,4-oxadiazol-3-yl)benzamide;
N-(1-(dimethylamino)propan-2-yl)-4-(5-(trifluoromethyl)-1,2,4-oxadiazol-3-yl)benzamide;
(3 -hydroxypyrrolidin- 1-yl)(4-(5-(trifluoromethyl)- 1,2,4-oxadiazol-3-yl)phenyl)methanone;
tert-butyl 4-(4-(5-(trifluoromethyl)- 1,2,4-oxadiazol-3-yl)benzoyl)piperazine- 1-carboxylate;
N-(1-hydroxybutan-2-yl)-4-(5-(trifluoromethyl)-1,2,4-oxadiazol-3-yl)benzamide;
N-(tetrahydro-2H-pyran-4-yl)-4-(5-(trifluoromethyl)-1,2,4-oxadiazol-3-yl)benzamide;
N-(1-hydroxy-4-methylpentan-2-yl)-4-(5-(trifluoromethyl)-1, 2,4-oxadiazol-3-yl)benzamide;
4-[4-(5-trifluoromethyl-[1,2,4]oxadiazol-3-yl)-benzoylamino]-piperidine-1-carboxylic acid tert-butyl ester;
tert-butyl (2-(4-(5-(trifluoromethyl)-1,2,4-oxadiazol-3-yl)benzamido)cyclohexyl)carbamate;
N-(2-hydroxycyclohexyl)-4-(5(trifluoromethyl)-1,2,4-oxadiazol-3-yl)benzamide;
tert-butyl 3-(4-(5-(trifluoromethyl)-1,2,4-oxadiazol-3-yl)benzamido)piperidine- 1-carboxylate;
N-(2-(methylamino)-2-oxoethyl)-4-(5-(trifluoromethyl)-1,2,4-oxadiazol-3-yl)benzamide;
N-(1- acetylpiperidin-4-yl)-4-(5 -(trifluoromethyl)-1,2,4-oxadiazol-3-yl)benzamide;
N-(1,2,2,6,6-pentamethylpiperidin-4-yl)-4-(5-(trifluoromethyl)-1, 2,4-oxadiazol-3-yl)benzamide;
tert-butyl 3-(4-(5-(trifluoromethyl)-1,2,4-oxadiazol-3-yl)benzamido)pyrrolidine-1-carboxylate;
N-(2-methoxypyridin-4-yl)-4-(5-(trifluoromethyl)-1,2,4-oxadiazol-3-yl)benzamide;
N-(2,6-dimethylpyridin-4-yl)-4-(5-(trifluoromethyl)-1, 24-oxadiazol-3-yl)benzamide;
N-(2-(tert-butyl)pyridin-4-yl)-4-(5-(trifluoromethyl)-1,2,4-oxadiazol-3-yl)benzamide;
N-(2-methylpyridin-4-yl)-4-(5-(trifluoromethyl)-1,2,4-oxadiazol-3-yl)benzamide;
N-(2-fluoropyridin-4-yl)-4-(5-(trifluoromethyl)-1,2,4-oxadiazol-3-yl)benzamide;
N-(2-hydroxypyridin-4-yl)-4-(5-(trifluoromethyl)-1,2,4-oxadiazol-3-yl)benzamide;
N-(2-cyanopyridin-4-yl)-4-(5-(trifluoromethyl)-1,2,4-oxadiazol-3-yl)benzamide;
4-(5-(trifluoromethyl)-1,2,4-oxadiazol-3-yl)-N-(2-(trifluoromethyl)pyridin-4-yl)benzamide;
N-(2-chloropyridin-4-yl)-4-(5-(trifluoromethyl)-1,2,4-oxadiazol-3-yl)benzamide;
N-(piperidin-4-yl)-4-(5-(trifluoromethyl)-1,2,4-oxadiazol-3-yl)benzamide;
N-(2- aminocyclohexyl)-4-(5-(trifluoromethyl)-1,2,4-oxadiazol-3-yl)benzamide;
N-(piperidin-2-ylmethyl)-4-(5-(tifluoromethyl)-1,2,4-oxadiazol-3 -yl)benzamide;
N-(piperidin-3-yl)-4-(5-(trifluoromethyl)- 1,2,4-oxadiazol-3-yl)benzamide;
N-(pyrrolidin-3-yl)-4-(5-(trifluoromethyl)-1,2,4-oxadiazol-3-yl)benzamide;
(R)-N-(1-(dimethylamino)propan-2-yl)-4-(5-(trifluoromethyl)-1,2,4-oxadiazol-3-yl)benzamide;
(S)-N-(1-(dimethylamino)propan-2-yl)-4-(5-(trifluoromethyl)-1,2,4-oxadiazol-3-yl)benzamide;
(S)-N-(1-(dimethylamino)-3-methylbutan-2-yl)-4-(5-(trifluoromethyl)-1,2,4-oxadiazol-3-yl)benzamide;

(R)-N-(1-(dimethylamino)-3-methylbutan-2-yl)-4-(5-(tri-fluoromethyl)-1,2,4-oxadiazol-3-yl) benzamide;
(R)-N-(1-(dimethylamino)-4-methylpentan-2-yl)-4-(5-(trifluoromethyl)-1,2,4-oxadiazol-3-yl) benzamide;
(R)-N-(pyrrolidin-3-yl)-4-(5-(trifluoromethyl)-1,2,4-oxadiazol-3 -yl)benzamide;
(S)-N-(pyrrolidin-3-yl)-4-(5-(trifluoromethyl)-1,2,4-oxadiazol-3-yl)benzamide;
(R)-N-(1-(dimethylamino)propan-2-yl)-2-fluoro-4-(5-(trifluoromethyl)-1,2,4-oxadiazol-3-yl) benzamide;
(R)-N-(1-(dimethylamino)-3-methylbutan-2-yl)-2-fluoro-4-(5 -(trifluoromethyl)-1,2,4-oxadiazol-3 -yl) benzamide;
N-(2,6-dimethylpyridin-4-yl)-2-fluoro-4-(5-(trifluoromethyl)- 1,2,4-oxadiazol-3-yl)benzamide;
2-fluoro-N- (1-hydroxypropan-2-yl)-4-(5-(trifluoromethyl)- 1,2,4-oxadiazol-3-yl) benzamide;
(R)-N-(1-(dimethylamino)-3-phenylpropan-2-yl)-4-(5-(trifluoromethyl)-1,2,4-oxadiazol-3-yl) benzamide;
(S)-N-(1-(dimethylamino)-3-phenylpropan-2-yl)-4-(5-(trifluoromethyl)-1,2,4-oxadiazol-3-yl) benzamide;
N-(1 -(dimethylamino)propan-2-yl)-N-methyl-4-(5-(trifluoromethyl)-1,2,4-oxadiazol-3-yl) benzamide;
(R)-2-fluoro-N-(pyrrolidin-3-yl)-4-(5-(trifluoromethyl)-1,2,4- oxadiazol-3-yl)benzamide;
N-phenyl-4-(5-(trifluoromethyl)-1,2,4-oxadiazol-3-yl) benzenesulfonamide;
N-benzyl-4-(5-(trifluoromethyl)-1,2,4-oxadiazol-3 -yl) benzenesulfonamide;
N-(2-(dimethylamino)ethyl)-4-(5-(trifluoromethyl)-1,2, 4-oxadiazol-3-yl) benzenesulfonamide;
N-(2-(dimethylamino)ethyl)-N-methyl-4-(5-(trifluoromethyl)-1,2,4- oxadiazol-3-yl) benzenesulfonamide;
N-(pyridin-3-yl)-4-(5-(trifluoromethyl)-1,2,4-oxadiazol-3 -yl)benzenesulfonamide;
N-(cyclohexylmethyl)-4-(5-(trifluoromethyl)-1,2,4-oxadiazol-3-yl)benzenesulfonamide; and
(R)-N-(pynolidin-3-yl)-4-(5-(trifluoromethyl)-1,2,4-oxadiazol-3-yl)benzenesulfonamide;
or a pharmaceutically acceptable salt thereof.

12. A compound according to claim 1, which is selected from:
N-o-tolyl-4-(5-trifluoromethyl[1,2,4]oxadiazol-3 -yl)-benzenesulfonamide;
N-(2-chlorophenyl)-4-(5-(trifluoromethyl)-1,2,4-oxadiazol-3-yl)benzenesulfonamide;
N-m-tolyl-4(5-(trifluoromethyl)-1,2,4-oxadiazol-3-yl) benzenesulfonamide;
N-(3-fluorophenyl)-4-(5-(trifluoromethyl)-1,2,4-oxadiazol-3-yl)benzenesulfonamide;
N-(3-chlorophenyl)-4-(5-(trifluoromethyl)-1,2,4-oxadiazol-3-yl)benzenesulfonamide;
N-p-tolyl-4-(5-(trifluoromethyl)-1,2,4-oxadiazol-3-yl) benzenesulfonamide;
N-(4-fluorophenyl)-4-(5-(trifluoromethyl)-1,2,4-oxadiazol-3-yl)benzenesulfonamide;
N-(4-chlorophenyl)-4-(5-(trifluoromethyl)-1,2,4-oxadiazol-3-yl)benzenesulfonamide;
N-(2-fluorophenyl)-4-(5-(trifluoromethyl)-1,2,4-oxadiazol-3-yl)benzenesulfonamide;
N-(3-(dimethylamino)propyl)-N-methyl-4-(5-(trifluoromethyl)-1,2,4-oxadiazol-3-yl) benzenesulfonamide;
N-(3-(dimethylamino)propyl)-4-(5-(trifluoromethyl)-1,2, 4-oxadiazol-3-yl)benzenesulfonamide;
N,N-dimethyl-4-(5-(trifluoromethyl)-1,2,4-oxadiazol-3-yl)benzenesulfonamide;
N-((1-methylpyrrolidin-3-yl)methyl)-4-(5-(trifluoromethyl)-1,2,4-oxadiazol-3-yl) benzenesulfonamide;
N-(3-hydroxypropyl)-4-(5-(trifluoromethyl)-1,2,4-oxadiazol-3-yl)benzenesulfonamide;
(S)-N-(1-(dimethylamino)-3-phenylpropan-2-yl)-2-fluoro-4-(5 -(trifluoromethyl)-1,2,4-oxadiazol -3-yl) benzamide;
(R)-N-(1-(dimethylamino)-3-phenylpropan-2-yl)-2-fluoro-4-(5 -(trifluoromethyl)-1,2,4-oxadiazol -3-yl) benzamide;
N-(1-(dimethylamino)-2-methylpropan-2-yl)-4-(5-(trifluoromethyl)-1,2,4-oxadiazol-3-yl) benzamide;
N-(1-(dimethylamino)-2-methylpropan-2-yl)-2-fluoro-4-(5-(trifluoromethyl)-1,2,4-oxadiazol-3-yl) benzamide;
N-(1-(diethylamino)propan-2-yl)-2-fluoro-4-(5-(trifluoromethyl)-1,2,4-oxadiazol-3-yl) benzamide;
N-(2-(dimethylamino)propyl)-2-fluoro-4-(5-(trifluoromethyl)-1, 2,4-oxadiazol-3-yl)benzamide;
N-(1-(diethylamino)propan-2-yl)-4-(5-(trifluoromethyl)-1,2,4-oxadiazol-3-yl)benzamide;
(R)-N-(1-(dimethylamino)propan-2-yl)-2,6-difluoro-4-(5-(trifluoromethyl)-1,2,4-oxadiazol-3-yl) benzamide;
(R)-2-chloro-N-(1-(dimethylamino)propan-2-yl)-4-(5-(trifluoromethyl)-1,2,4-oxadiazol-3-yl) benzamide;
(R)-N-(1-(diethylamino)propan-2-yl)-2-fluoro-4-(5-(trifluoromethyl)-1,2,4-oxadiazol-3-yl) benzamide;
(S)-N-(1-(diethylamino)propan-2-yl)-2-fluoro-4-(5-(trifluoromethyl)-1,2,4-oxadiazol-3-yl) benzamide;
(R)-2-fluoro-N-(1-(pyrrolidin- 1-yl)propan-2-yl)-4-(5-(trifluoromethyl)-1,2,4-oxadiazol-3-yl) benzamide;
(R)-2-fluoro-N-(1-(piperidin-1-yl)propan-2-yl)-4-(5-(trifluoromethyl)-1,2,4-oxadiazol-3 -yl) benzamide;
(R)-N-(1-(pyrrolidin-1-yl)propan-2-yl)-4-(5-(trifluoromethyl)- 1,2,4-oxadiazol-3-yl)benzarnide;
(R)-N-(1-(piperidin-1-yl)propan-2-yl)-4-(5-(trifluoromethyl)- 1,2,4-oxadiazol-3yl)benzamide;
(R)-N-(1-(diethylamino)propan-2-yl)-4-(5-(trifluoromethyl)-1,2,4-oxadiazol-3-yl)benzamide;
(S)-N-(1-(diethylamino)propan-2-yl)-4-(5-(trifluoromethyl)-1,2,4-oxadiazol-3 -yl)benzamide;
(R)-N-(1-(diethylamino)-3-methylbutan-2yl)-4-(5-(trifluoromethyl)-1,2,4-oxadiazol-3-yl) benzamide;
(R)-N-(1-(diethylamino)-3-methylbutan-2yl(-2-fluoro-4-(5-(trifluoromethyl)-1,2,4-oxadiazol-3-yl) benzamide;
(R)-N-(1-(ethyl(methyl)amino)propan-2-yl)-4-(5-(trifluoromethyl)-1,2,4-oxadiazol-3-yl) benzamide;
(R)-N-(1-(dipropylamino)propan-2-yl)-4-(5-(trifluoromethyl)-1,2,4-oxadiazol-3-yl)benzamide;
(R)-N-(1-(isopropyl(methyl)amino)propan-2-yl)-4-(5-(trifluoromethyl)-1,2,4-oxadiazol-3-yl) benzamide;
(R)-N-(1-(methyl(propyl)amino)propan-2-yl)-4-(5-(trifluoromethyl)-1,2,4-oxadiazol-3-yl) benzamide;
(R)-N-(1-(ethyl(methyl)amino)propan-2-yl)-2-fluoro-4-(5-(trifluoromethyl)-1,2,4-oxadiazol-3-yl) benzamide;
(R)-N-(1-(dipropylamino)propan-2-yl)-2-fluoro-4-(5-(trifluoromethyl)-1,2,4-oxadiazol-3-yl) benzamide;
(R)-2-fluoro-N-(1-(isopropyl(methyl)amino)propan-2-yl)-4-(5-(trifluoromethyl)-1,2,4-oxadiazol-3-yl) benzamide;
(R)-2-fluoro-N-(1-(methyl(propyl)amino)propan-2-yl)-4-(5-(trifluoromethyl)-1,2,4-oxadiazol-3-yl) benzamide;
N-(1-(dimethylamino)propan-2-yl)-2-fluoro-N-methyl-4-(5-(trifluoromethyl)-1,2, 4-oxadiazol-3-yl) benzamide;
(R)-N-(1-(ethyl(propyl)amino)propan-2-yl)-4-(5-(trifluoromethyl)-1,2,4-oxadiazol-3-yl) benzamide;
(R)-N-(1-(ethyl(propyl)amino)propan-2-yl)-2-fluoro-4-(5-(trifluoromethyl)-1,2,4-oxadiazol-3-yl) benzamide;

(R)-N-(1-morpholinopropan-2-yl)-4-(5-(trifluoromethyl)-1,2,4-oxadiazol-3-yl)benzamide;
(R)-2-fluoro-N-(1-morpholinopropan-2-yl)-4(5-(trifluoromethyl)-1,2,4-oxadiazol-3-yl) benzamide;
N-(1-methylpiperidin-3-yl)-4-(5-(trifluoromethyl)-1,4-oxadiazol-3-yl)benzamide;
(R)-N-(1-(butyl(methyl)amino)propan-2-yl)-4-(5-(trifluoromethyl)-1,2,4-oxadiazol-3-yl) benzamide;
(R)-N-(1-(butyl(methyl)amino)propan-2-yl)-2-fluoro-4-(5-(trifluoromethyl)-1,2,4-oxadiazol-3-yl) benzamide;
(R)-N-(1-(ethyl(isopropyl)amino)propan-2-yl)-2-fluoro-4-(5-(trifluoromethyl)-1,2,4-oxadiazol-3-yl)benzamide;
(R)-N-(1-methylpyrrolidin-3-yl)-4-(5-(trifluoromethyl)-1,2,4-oxadiazol-3 -yl)benzamide;
(R)-N-(1-methylpiperidin-3-yl)-4-(5-(trifluoromethyl)-1,2,4-oxadiazol-3-yl)benzamide;
N-(2-(diethylamino)ethyl)-4-(5-(trifluoromethyl)-1,2,4-oxadiazol-3-yl)benzamide; and
N-(2-(methylamino)ethyl)-4-(5-(trifluoromethyl)-1,2,4-oxadiazol-3-yl)benzamide;
or a pharmaceutically acceptable salt thereof.

13. A compound selected from:
(4-phenylpiperazin-1-yl)(4-(5-(trifluoromethyl)-1,2,4-oxadiazol-3-yl)phenyl)methanone;
(4-benzylpiperidin-1-yl)(4-(5-(trifluoromethyl)-1,2,4-oxadiazol-3-yl)phenyl)methanone;
N-(4-(morpholinomethyl)benzyl)-4-(5-(trifluoromethyl)-1,2,4-oxadiazol-3-yl)benzamide;
(R)-N-(1-(benzyl(methyl)amino)propan-2-yl)-4-(5-(trifluoromethyl)-1,2,4-oxadiazol-3-yl) benzamide; and
N-(2-(phenylamino)ethyl)-4-(5-(trifluoromethyl)-1,2,4-oxadiazol-3-yl)benzamide or a pharmaceutically acceptable salt thereof.

14. A pharmaceutical composition comprising a compound according to claim 1, or a pharmaceutically acceptable salt thereof, as active pharmaceutical ingredient in association with at least one pharmaceutically acceptable carrier or diluent.

15. A method for the treatment of muscle atrophy, in a subject in need of such treatment, which method comprises administering to such subject an effective amount of a compound according to claim 1, or a pharmaceutically acceptable salt thereof.

16. A method for the treatment of Huntington's disease, metabolic syndrome or diabetes, in a subject having Huntington's disease, metabolic syndrome or diabetes, which method comprises administering to such subject an effective amount of a compound according to claim 1, or a pharmaceutically acceptable salt thereof.

17. A pharmaceutical combination comprising a therapeutically effective amount of a compound according to claim 1, or a pharmaceutically acceptable salt thereof, and a second drug substance, for simultaneous or sequential administration.

* * * * *